(12) United States Patent
Liu et al.

(10) Patent No.: US 9,999,623 B2
(45) Date of Patent: Jun. 19, 2018

(54) USE OF SUBSTITUTED 2,3-DIHYDROIMIDAZO[1,2-C]QUINAZOLINES FOR TREATING LYMPHOMAS

(71) Applicant: BAYER PHARMA AKTIENGESELLSCHAFT, Berlin (DE)

(72) Inventors: Ningshu Liu, Berlin (DE); Katja Haike, Potsdam (DE); Juliane Paul, Berlin (DE); Antje Margret Wengner, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days. days.

(21) Appl. No.: 14/781,224

(22) PCT Filed: Apr. 4, 2014

(86) PCT No.: PCT/EP2014/056768
§ 371 (c)(1),
(2) Date: Sep. 29, 2015

(87) PCT Pub. No.: WO2014/166820
PCT Pub. Date: Oct. 16, 2014

(65) Prior Publication Data
US 2016/0058770 A1    Mar. 3, 2016

(30) Foreign Application Priority Data

Apr. 8, 2013  (EP) .................................... 13162710
Sep. 13, 2013 (EP) .................................... 13184240

(51) Int. Cl.
| | | |
|---|---|---|
| A61K 31/52 | (2006.01) | |
| A61K 31/522 | (2006.01) | |
| A61K 31/519 | (2006.01) | |
| A61K 31/5365 | (2006.01) | |
| A61K 31/5377 | (2006.01) | |
| A61K 31/18 | (2006.01) | |
| A61K 31/277 | (2006.01) | |
| A61K 45/06 | (2006.01) | |

(52) U.S. Cl.
CPC .......... *A61K 31/5377* (2013.01); *A61K 31/18* (2013.01); *A61K 31/277* (2013.01); *A61K 31/519* (2013.01); *A61K 31/52* (2013.01); *A61K 31/522* (2013.01); *A61K 31/5365* (2013.01); *A61K 45/06* (2013.01)

(58) Field of Classification Search
CPC .... A61K 31/52; A61K 31/522; A61K 31/519; A61K 31/5365
See application file for complete search history.

(56) References Cited

U.S. PATENT DOCUMENTS

| | | |
|---|---|---|
| 1,364,099 A1 | 3/2013 | Liu et al. |
| 1,400,959 A1 | 11/2013 | Peters et al. |
| 1,400,975 A1 | 5/2014 | Liu et al. |
| 9,636,344 B2 | 5/2017 | Peters et al. |
| 2013/0184270 A1 | 7/2013 | Liu et al. |
| 2014/0072529 A1 | 3/2014 | Peters et al. |
| 2014/0243295 A1 | 8/2014 | Liu et al. |

FOREIGN PATENT DOCUMENTS

| | | |
|---|---|---|
| WO | WO-2008/070150 A1 | 6/2008 |
| WO | WO-2010034414 | 4/2010 |
| WO | WO-2012/062748 A1 | 5/2012 |
| WO | WO2012062748 A1 * | 5/2012 |
| WO | WO-2012/121953 A1 | 9/2012 |
| WO | WO-2012136549 | 10/2012 |
| WO | WO-2013/006443 A2 | 1/2013 |
| WO | WO-2013/169858 A1 | 11/2013 |

OTHER PUBLICATIONS

Castillo, "CAL-101: a phosphatidylinositol-3-kinase p110-delta inhibitor for the treatment of lymphoid malignancies", Expert Opin Investig Drugs. Jan. 2012;21(1):15-22.*
Liu, N. et al (Oct. 29, 2013). "Bay 80/6946 Is a Highly Selective Intravenous PI3K Inhibitor with Potent p110α and p110δ Activities in Tumor Cell Lines and Xenograft Models," *Molecular cancer Therapeutics* 12(11): 2319-2330.
Advani, R. H. et al. (Jan. 2013) "Bruton Tyrosine Kinase Inhibitor Ibrutinib (PCI-32765) Has Significant Activity in Patients With Relapsed/Refractory B-Cell Malignancies" *Journal of Clinical Oncology* 31(1): 88-93.
Herman, S.E.M. et al. (Sep. 2010) "Phosphatidylinositol 3-kinase-δ inhibitor CAL-101 shows promising preclinical activity in chronic lymphocytic leukemia by antagonizing intrinsic and extrinsic cellular survival signals" *Blood* 23(116): 2078-2087.
Schulz, M.M.P. et al. (Sep. 2012) "Phenotype-based high-content chemical library screening identifies statins as inhibitors of in vivo lymphangiogenesis" *PNAS*, E2665-E2674.

* cited by examiner

*Primary Examiner* — Sahar Javanmard
(74) *Attorney, Agent, or Firm* — Morrison and Foerster LLP

(57) ABSTRACT

Described herein are methods of treating non-Hodgkin's lymphoma (NHL), wherein the non-Hodgkin's lymphoma (NHL) is selected from the group consisting of 1st line, 2nd line, relapsed, refractory, indolent or aggressive non-Hodgkin's lymphoma (NHL); follicular lymphoma (FL); chronic lymphocytic leukemia (CLL); marginal zone lymphoma (MZL); diffuse large B-cell lymphoma (DLBCL); mantle cell lymphoma (MCL); transformed lymphoma (TL); and peripheral T-cell lymphoma (PTCL). comprising administering to a patient in need thereof a 2,3-dihydroimidazo[1,2-c] quinazoline compound, or a salt thereof.

3 Claims, 16 Drawing Sheets

Combination effect of PI3K inhibitor COMPOUND A with BTK inhibitor ibrutinib or IKK inhibitor BAY compound B in DLBCL cell lines

| Combination | CI | HBL-1 CD79, MyD88 | TMD-8 CD79 | OCI-Ly3 CARD11, MyD88, Bcl2 | OCI-Ly19 Bcl2 | SU-DHL-4 Bcl2, EZH2 | SU-DHL-5 | SU-DHL-8 c-Myc | SU-DHL-10 Bcl2, EZH2, c-Myc |
|---|---|---|---|---|---|---|---|---|---|
| PI3Ki BAY Cpd A + BTKi PCI32765 | IC$_{50}$ | | | | | | | | |
| | IC$_{90}$ | | | | | | | | |
| PI3Ki BAY Cpd A + IKKi BAY Cpd B | IC$_{50}$ | | | | | | | | |
| | IC$_{90}$ | | | | | | | | |

■ Very strong synergy, CI: 0-0.3
▨ Strong synergy, CI: 0.3-0.6
□ Synergy, CI: 0.6-0.9
□ Additive effect: CI: 0.9-1.2
▨ Antagonistic effect: CI: >1.2

CI: combination index; NA: not achievable at a concentration of 10μM of the two compounds

Fig. 6A

PI3Ki: BAY Compound A, BTKi: ibrutinib, IKKβ: BAY Compound B, CAL-101: GS-101

$^1$H-NMR Spectrum of the compound A $^{13}$C-NMR Spectrum of the compound A

US 9,999,623 B2

USE OF SUBSTITUTED 2,3-DIHYDROIMIDAZO[1,2-C]QUINAZOLINES FOR TREATING LYMPHOMAS

CROSS REFERENCE TO RELATED APPLICATIONS

This application is a National Phase application under 35 U.S.C. § 371 of International Application No. PCT/EP2014/056768, filed Apr. 4, 2014, which claims priority benefit of European Application No. 13162710.1, filed on Apr. 8, 2013, and European Application No. 13184240.3, filed on Sep. 13, 2013, the disclosures of each of which are hereby incorporated by reference in their entireties.

The present invention relates to:
use of a 2,3-dihydroimidazo[1,2-c]quinazoline compound, or of a pharmaceutical composition containing same, as a sole active agent, or of a combination of a) said compound or a pharmaceutical composition containing said compound and b) one or more further active agents, for the preparation of a medicament for the treatment or prophylaxis of non-Hodgkin's lymphoma (hereinafter abbreviated to "NHL"), particularly 1st line, 2nd line, relapsed, refractory, indolent or aggressive non-Hodgkin's lymphoma (NHL), in particular follicular lymphoma (hereinafter abbreviated to "FL"), chronic lymphocytic leukaemia (hereinafter abbreviated to "CLL"), marginal zone lymphoma (hereinafter abbreviated to "MZL"), diffuse large B-cell lymphoma (hereinafter abbreviated to "DLBCL"), mantle cell lymphoma (MCL), transformed lymphoma (hereinafter abbreviated to "TL"), or peripheral T-cell lymphoma (hereinafter abbreviated to "PTCL"); as a single agent or in combination with one or more other active agents;
combinations of a) said compound and b) one or more further active agents;
a pharmaceutical composition comprising said compound as a sole active agent for the treatment of cancer;
a pharmaceutical composition comprising a combination of a) said compound and b) one or more further active agents;
use of biomarkers, such as the expression of PI3K isoforms, BTK, IKK, BCR activation, BCR downstream activation of NFκβ pathway, c-Myc, EZH2, for predicting the sensitivity and/or resistance of a cancer patient to said compound and providing a rationale-based synergistic combination as defined herein to increase sensitivity and/or to overcome resistance; and
a method of determining the level of a component of one or more of the expression of PI3K isoforms, BTK, IKK, BCR activation, BCR downstream activation of NFκB pathway, c-Myc, EZH2.

BACKGROUND OF THE INVENTION

In recent decades the concept of developing anti-cancer medications which target abnormally active protein kinases has led to a number of successes. In addition to the actions of protein kinases, lipid kinases also play an important role in generating critical regulatory second messengers. The PI3K family of lipid kinases generates 3'-phosphoinositides that bind to and activate a variety of cellular targets, initiating a wide range of signal transduction cascades (Vanhaesebroeck et al., 2001; Toker, 2002; Pendaries et al., 2003; Downes et al., 2005). These cascades ultimately induce changes in multiple cellular processes, including cell proliferation, cell survival, differentiation, vesicle trafficking, migration, and chemotaxis.

PI3Ks can be divided into three distinct classes based upon differences in both structure, and substrate preference. While members of the Class II family of PI3Ks have been implicated in the regulation of tumor growth (Brown and Shepard, 2001; Traer et al., 2006), the bulk of research has focused on the Class I enzymes and their role in cancer (Vivanco and Sawyers, 2002; Workman, 2004, Chen et al., 2005; Hennessey et al., 2005; Stauffer et al., 2005; Stephens et al., 2005; Cully et al., 2006).

Class I PI3Ks have traditionally been divided into two distinct sub-classes based upon differences in protein sub-unit composition. The Class $I_A$ PI3Ks are comprised of a catalytic p110 catalytic subunit (p110α, p110β or p110γ) heterodimerized with a member of the p85 regulatory subunit family. In contrast, the Class $I_B$ PI3K catalytic subunit (p110γ) heterodimerizes with a distinct p101 regulatory subunit (reviewed by Vanhaesebroeck and Waterfield, 1999; Funaki et al., 2000; Katso et al., 2001). The C-terminal region of these proteins contains a catalytic domain that possesses distant homology to protein kinases. The PI3Kγ structure is similar to Class $I_A$ p110s, but lacks the N-terminal p85 binding site (Domin and Waterfield, 1997). Though similar in overall structure, the homology between catalytic p110 subunits is low to moderate. The highest homology between the PI3K isoforms is in the kinase pocket of the kinase domain.

The Class I PI3K isoforms associate with activated receptor tyrosine kinases (RTKs) (including PDGFR, EGFR, VEGFR, IGF1-R, c-KIT, CSF-R and Met), cytokine receptors, GPCRs, integrins, or with tyrosine phosphorylated adapter proteins (such as Grb2, Cbl, IRS-1 or Gab1), via their p85 regulatory subunits resulting in stimulation of the lipid kinase activity. Activation of the lipid kinase activity of the p110β and p110γ isoforms has been shown to occur in response to binding to activated forms of the ras Oncogene (Kodaki et al, 1994). In fact, the oncogenic activity of these isoforms may require binding to ras (Kang et al., 2006). In contrast, the p110α and p110δ isoforms exhibit oncogenic activity independent of ras binding, through constitutive activation of Akt.

Class I PI3Ks catalyze the conversion of PI(4,5)$P_2$ [PIP$_2$] to PI(3,4,5)$P_3$ [PIP$_3$]. The production of PIP$_3$ by PI3K affects multiple signaling processes that regulate and coordinate the biological end points of cell proliferation, cell survival, differentiation and cell migration. PIP$_3$ is bound by Pleckstrin-Homology (PH) domain-containing proteins, including the phosphoinositide-dependent kinase, PDK1 and the Akt proto-oncogene product, localizing these proteins in regions of active signal transduction and also contributing directly to their activation (Klippel et al., 1997; Fleming et al., 2000; Itoh and Takenawa, 2002; Lemmon, 2003). This co-localization of PDK1 with Akt facilitates the phosphorylation and activation of Akt. Carboxy-terminal phosphorylation of Akt on Ser$^{473}$ promotes phosphorylation of Thr$^{308}$ in the Akt activation loop (Chan and Tsichlis, 2001; Hodgekinson et al., 2002; Scheid et al., 2002; Hresko et al., 2003). Once active, Akt phosphorylates and regulates multiple regulatory kinases of pathways that directly influence cell cycle progression and cell survival.

Many of the effects of Akt activation are mediated via its negative regulation of pathways which impact cell survival and which are commonly dysregulated in cancer. Akt promotes tumor cell survival by regulating components of the apoptotic and cell cycle machinery. Akt is one of several kinases that phosphorylate and inactivate pro' apoptotic BAD proteins (del Paso et al., 1997; Pastorino et al., 1999). Akt may also promote cell survival through blocking cytochrome C-dependent caspase activation by phosphorylating Caspase 9 on $Ser^{196}$ (Cardone et al., 1998).

Akt impacts gene transcription on several levels. The Akt-mediated phosphorylation of the MDM2 E3 ubiquitin ligase on $Ser^{166}$ and $Ser^{186}$ facilitates the nuclear import of MDM2 and the formation and activation of the ubiquitin ligase complex. Nuclear MDM2 targets the p53 tumor suppressor for degradation, a process that can be blocked by LY294002 (Yap et al., 2000; Ogarawa et al., 2002). Down-regulation of p53 by MDM2 negatively impacts the transcription of p53-regulated pro-apoptotic genes (e.g. Bax, Fas, PUMA and DR5), the cell cycle inhibitor, $p21^{Cip1}$, and the PTEN tumor suppressor (Momand et al., 2000; Hupp et al., 2000; Mayo et al., 2002; Su et al., 2003). Similarly, the Akt-mediated phosphorylation of the Forkhead transcription factors FKHR, FKHRL and AFX (Kops et al., 1999; Tang et al., 1999), facilitates their binding to 14-3-3 proteins and export from the cell nucleus to the cytosol (Brunet et al., 1999). This functional inactivation of Forkhead activity also impacts pro-apoptotic and pro-angiogenic gene transcription including the transcription of Fas ligand (Ciechomska et al., 2003) Bim, a pro-apoptotic Bcl-2 family member (Dijkers et al., 2000), and the Angiopoietin-1 (Ang-1) antagonist, Ang-2 (Daly et al., 2004). Forkhead transcription factors regulate the expression of the cyclin-dependent kinase (Cdk) inhibitor $p27^{Kip1}$. Indeed, PI3K inhibitors have been demonstrated to induce $p27^{Kip1}$ expression resulting in Cdk1 inhibition, cell cycle arrest and apoptosis (Dijkers et al., 2000). Akt is also reported to phosphorylate $p21^{Cip1}$ on $Thr^{145}$ and $p27^{Kip1}$ on $Thr^{157}$ facilitating their association with 14-3-3 proteins, resulting in nuclear export and cytoplasmic retention, preventing their inhibition of nuclear Cdks (Zhou et al., 2001; Motti et al., 2004; Sekimoto et al., 2004). In addition to these effects, Akt phosphorylates IKK (Romashkova and Makarov, 1999), leading to the phosphorylation and degradation of IκB B and subsequent nuclear translocation of NFκB, resulting in the expression of survival genes such as IAP and $Bcl-X_L$.

The PI3K/Akt pathway is also linked to the suppression of apoptosis through the JNK and $p38^{MAPK}$ MAP Kinases that are associated with the induction of apoptosis. Akt is postulated to suppress JNK and $p38^{MAPK}$ signaling through the phosphorylation and inhibition of two JNK/p38 regulatory kinases, Apoptosis Signal-regulating Kinase 1 (ASK1) (Kim et al., 2001: Liao and Hung, 2003; Yuan et al., 2003), and Mixed Lineage Kinase 3 (MLK3) (Lopez-llasaca et al., 1997; Barthwal et al., 2003; Figueroa et al., 2003). The induction of $p38^{MAPK}$ activity is observed in tumors treated with cytotoxic agents and is required for those agents to induce cell death (reviewed by Olson and Hallahan, 2004). Thus, inhibitors of the PI3K pathway may promote the activities of co-administered cytotoxic drugs.

An additional role for PI3K/Akt signaling involves the regulation of cell cycle progression through modulation of Glycogen Synthase Kinase 3 (GSK3) activity. GSK3 activity is elevated in quiescent cells, where it phosphorylates cyclin $D_1$ on $Ser^{286}$, targeting the protein for ubiquitination and degradation (Diehl et al., 1998) and blocking entry into S-phase. Akt inhibits GSK3 activity through phosphorylation on $Ser^9$ (Cross et al., 1995). This results in the elevation of Cyclin $D_1$ levels which promotes cell cycle progression. Inhibition of GSK3 activity also impacts cell proliferation through activation of the wnt/beta-catenin signaling pathway (Abbosh and Nephew, 2005; Naito et al., 2005; Wilker et al., 2005; Kim et al., 2006; Segrelles et al., 2006). Akt mediated phosphorylation of GSK3 results in stabilization and nuclear localization of the beta-catenin protein, which in turn leads to increased expression of c-myc and cyclin D1, targets of the beta-catenin/Tcf pathway.

Although PI3K signaling is utilized by many of the signal transduction networks associated with both oncogenes and tumor suppressors, PI3K and its activity have been linked directly to cancer. Overexpression of both the p110α and p110β isoforms has been observed in bladder and colon tumors and cell lines, and overexpression generally correlates with increased PI3K activity (Bénistant et al., 2000). Overexpression of p110α has also been reported in ovarian and cervical tumors and tumor cell lines, as well as in squamous cell lung carcinomas. The overexpression of p110α in cervical and ovarian tumor lines is associated with increased PI3K activity (Shayesteh et al., 1999; Ma et al., 2000). Elevated PI3K activity has been observed in colorectal carcinomas (Phillips et al., 1998) and increased expression has been observed in breast carcinomas (Gershtein et al., 1999).

Over the last few years, somatic mutations in the gene encoding p110α (PIK3CA) have been identified in numerous cancers. The data collected to date suggests that PIK3CA is mutated in approximately 32% of colorectal cancers (Samuels et al., 2004; Ikenoue et al., 2005), 18-40% of breast cancers (Bachman et al., 2004; Campbell et al., 2004; Levine et al., 2005; Saal et al., 2005; Wu et al., 2005), 27% of glioblastomas (Samuels et al., 2004; Hartmann et al., 2005, Gallia et al., 2006), 25% of gastric cancers (Byun et al., 2003; Samuels et al., 2004; Li et al., 2005), 36% of hepatocellular carcinomas (Lee et al., 2005), 4-12% of ovarian cancers (Levine et al., 2005; Wang et al., 2005), 4% of lung cancers (Samuels et al., 2004; Whyte and Holbeck, 2006), and up to 40% of endometrial cancers (Oda et al., 2005). PIK3CA mutations have been reported in oligodendroma, astrocytoma, medulloblastoma, and thyroid tumors as well (Broderick et al., 2004; Garcia-Rostan et al., 2005). Based upon the observed high frequency of mutation, PIK3CA is one of the two most frequently mutated genes associated with cancer, the other being K-ras. More than 80% of the PIK3CA mutations cluster within two regions of the protein, the helical (E545K) and catalytic (H1047R) domains. Biochemical analysis and protein expression studies have demonstrated that both mutations lead to increased constitutive p110α catalytic activity and are in fact, oncogenic (Bader et al., 2006; Kang et al., 2005; Samuels et al., 2005; Samuels and Ericson, 2006). Recently, it has been reported that PIK3CA knockout mouse embryo fibroblasts are deficient in signaling downstream from various growth factor receptors (IGF-1, Insulin, PDGF, EGF), and are resistant to transformation by a variety of oncogenic RTKs (IGFR, wild-type EGFR and somatic activating mutants of EGFR, Her2/Neu)(Zhao et al., 2006).

Functional studies of PI3K in vivo have demonstrated that siRNA-mediated downregulation of p110β inhibits both Akt phosphorylation and HeLa cell tumor growth in nude mice (Czauderna et al., 2003). In similar experiments, siRNA-mediated downregulation of p110β was also shown to inhibit the growth of malignant glioma cells in vitro and in vivo (Pu et al., 2006). Inhibition of PI3K function by dominant-negative p85 regulatory subunits can block mitogenesis and cell transformation (Huang et al., 1996; Rahimi et al., 1996). Several somatic mutations in the genes encoding the p85α and p85β regulatory subunits of PI3K that result in elevated lipid kinase activity have been identified in a number of cancer cells as well (Janssen et al., 1998;

Jimenez et al., 1998; Philp et al., 2001; Jucker et al., 2002; Shekar et al., 2005). Neutralizing PI3K antibodies also block mitogenesis and can induce apoptosis in vitro (Roche et al., 1994: Roche et al., 1998; Benistant et al., 2000). In vivo proof-of-principle studies using the PI3K inhibitors LY294002 and wortmannin, demonstrate that inhibition of PI3K signaling slows tumor growth in vivo (Powis et al., 1994; Shultz et al., 1995; Semba et al., 2002; Ihle et al., 2004).

Overexpression of Class I PI3K activity, or stimulation of their lipid kinase activities, is associated with resistance to both targeted (such as imatinib and tratsuzumab) and cytotoxic chemotherapeutic approaches, as well as radiation therapy (West et al., 2002; Gupta et al., 2003; Osaki et al., 2004; Nagata et al., 2004; Gottschalk et al., 2005; Kim et al., 2005). Activation of PI3K has also been shown to lead to expression of multidrug resistant protein-1 (MRP-1) in prostate cancer cells and the subsequent induction of resistance to chemotherapy (Lee et al., 2004).

The importance of PI3K signaling in tumorigenesis is further underscored by the findings that the PTEN tumor suppressor, a PI(3)P phosphatase, is among the most commonly inactivated genes in human cancers (Li et al., 1997, Steck et al., 1997; Ali et al., 1999; Ishii et al., 1999). PTEN dephosphorylates $PI(3,4,5)P_3$ to $PI(4,5)P_2$ thereby antagonizing PI3K-dependent signaling. Cells containing functionally inactive PTEN have elevated levels of $PIP_3$, high levels of activity of PI3K signaling (Haas-Kogan et al., 1998; Myers et al., 1998; Taylor et al., 2000), increased proliferative potential, and decreased sensitivity to pro-apoptotic stimuli (Stambolic et al., 1998). Reconstitution of a functional PTEN suppresses PI3K signaling (Taylor et al., 2000), inhibits cell growth and re-sensitizes cells to pro-apoptotic stimuli (Myers et al., 1998; Zhao et al., 2004). Similarly, restoration of PTEN function in tumors lacking functional PTEN inhibits tumor growth in vivo (Stahl et al., 2003; Su et al., 2003; Tanaka and Grossman, 2003) and sensitizes cells to cytotoxic agents (Tanaka and Grossman, 2003).

The class I family of PI3Ks clearly plays an important role in the regulation of multiple signal transduction pathways that promote cell survival and cell proliferation, and activation of their lipid kinase activity contributes significantly to the development of human malignancies. Furthermore, inhibition of PI3K may potentially circumvent the cellular mechanisms that underlie resistance to chemotherapeutic agents. A potent inhibitor of Class I PI3K activities would therefore have the potential not only to inhibit tumor growth but to also sensitize tumor cells to pro-apoptotic stimuli in vivo.

Signal transduction pathways originating from chemoattractant receptors are considered to be important targets in controlling leukocyte motility in inflammatory diseases. Leukocyte trafficking is controlled by chemoattractant factors that activate heterotrimeric GPCRs and thereby trigger a variety of downstream intracellular events. Signal transduction along one of these pathways that results in mobilization of free $Ca^{2+}$, cytoskelatal reorganization, and directional movement depends on lipid-dervied second messengers produced by PI3K activity (Wymann et al., 2000; Stein and Waterfield, 2000).

PI3Kγ modulates baseline cAMP levels and controls contractility in cells. Recent research indicates that alterations in baseline cAMP levels contribute to the increased contractility in mutant mice. This research, therefore, shows that PI3Kγ inhibitors afford potential treatments for congestive heart failure, ischemia, pulmonary hypertension, renal failure, cardiac hypertrophy, atherosclerosis, thromboembolism, and diabetes.

PI3K inhibitors would be expected to block signal transduction from GPCRs and block the activation of various immune cells, leading to a broad anti-inflammatory profile with potential for the treatment of inflammatory and immunoregulatory diseases, including asthma, atopic dermatitis, rhinitis, allergic diseases, chronic obstructive pulmonary disease (COPD), septic shock, joint diseases, autoimmune pathologies such as rheumatoid arthritis and Graves' disease, diabetes, cancer, myocardial contractility disorders, thromboembolism, and atherosclerosis.

Activation of the PI3K/AKT pathway by B-cell receptor signaling and its role in the pathogenesis of non-Hodgkin's lymphoma (NHL) have been highlighted in a number of studies. However, the relative importance of phosphoinositide 3-kinase (PI3K) isoforms and other downstream kinases, e.g. Bruton's tyrosine kinase (BTK) and IκB kinase (IKK), for therapeutic application in NHL has not been fully addressed. To answer this question, we selected and characterized a panel of cell lines representing frequent mutations CD79, MyD88, CARD11, Bcl2, c-Myc, or EZH2 in diffuse large B-cell lymphoma (DLBCL), a major type of aggressive NHL. Analyzing the expression of PI3K isoforms indicated that not only PI3Kδ, an isoform known to be enriched in lymphocytes, but also other 3 PI3K isoforms are highly expressed. Sensitivity profiling of the pan-PI3K inhibitor COMPOUND A (with potent activity against PI3Kα [$IC_{50}$=0.5 nM] and PI3Kδ [$IC_{50}$=0.7 nM]), the PI3Kδ-selective inhibitor GS-1101, the irreversible BTK inhibitor ibrutinib (PCI-32765), and the IKKβ inhibitor BAY compound B revealed that the pan-PI3K inhibitor COMPOUND A has a broader antitumor spectrum and is more effective than inhibition of PI3Kδ or BTK only. Further analysis of oncogenic signaling pathways discovered feedback activation of ERK by PI3Kδ- or BTK-selective inhibition, and re-activation of IKK by IKKβ inhibition. Combination of PI3K inhibitor COMPOUND A with BTK or IKK inhibitors showed synergistic antitumor effects in a subset of tumor cell lines, indicating the heterogeneity of DLBCL and that a biomarker might be necessary for successfully developing COMPOUND A-based therapeutics in aggressive NHL. Taken together, these findings provide further insights into the mechanism of action of PI3K inhibitor COMPOUND A and support ongoing Phase II clinical studies in NHL patients Follicular lymphoma and diffuse large B-cell lymphoma (DLBCL) are 2 of the most common non-Hodgkin's lymphomas (NHLs) worldwide. There remains a high unmet medical need for effective therapeutics for refractory and relapsed follicular lymphoma and DLBCL.

The critical role of phosphoinositide 3-kinase (PI3K)δ in regulating downstream events of the B-cell receptor (BCR) has been evident by the clinical benefit of GS-1101, a PI3Kδ-selective inhibitor in follicular lymphoma patients.

Several lines of evidence suggested that a pan-PI3K inhibitor may produce a better therapeutic benefit compared with PI3Kδ-selective inhibition.

In PI3Kδ knockout mice, PI3Kα was shown to compensate tonic signaling, a characteristic of many B-cell malignancies (see reference 1A).

8% of DLBCL patients have a PIK3CA mutation and 37% have reduced PTEN expression or loss of function of PTEN.

In the clinic, p110α-mediated constitutive PI3K signaling appeared to limit the efficacy of p110δ-selective inhibition in mantle cell lymphoma (see reference 2A).

Although the PI3Kδ-selective inhibitor GS-1101 demonstrated promising clinical response in indolent NHL, so far no efficacy has been shown in aggressive NHL, eg DLBCL.

COMPOUND A is a pan-PI3K inhibitor potently inhibiting PI3Kα and PI3Kδ, with $IC_{50}$ values of 0.5 and 0.7 nM, respectively (see reference 3A).

In this study, we investigated the effects and the mechanism of action of inhibiting key molecular targets in NHL cells using the pan-PI3K inhibitor COMPOUND A, PI3Kδ-selective inhibitor GS-1101, Bruton's tyrosine kinase (BTK) inhibitor ibrutinib (PCI-32765), and an IκB kinase (IKK) inhibitor BAY compound B (see reference 4A) as single agents.

Based on the mechanism of action, the present patent application relates to and covers rational combination therapies for effective treatment of aggressive NHL.

The present invention is thus to identify molecular markers predicting the sensitivity and/or resistance of the cancer patients toward the PI3K inhibitors described herein. Furthermore, the present invention also relates to the identification of resistance mechanisms and therefore provides a rationale-based synergistic combination to overcome the resistance.

To the Applicant's knowledge, no specific disclosure in the prior art is known that 2,3-dihydroimidazo[1,2-c]quinazoline compounds would be effective in the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

It has been found, and this is the basis of the present invention, that 2,3-dihydroimidazo[1,2-c]quinazoline compounds, as described and defined herein, show a beneficial effect in the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

Thus, in accordance with a first aspect, the present invention relates to the use of 2,3-dihydroimidazo[1,2-c]quinazoline compounds, or a physiologically acceptable salt, solvate, hydrate or stereoisomer thereof, as a sole active agent, or of pharmaceutical compositions containing such compounds or a physiologically acceptable salt, solvate, hydrate or stereoisomer thereof, for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In accordance with a second aspect, the present invention relates to combinations of:

a) a 2,3-dihydroimidazo[1,2-c]quinazoline compound, or a physiologically acceptable salt, solvate, hydrate or stereoisomer thereof; and b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of: PI3Kδ-selective inhibitor GS-1101, BTK inhibitor ibrutinib, IKK inhibitor BAY Compound B, and REFAMETINIB (BAY 86-9766 (RDEA-119)).

In accordance with a third aspect, the present invention relates to pharmaceutical compositions comprising a 2,3-dihydroimidazo[1,2-c]quinazoline compound, or a physiologically acceptable salt, solvate, hydrate or stereoisomer thereof, as a sole active agent, for the treatment of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In accordance with a fourth aspect, the present invention relates to pharmaceutical compositions comprising a combination of:

a) a 2,3-dihydroimidazo[1,2-c]quinazoline compound, or a physiologically acceptable salt, solvate, hydrate or stereoisomer thereof; and b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of: PI3Kδ-selective inhibitor GS-1101, BTK inhibitor ibrutinib, IKK inhibitor BAY Compound B, and REFAMETINIB (BAY 86-9766 (RDEA-119)).

In accordance with a fifth aspect, the present invention relates to the use of combinations of:

a) a 2,3-dihydroimidazo[1,2-c]quinazoline compound, or a physiologically acceptable salt, solvate, hydrate or stereoisomer thereof;

or of a pharmaceutical composition containing such a compound or a physiologically acceptable salt, solvate, hydrate or stereoisomer thereof, and b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of: PI3Kδ-selective inhibitor GS-1101, BTK inhibitor ibrutinib, IKK inhibitor BAY Compound B, and REFAMETINIB (BAY 86-9766 (RDEA-119));

for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In accordance with a sixth aspect, the present invention relates to use of biomarkers involved in the modification of target expression, BCR activation, BCR downstream activation of NFκB pathway, c-Myc, EZH2, for predicting the sensitivity and/or resistance of a patient with non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL), to a 2,3-dihydroimidazo[1,2-c]quinazoline compound as defined herein, thus providing a rationale-based synergistic combination as defined herein to overcome the resistance (patient stratification).

In accordance with a seventh aspect, the present invention relates to a method of determining the level of a component of one or more of the expression of PI3K isoforms, BTK, IKK, BCR activation, BCR downstream activation of NFκB pathway, c-Myc, EZH2.

In accordance a particular embodiment of any of the above aspects of the present invention, said cancer is non-Hodgkin's lymphoma (NHL), particularly 1st line, 2nd line, relapsed, refractory, indolent or aggressive non-Hodgkin's lymphoma (NHL).

In accordance a particular embodiment of any of the above aspects of the present invention, said cancer is follicular lymphoma (FL).

In accordance a particular embodiment of any of the above aspects of the present invention, said cancer is chronic lymphocytic leukaemia (CLL).

In accordance a particular embodiment of any of the above aspects of the present invention, said cancer is marginal zone lymphoma (MZL).

In accordance a particular embodiment of any of the above aspects of the present invention, said cancer is diffuse large B-cell lymphoma (DLBCL).

In accordance a particular embodiment of any of the above aspects of the present invention, said cancer is mantle cell lymphoma (MCL).

In accordance a particular embodiment of any of the above aspects of the present invention, said cancer is transformed lymphoma (TL).

In accordance a particular embodiment of any of the above aspects of the present invention, said cancer is peripheral T-cell lymphoma (PTCL).

BRIEF DESCRIPTION OF THE DRAWINGS

FIG. 6A shows the combination effect of PI3K inhibitor COMPOUND A with BTK inhibitor ibrutinib or IKK inhibitor BAY Compound B in DLBCL cell lines. The anti-proliferative effect was investigated using a 72-h CellTiter-Glo® assay.

DETAILED DESCRIPTION OF THE INVENTION

Figure 1:
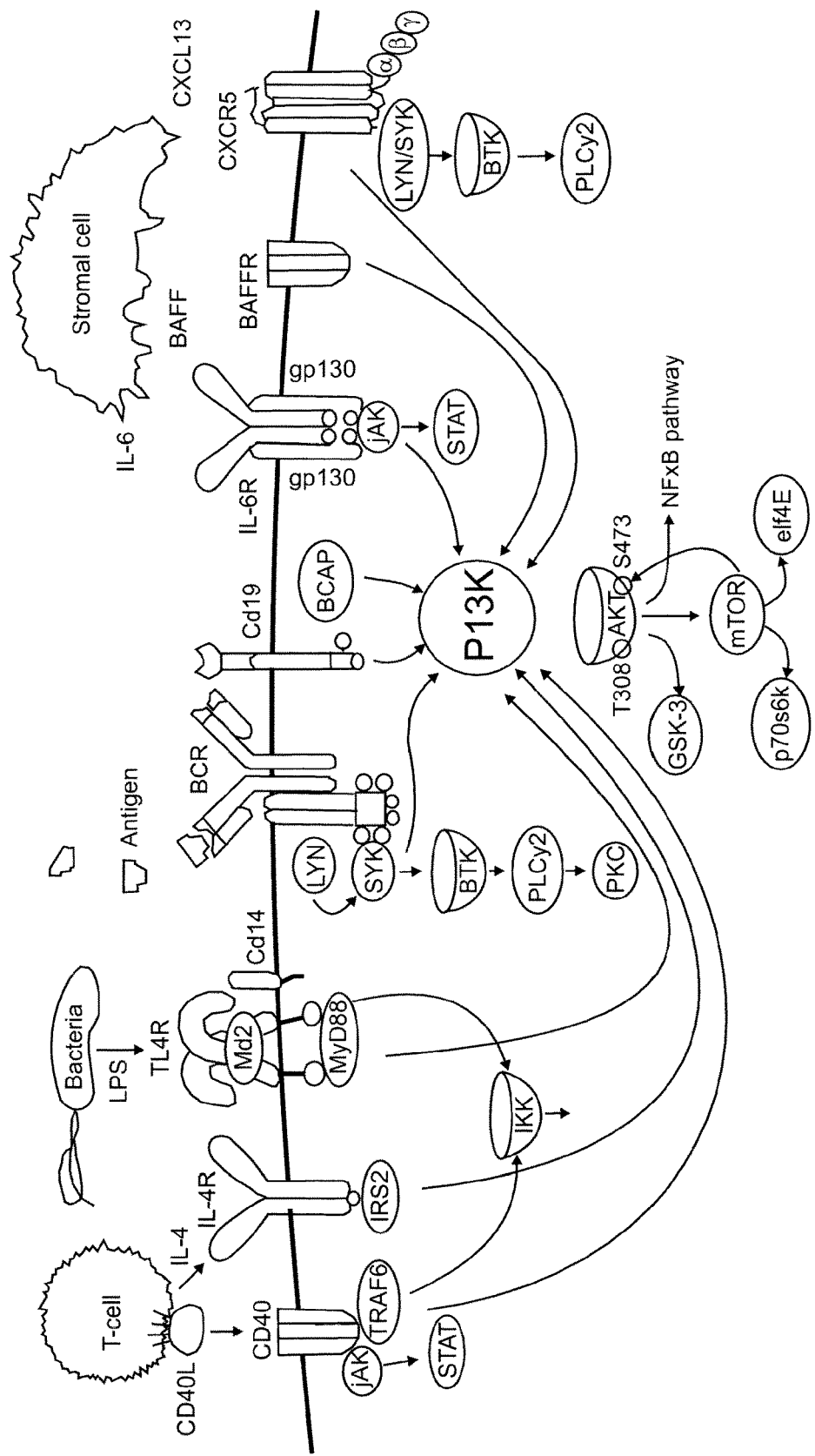
FIG. 1 shows signaling pathways downstream of receptors on B-cells.

A first aspect of the present invention relates to the use of a compound of general formula (A):

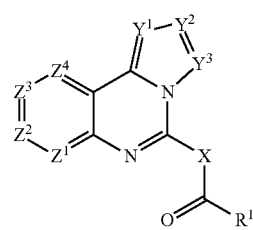

(A)

in which:
X represents $CR^5R^6$ or NH;
$Y^1$ represents $CR^3$ or N;
the chemical bond between $Y^2$═$Y^3$ represents a single bond or double bond,
with the proviso that when the $Y^2$═$Y^3$ represents a double bond, $Y^2$ and $Y^3$ independently represent $CR^4$ or N, and
when $Y^2$═$Y^3$ represents a single bond, $Y^2$ and $Y^3$ independently represent $CR^3R^4$ or $NR^4$;
$Z^1$, $Z^2$, $Z^3$ and $Z^4$ independently represent CH, $CR^2$ or N;
$R^1$ represents aryl optionally having 1 to 3 substituents selected from $R^{11}$, $C_{3-8}$ cycloalkyl optionally having 1 to 3 substituents selected from $R^{11}$, $C_{1-6}$ alkyl optionally substituted by aryl, heteroaryl, $C_{1-6}$ alkoxyaryl, aryloxy, heteroaryloxy or one or more halogen,
$C_{1-6}$ alkoxy optionally substituted by carboxy, aryl, heteroaryl, $C_{1-6}$ alkoxyaryl, aryloxy, heteroaryloxy or one or more halogen, or
a 3 to 15 membered mono- or bi-cyclic heterocyclic ring that is saturated or unsaturated, optionally having 1 to 3 substituents selected from $R^{11}$, and contains 1 to 3 heteroatoms selected from the group consisting of N, O and S,
wherein
$R^{11}$ represents halogen, nitro, hydroxy, cyano, carboxy, amino, N—($C_{1-6}$alkyl)amino, N-(hydroxy$C_{1-6}$alkyl)

amino, N,N-di($C_{1-6}$alkyl)amino, N—($C_{1-6}$acyl) amino, N-(formyl)-N—($C_{1-6}$alkyl)amino, N—($C_{1-6}$ alkanesulfonyl)amino, N-(carboxy$C_{1-6}$alkyl)-N—($C_{1-6}$alkyl)amino, N—($C_{1-6}$alkoxycabonyl)amino, N-[N,N-di($C_{1-6}$alkyl)amino methylene]amino, N-[N,N-di($C_{1-6}$alkyl)amino ($C_{1-6}$alkyl)methylene] amino, N-[N,N-di($C_{1-6}$alkyl)amino $C_{2-6}$alkenyl] amino, aminocarbonyl, N—($C_{1-6}$alkyl)aminocarbonyl, N,N-di($C_{1-6}$alkyl)aminocarbonyl, $C_{3-8}$cycloalkyl, $C_{1-6}$, alkylthio, $C_{1-6}$alkanesulfonyl, sulfamoyl, $C_{1-6}$alkoxycarbonyl, N-arylamino wherein said aryl moiety is optionally having 1 to 3 substituents selected from $R^{101}$, N-(aryl $C_{1-6}$alkyl) amino wherein said aryl moiety is optionally having 1 to 3 substituents selected from $R^{101}$, aryl $C_{1-6}$alkoxycarbonyl wherein said aryl moiety is optionally having 1 to 3 substituents selected from $R^{101}$, $C_{1-6}$ alkyl optionally substituted by mono-, di- or tri-halogen, amino, N—($C_{1-6}$ alkyl)amino or N,N-di($C_{1-6}$ alkyl)amino, $C_{1-6}$ alkoxy optionally substituted by mono-, di- or tri-halogen, N—($C_{1-6}$ alkyl)sulfonamide, or N-(aryl) sulfonamide, or a 5 to 7 membered saturated or unsaturated ring having 1 to 3 heteroatoms selected from the group consisting of O, S and N, and optionally having 1 to 3 substituents selected from $R^{101}$ wherein $R^{101}$ represents halogen, carboxy, amino, N—($C_{1-6}$ alkyl)amino, N,N-di($C_{1-6}$alkyl)amino, aminocarbonyl, N—($C_{2-6}$alkyl)aminocarbonyl, N,N-di($C_{1-6}$ alkyl)aminocarbonyl, pyridyl, $C_{1-6}$ alkyl optionally substituted by cyano or mono- di- or tri-halogen, and $C_{1-6}$ alkoxy optionally substituted by cyano, carboxy, amino, N—($C_{1-6}$ alkyl)amino, N,N-di($C_{2-6}$ alkyl)amino, aminocarbonyl, N—($C_{1-6}$alkyl) aminocarbonyl, N,N-di($C_{2-6}$alkyl)aminocarbonyl or mono-, di- or tri-halogen;

$R^2$ represents hydroxy, halogen, nitro, cyano, amino, N—($C_{2-6}$alkyl)amino, N,N-di($C_{1-6}$alkyl)amino, N-(hydroxy$C_{1-6}$alkyl)amino, N-(hydroxy$C_{2-6}$alkyl)-N—($C_{2-6}$alkyl)amino, $C_{1-6}$ acyloxy, amino$C_{2-6}$ acyloxy, $C_{2-6}$alkenyl, aryl, a 5-7 membered saturated or unsaturated heterocyclic ring having 1 to 3 heteroatoms selected from the group consisting O, S and N, and optionally substituted by hydroxy, $C_{1-6}$ alkyl, $C_{1-6}$ alkoxy, oxo, amino, amino $C_{1-6}$ alkyl, N—($C_{1-6}$ alkyl)amino, N,N-di($C_{1-6}$ alkyl) amino, N—($C_{1-6}$ acyl)amino, N—($C_{1-6}$ alkyl)carbonylamino, phenyl, phenyl $C_{1-6}$ alkyl, carboxy, $C_{1-6}$alkoxycarbonyl, aminocarbonyl, N—($C_{1-6}$ alkyl)aminocarbonyl, or N,N-di($C_{1-6}$ alkyl)amino, —C(O)—$R^{20}$ wherein $R^{20}$ represents $C_{1-6}$ alkyl, $C_{1-6}$ alkoxy, amino, N—($C_{1-6}$ alkyl)amino, N,N-di($C_{1-6}$alkyl)amino, N—($C_{1-6}$ acyl)amino, or a 5-7 membered saturated or unsaturated heterocyclic ring having 1 to 3 heteroatoms selected from the group consisting O, S and N, and optionally substituted by $C_{1-6}$ alkyl, $C_{1-6}$ alkoxy, oxo, amino, N—($C_{1-6}$alkyl)amino, N,N-di($C_{1-6}$ alkyl)amino, N—($C_{1-6}$ acyl)amino, phenyl, or benzyl, $C_{1-6}$ alkyl optionally substituted by $R^{21}$, or $C_{1-6}$ alkoxy optionally substituted by $R^{21}$, wherein $R^{21}$ represents cyano, mono-, di or tri-halogen, hydroxy, amino, N—($C_{1-6}$alkyl)amino, N,N-di ($C_{1-6}$alkyl)amino, N-(hydroxy$C_{1-6}$ alkyl)amino, N-(halophenyl$C_{1-6}$ alkyl)amino, amino $C_{2-6}$ alkylenyl, $C_{1-6}$ alkoxy, hydroxy$C_{1-6}$ alkoxy, —C(O)—$R^{201}$, —NHC(O)—$R^{201}$, $C_{3-8}$cycloalkyl, isoindolino, phthalimidyl, 2-oxo-1,3-oxazolidinyl, aryl or a 5 or 6 membered saturated or unsaturated heterocyclic ring having 1 to 4 heteroatoms selected from the group consisting of O, S and N, and optionally substituted by hydroxy, $C_{1-6}$ alkyl, $C_{1-6}$ alkoxy, $C_{1-6}$ alkoxycarbonyl, hydroxy$C_{1-6}$ alkoxy, oxo, amino, amino$C_{1-6}$alkyl, N—($C_{1-6}$alkyl) amino, N,N-di($C_{1-6}$alkyl)amino, N—($C_{1-6}$ acyl) amino, or benzyl, wherein $R^{201}$ represents hydroxy, amino, N—($C_{1-6}$ alkyl) amino, N,N-di($C_{1-6}$ alkyl)amino, N-(halophenyl$C_{1-6}$ alkyl)amino, $C_{1-6}$ alkyl, amino$C_{1-6}$ alkyl, amino$C_{2-6}$ alkylenyl, $C_{1-6}$ alkoxy, a 5 or 6 membered saturated or unsaturated heterocyclic ring having 1 to 4 heteroatoms selected from the group consisting of O, S and N, and optionally substituted by hydroxy, $C_{1-6}$ alkyl, $C_{1-6}$ alkoxy, $C_{1-6}$ alkoxycarbonyl, hydroxy$C_{1-6}$ alkoxy, oxo, amino, N—($C_{1-6}$alkyl)amino, N,N-di($C_{1-6}$ alkyl)amino, N—($C_{1-6}$acyl)amino or benzyl;

$R^3$ represents hydrogen, halogen, aminocarbonyl, or $C_{1-6}$ alkyl optionally substituted by aryl $C_{1-6}$ alkoxy or mono-, di- or tri-halogen;

$R^4$ represents hydrogen or $C_{1-6}$ alkyl;

$R^5$ represents hydrogen or $C_{1-6}$ alkyl; and $R^6$ represents halogen, hydrogen or $C_{1-6}$ alkyl, or a physiologically acceptable salt, solvate, hydrate or stereoisomer thereof, as a sole active agent, or of combinations of:

a) such a 2,3-dihydroimidazo[1,2-c]quinazoline compound, or a physiologically acceptable salt, solvate, hydrate or stereoisomer thereof; and b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of: PI3Kδ-selective inhibitor GS-1101, BTK inhibitor ibrutinib, IKK inhibitor BAY Compound B, and REFAMETINIB (BAY 86-9766 (RDEA-119));

or of pharmaceutical compositions containing such compounds or a physiologically acceptable salt, solvate, hydrate or stereoisomer thereof, or of pharmaceutical compositions containing such combinations, for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a particular embodiment of the above-mentioned first aspect, the present invention relates to the use of a compound selected from the following list,
or a physiologically acceptable salt, solvate, hydrate or stereoisomer thereof, as a sole active agent,
or of combinations of:
a) such a 2,3-dihydroimidazo[1,2-c]quinazoline compound, or a physiologically acceptable salt, solvate, hydrate or stereoisomer thereof; and
b) one or more further active agents, in particular an active agent selected from an anti-angiogenesis, anti-hyper-proliferative, antiinflammatory, analgesic, immunoregulatory, diuretic, antiarrytmic, anti-hypercholsterolemia, anti-dyslipidemia, anti-diabetic or antiviral agent, more particularly one or more further active agents selected from the group consisting of: PI3Kδ-selective inhibitor GS-1101, BTK inhibitor ibrutinib, IKK inhibitor BAY Compound B, and REFAMETINIB (BAY 86-9766 (RDEA-119));
or of pharmaceutical compositions containing such compounds or a physiologically acceptable salt, solvate, hydrate or stereoisomer thereof,
or of pharmaceutical compositions containing such combinations
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL):

N-(7,8-dimethoxy-2,3-dihydroimidazo[1,2-c]quinazolin-5-yl)nicotinamide;
2-(7,8-dimethoxy-2,3-dihydroimidazo[1,2-c]quinazolin-5-yl)-1-pyridin-3-ylethylenol;
N-(7,8-dimethoxy-2,3-dihydroimidazo[1,2-c]quinazolin-5-yl)-1H-benzimidazole-5-carboxamide;
6-(acetamido)-N-(7,8-dimethoxy-2,3-dihydroimidazo[1,2-c]quinazolin-5-yl)nicotinamide;
N-{5-[2-(7,8-dimethoxy-2,3-dihydroimidazo[1,2-c]quinazolin-5-yl)-1-hydroxyyinyl]pyridin-2-yl}acetamide;
2-({5-[2-hydroxy-2-pyridin-3-ylyinyl]-7-methoxy-2,3-dihydroimidazo[1,2-c]quinazolin-8-yl}oxy)-N,N-dimethylacetamide;
2-[7-methoxy-8-(tetrahydro-2H-pyran-2-ylmethoxy)-2,3-dihydroimidazo[1,2-c]quinazolin-5-yl]-1-pyridin-3-ylethylenol;
2-[8-(2-hydroxyethoxy)-7-methoxy-2,3-dihydroimidazo[1,2-c]quinazolin-5-yl]-1-pyridin-3-ylethylenol;
({5-[2-hydroxy-2-pyridin-3-ylyinyl]-7-methoxy-2,3-dihydroimidazo[1,2-c]quinazolin-8-yl}oxy)acetic acid;
4-({5-[2-hydroxy-2-pyridin-3-ylyinyl]-7-methoxy-2,3-dihydroimidazo[1,2-c]quinazolin-8-yl}oxy)butanoic acid;
({5-[2-hydroxy-2-pyridin-3-ylyinyl]-7-methoxy-2,3-dihydroimidazo[1,2-c]quinazolin-8-yl}oxy)acetonitrile;
2-[7-methoxy-8-(2H-tetrazol-5-ylmethoxy)-2,3-dihydroimidazo[1,2-c]quinazolin-5-yl]-1-pyridin-3-ylethylenol;
2-[7-methoxy-8-(4-morpholin-4-yl-4-oxobutoxy)-2,3-dihydroimidazo[1,2-c]quinazolin-5-yl]-1-pyridin-3-ylethylenol;
5-[1-hydroxy-2-(8-morpholin-4-yl-2,3-dihydroimidazo[1,2-c]quinazolin-5-yl)vinyl]pyridin-3-ol;
N-(2,3-dihydroimidazo[1,2-c]quinazolin-5-yl)-5-hydroxynicotinamide;
6-(acetamido)-N-(7,9-dimethoxy-8-methyl-2,3-dihydroimidazo[1,2-c]quinazolin-5-yl)nicotinamide;
N-(8,9-dimethoxy-2,3-dihydroimidazo[1,2-c]quinazolin-5-yl)-5-hydroxynicotinamide;
5-hydroxy-N-(7-methoxy-2,3-dihydroimidazo[1,2-c]quinazolin-5-yl)nicotinamide;
N-(7,8-dimethoxy-2,3-dihydroimidazo[1,2-c]quinazolin-5-yl)-5-[(4-methoxybenzyl)oxy]nicotinamide;
N-(7,8-dimethoxy-2,3-dihydroimidazo[1,2-c]quinazolin-5-yl)-5-hydroxynicotinamide;
5-hydroxy-N-[8-(trifluoromethyl)-2,3-dihydroimidazo[1,2-c]quinazolin-5-yl]nicotinamide;
N-{8-[3-(1,3-dioxo-1,3-dihydro-2H-isoindol-2-yl)propoxy]-2,3-dihydroimidazo[1,2-c]quinazolin-5-yl}nicotinamide;
N-(7-bromo-8-methoxy-2,3-dihydroimidazo[1,2-c]quinazolin-5-yl)nicotinamide;
6-amino-N-(8-methoxy-2,3-dihydroimidazo[1,2-c]quinazolin-5-yl)nicotinamide;
1-(1H-benzimidazol-5-yl)-2-(8,9-dimethoxy-2,3-dihydroimidazo[1,2-c]quinazolin-5-yl)ethylenol;
2-(8,9-dimethoxy-2,3-dihydroimidazo[1,2-c]quinazolin-5-yl)-1-(2,4-dimethyl-1,3-thiazol-5-yl)ethylenol;
N-(9-methoxy-2,3-dihydroimidazo[1,2-c]quinazolin-5-yl)-1H-benzimidazole-5-carboxamide;
N-(8-bromo-2,3-dihydroimidazo[1,2-c]quinazolin-5-yl)nicotinamide;
N-(8-bromo-2,3-dihydroimidazo[1,2-c]quinazolin-5-yl)-1H-benzimidazole-5-carboxamide;
N-(8-methoxy-2,3-dihydroimidazo[1,2-c]quinazolin-5-yl)-1H-benzimidazole-5-carboxamide;
N-(8-methyl-2,3-dihydroimidazo[1,2-c]quinazolin-5-yl)-1H-benzimidazole-5-carboxamide;
N-[8-(trifluoromethyl)-2,3-dihydroimidazo[1,2-c]quinazolin-5-yl]-1H-benzimidazole-5-carboxamide;
N-(7-fluoro-2,3-dihydroimidazo[1,2-c]quinazolin-5-yl)-1H-benzimidazole-5-carboxamide;
N-(7-methoxy-2,3-dihydroimidazo[1,2-c]quinazolin-5-yl)nicotinamide;
N-(8-chloro-2,3-dihydroimidazo[1,2-c]quinazolin-5-yl)-1H-benzimidazole-5-carboxamide;
6-(acetamido)-N-(8-morpholin-4-yl-2,3-dihydroimidazo[1,2-c]quinazolin-5-yl)nicotinamide;
1-(1H-benzimidazol-5-yl)-2-(8-morpholin-4-yl-2,3-dihydroimidazo[1,2-c]quinazolin-5-yl)ethylenol;
N-{5-[1-hydroxy-2-(8-morpholin-4-yl-2,3-dihydroimidazo[1,2-c]quinazolin-5-yl)vinyl]pyridin-2-yl}acetamide;
6-methyl-N-(8-morpholin-4-yl-2,3-dihydroimidazo[1,2-c]quinazolin-5-yl)nicotinamide;
1-(1H-benzimidazol-5-yl)-2-[8-(4-methylpiperazin-1-yl)-2,3-dihydroimidazo[1,2-c]quinazolin-5-yl]ethylenol;
N-(2,3-dihydroimidazo[1,2-c]quinazolin-5-yl)-3H-imidazo[4,5-b]pyridine-6-carboxamide;
N-(7,8-dimethoxy-2,3-dihydroimidazo[1,2-c]quinazolin-5-yl)-3H-imidazo[4,5-b]pyridine-6-carboxamide;
N-[7-(trifluoromethyl)-2,3-dihydroimidazo[1,2-c]quinazolin-5-yl]-1H-benzimidazole-5-carboxamide;
N-(7,9-dimethoxy-2,3-dihydroimidazo[1,2-c]quinazolin-5-yl)-1H-benzimidazole-5-carboxamide;
N-{5-[2-(7,9-dimethoxy-8-methyl-2,3-dihydroimidazo[1,2-c]quinazolin-5-yl)-1-hydroxyvinyl]pyridin-2-yl}acetamide;
N-{5-[2-(7-bromo-9-methyl-2,3-dihydroimidazo[1,2-c]quinazolin-5-yl)-1-hydroxyvinyl]pyridin-2-yl}acetamide;
and 2-(8,9-dimethoxy-2,3-dihydroimidazo[1,2-c]quinazolin-5-yl)-1-pyridin-3-ylethylenol;

Another embodiment of the present invention encompasses the use of a compound having the formula (I):

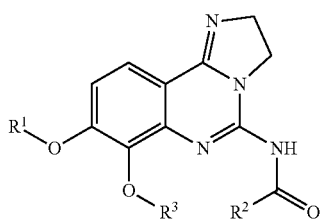

(I)

or a physiologically acceptable salt, solvate, hydrate or stereoisomer thereof, in which:

$R^1$ represents —$(CH_2)_n$—$(CHR^4)$—$(CH_2)_m$—$N(R^5)(R^{5'})$;

$R^2$ represents a heteroaryl optionally substituted with 1, 2 or 3 $R^6$ groups;

$R^3$ represents alkyl or cycloalkyl;

$R^4$ represents hydrogen, hydroxy or alkoxy; and $R^5$ and $R^{5'}$ may be the same or different and represent independently, hydrogen, alkyl, cycloalkylalklyl, or alkoxyalkyl or $R^5$ and $R^{5'}$ may be taken together with the nitrogen atom to which they are bound to form a 3-7 membered nitrogen containing heterocyclic ring optionally containing at least one additional heteroatom selected from oxygen, nitrogen or sulfur and which may be optionally substituted with 1 or more $R^{6'}$ groups, or $R^4$ and $R^5$ may be taken together with the atoms to which they are bound to form a 5-6 membered nitrogen containing heterocyclic ring optionally containing 1 or more nitrogen, oxygen or sulfur atoms and which may be optionally substituted with 1 or more $R^{6'}$ groups;

each occurrence of $R^6$ may be the same or different and is independently halogen, alkyl, alkenyl, alkynyl, cycloalkyl, cycloalkylalklyl, aryl, arylalkyl, heteroaryl, heteroarylalkyl, heterocyclic ring, heterocyclylalkyl, alkyl-$OR^7$, alkyl-SW, alkyl-$N(R^2)(R^2)$, alkyl-$COR^2$, —CN, —$COOR^7$, —CON$(R^7)(R^{7'})$, —$OR^7$, —$SR^7$, —$N(R^7)(R^{7'})$, or $NR^7COR^7$ each of which may be optionally substituted with 1 or more Fe groups;

each occurrence of $R^{6'}$ may be the same or different and is independently alkyl, cycloalkylalklyl, or alkyl-$OR^7$;

each occurrence of $R^2$ and $R^{7'}$ may be the same or different and is independently hydrogen, alkyl, alkenyl, alkynyl, cycloalkyl, cycloalkylalklyl, cycloalkenyl, aryl, arylalkyl, heteroaryl, heterocyclic ring, heterocyclylalkyl, or heteroarylalkyl;

each occurrence of $R^8$ is independently nitro, hydroxy, cyano, formyl, acetyl, halogen, amino, alkyl, alkoxy, alkenyl, alkynyl, cycloalkyl, cycloalkylalklyl, cycloalkenyl, aryl, arylalkyl, heteroaryl, heterocyclic ring, heterocyclylalkyl, or heteroarylalkyl;

n is an integer from 1-4 and m is an integer from 0-4 with the proviso that when $R^4$ and $R^5$ are taken together with the atoms to which they are bound to form a 5-6 membered nitrogen containing ring, n+m≤4;

or a physiologically acceptable salt, solvate, hydrate or stereoisomer thereof, as a sole active agent, or of combinations of:

a) such a 2,3-dihydroimidazo[1,2-c]quinazoline compound, or a physiologically acceptable salt, solvate, hydrate or stereoisomer thereof; and b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of: PI3Kδ-selective inhibitor GS-1101, BTK inhibitor ibrutinib, IKK inhibitor BAY Compound B, and REFAMETINIB (BAY 86-9766 (RDEA-119));

or of pharmaceutical compositions containing such compounds or a physiologically acceptable salt, solvate, hydrate or stereoisomer thereof, or of pharmaceutical compositions containing such combinations, for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a preferred embodiment, the invention encompasses the use of a compound of Formula (I), wherein $R^2$ is a nitrogen containing heteroaryl optionally substituted with 1, 2 or 3 $R^6$ groups, or a physiologically acceptable salt, solvate, hydrate or stereoisomer thereof, as a sole active agent, or of combinations of:

a) such a 2,3-dihydroimidazo[1,2-c]quinazoline compound, or a physiologically acceptable salt, solvate, hydrate or stereoisomer thereof; and b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:

PI3Kδ-selective inhibitor GS-1101, BTK inhibitor ibrutinib, IKK inhibitor BAY Compound B, and REFAMETINIB (BAY 86-9766 (RDEA-119));

or of pharmaceutical compositions containing such compounds or a physiologically acceptable salt, solvate, hydrate or stereoisomer thereof, or of pharmaceutical compositions containing such combinations, for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In another preferred embodiment, the invention encompasses the use of a compound of Formula (I), wherein $R^5$ and $R^{5'}$ are independently alkyl, or a physiologically acceptable salt, solvate, hydrate or stereoisomer thereof, as a sole active agent, or of combinations of:

a) such a 2,3-dihydroimidazo[1,2-c]quinazoline compound, or a physiologically acceptable salt, solvate, hydrate or stereoisomer thereof; and b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:
PI3Kδ-selective inhibitor GS-1101, BTK inhibitor ibrutinib, IKK inhibitor BAY Compound B, and REFAMETINIB (BAY 86-9766 (RDEA-119));
or of pharmaceutical compositions containing such compounds or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In still another preferred embodiment, the invention encompasses the use of a compound of Formula (I), wherein $R^5$ and $R^{5'}$ are taken together with the nitrogen atom to which they are bound to form a 5-6 membered nitrogen containing heterocyclic ring containing at least one additional heteroatom selected from oxygen, nitrogen or sulfur and which may be optionally substituted with 1 or more $R^{6'}$ groups,
or a physiologically acceptable salt, solvate, hydrate or stereoisomer thereof, as a sole active agent,
or of combinations of:
a) such a 2,3-dihydroimidazo[1,2-c]quinazoline compound, or a physiologically acceptable salt, solvate, hydrate or stereoisomer thereof; and
b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:
PI3Kδ-selective inhibitor GS-1101, BTK inhibitor ibrutinib, IKK inhibitor BAY Compound B, and REFAMETINIB (BAY 86-9766 (RDEA-119));
or of pharmaceutical compositions containing such compounds or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In yet another preferred embodiment, the invention encompasses the use of a compound of Formula (I), wherein Fe is hydroxyl,
or a physiologically acceptable salt, solvate, hydrate or stereoisomer thereof, as a sole active agent,
or of combinations of:
a) such a 2,3-dihydroimidazo[1,2-c]quinazoline compound, or a physiologically acceptable salt, solvate, hydrate or stereoisomer thereof; and
b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:
PI3Kδ-selective inhibitor GS-1101, BTK inhibitor ibrutinib, IKK inhibitor BAY Compound B, and REFAMETINIB (BAY 86-9766 (RDEA-119));
or of pharmaceutical compositions containing such compounds or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In another preferred embodiment, the invention encompasses the use of a compound of Formula (I), wherein Fe and $R^5$ are taken together with the atoms to which they are bound to form a 5-6 membered nitrogen containing heterocyclic ring optionally containing 1 or more nitrogen, oxygen or sulfur atoms and which may be optionally substituted with 1 or more $R^6$ groups,
or a physiologically acceptable salt, solvate, hydrate or stereoisomer thereof, as a sole active agent,
or of combinations of:
a) such a 2,3-dihydroimidazo[1,2-c]quinazoline compound, or a physiologically acceptable salt, solvate, hydrate or stereoisomer thereof; and
b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:
PI3Kδ-selective inhibitor GS-1101, BTK inhibitor ibrutinib, IKK inhibitor BAY Compound B, and REFAMETINIB (BAY 86-9766 (RDEA-119));
or of pharmaceutical compositions containing such compounds or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In yet another preferred embodiment, the invention encompasses the use of a compound of Formula (I), wherein $R^3$ is methyl,
or a physiologically acceptable salt, solvate, hydrate or stereoisomer thereof, as a sole active agent,
or of combinations of:
a) such a 2,3-dihydroimidazo[1,2-c]quinazoline compound, or a physiologically acceptable salt, solvate, hydrate or stereoisomer thereof; and
b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:
PI3Kδ-selective inhibitor GS-1101, BTK inhibitor ibrutinib, IKK inhibitor BAY Compound B, and REFAMETINIB (BAY 86-9766 (RDEA-119));
or of pharmaceutical compositions containing such compounds or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In still another preferred embodiment, the invention encompasses the use of a compound of Formula (I), wherein $R^2$ is pyridine, pyridazine, pyrimidine, pyrazine, pyrole, oxazole, thiazole, furan or thiophene, optionally substituted with 1, 2 or 3 $R^6$ groups; more preferably pyridine, pyridazine, pyrimidine, pyrazine, pyrole, oxazole or thiazole, optionally substituted with 1, 2 or 3 $R^6$ groups,
or a physiologically acceptable salt, solvate, hydrate or stereoisomer thereof, as a sole active agent,
or of combinations of:
a) such a 2,3-dihydroimidazo[1,2-c]quinazoline compound, or a physiologically acceptable salt, solvate, hydrate or stereoisomer thereof; and
b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:
PI3Kδ-selective inhibitor GS-1101, BTK inhibitor ibrutinib, IKK inhibitor BAY Compound B, and REFAMETINIB (BAY 86-9766 (RDEA-119));
or of pharmaceutical compositions containing such compounds or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a distinct embodiment, the invention encompasses the use of a compound of formula (Ia)

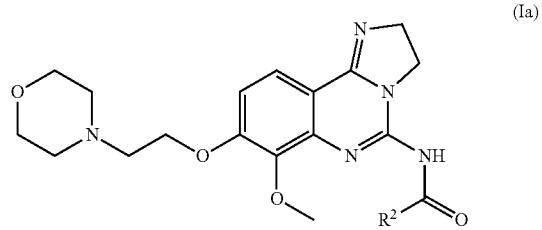

(Ia)

or a physiologically acceptable salt, solvate, hydrate or stereoisomer thereof, wherein $R^2$ is as defined above,
or a physiologically acceptable salt, solvate, hydrate or stereoisomer thereof, as a sole active agent,
or of combinations of:
a) such a 2,3-dihydroimidazo[1,2-c]quinazoline compound, or a physiologically acceptable salt, solvate, hydrate or stereoisomer thereof; and
b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:
PI3Kδ-selective inhibitor GS-1101, BTK inhibitor ibrutinib, IKK inhibitor BAY Compound B, and REFAMETINIB (BAY 86-9766 (RDEA-119));
or of pharmaceutical compositions containing such compounds or a physiologically acceptable salt, solvate, hydrate or stereoisomer thereof,
or of pharmaceutical compositions containing such combinations, for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In another distinct embodiment, the invention encompasses the use of a compound of formula (Ib):

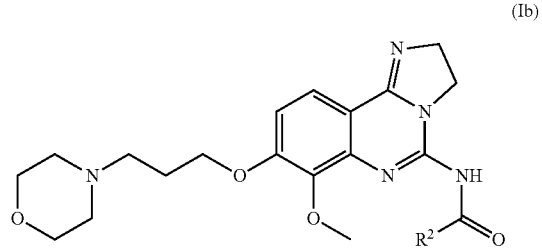

(Ib)

or a physiologically acceptable salt, solvate, hydrate or stereoisomer thereof, wherein $R^2$ is as defined above,
or a physiologically acceptable salt, solvate, hydrate or stereoisomer thereof, as a sole active agent, or of combinations of:

a) such a 2,3-dihydroimidazo[1,2-c]quinazoline compound, or a physiologically acceptable salt, solvate, hydrate or stereoisomer thereof; and b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:

PI3Kδ-selective inhibitor GS-1101, BTK inhibitor ibrutinib, IKK inhibitor BAY Compound B, and REFAMETINIB (BAY 86-9766 (RDEA-119));

or of pharmaceutical compositions containing such compounds or a physiologically acceptable salt, solvate, hydrate or stereoisomer thereof, or of pharmaceutical compositions containing such combinations, for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In still another distinct embodiment, the invention encompasses the use of a compound of formula (Ic):

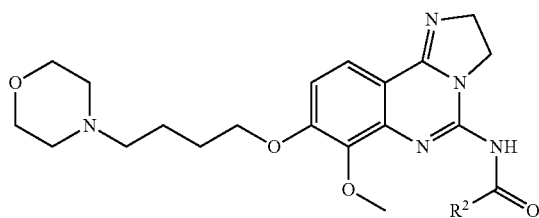

(Ic)

or a physiologically acceptable salt, solvate, hydrate or stereoisomer thereof, wherein $R^2$ is as defined above, or a physiologically acceptable salt, solvate, hydrate or stereoisomer thereof, as a sole active agent, or of combinations of:

a) such a 2,3-dihydroimidazo[1,2-c]quinazoline compound, or a physiologically acceptable salt, solvate, hydrate or stereoisomer thereof; and b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:

PI3Kδ-selective inhibitor GS-1101, BTK inhibitor ibrutinib, IKK inhibitor BAY Compound B, and REFAMETINIB (BAY 86-9766 (RDEA-119));

or of pharmaceutical compositions containing such compounds or a physiologically acceptable salt, solvate, hydrate or stereoisomer thereof, or of pharmaceutical compositions containing such combinations, for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In yet another distinct embodiment, the invention encompasses the use of a compound of the formula (Id):

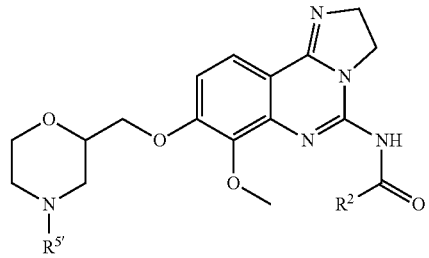

(Id)

or a physiologically acceptable salt, solvate, hydrate or stereoisomer thereof, wherein Fe and Fe are as defined above, or a physiologically acceptable salt, solvate, hydrate or stereoisomer thereof, as a sole active agent, or of combinations of:

a) such a 2,3-dihydroimidazo[1,2-c]quinazoline compound, or a physiologically acceptable salt, solvate, hydrate or stereoisomer thereof; and b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:

PI3Kδ-selective inhibitor GS-1101, BTK inhibitor ibrutinib, IKK inhibitor BAY Compound B, and REFAMETINIB (BAY 86-9766 (RDEA-119));

or of pharmaceutical compositions containing such compounds or a physiologically acceptable salt, solvate, hydrate or stereoisomer thereof, or of pharmaceutical compositions containing such combinations, for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In yet another distinct embodiment, the invention encompasses the use of a compound of the formula (Ie):

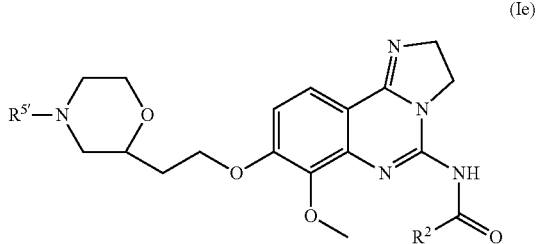

(Ie)

or a physiologically acceptable salt, solvate, hydrate or stereoisomer thereof, wherein R² and Fe are as defined above, or a physiologically acceptable salt, solvate, hydrate or stereoisomer thereof, as a sole active agent, or of combinations of:

a) such a 2,3-dihydroimidazo[1,2-c]quinazoline compound, or a physiologically acceptable salt, solvate, hydrate or stereoisomer thereof; and b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:

PI3Kδ-selective inhibitor GS-1101, BTK inhibitor ibrutinib, IKK inhibitor BAY Compound B, and REFAMETINIB (BAY 86-9766 (RDEA-119));

or of pharmaceutical compositions containing such compounds or a physiologically acceptable salt, solvate, hydrate or stereoisomer thereof, or of pharmaceutical compositions containing such combinations, for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a preferred embodiment, the invention encompasses the use of a compound of formula (I)-(V), wherein Fe is pyridine, pyridazine, pyrimidine, pyrazine, pyrole, oxazole, thiazole, furan or thiophene, optionally substituted with 1, 2 or 3 R⁶ groups; more preferably wherein Fe is pyridine, pyridazine, pyrimidine, pyrazine, pyrole, oxazole or thiazole, optionally substituted with 1, 2 or 3 R⁶ groups, or a physiologically acceptable salt, solvate, hydrate or stereoisomer thereof, as a sole active agent, or of combinations of:

a) such a 2,3-dihydroimidazo[1,2-c]quinazoline compound, or a physiologically acceptable salt, solvate, hydrate or stereoisomer thereof; and b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:

PI3Kδ-selective inhibitor GS-1101, BTK inhibitor ibrutinib, IKK inhibitor BAY Compound B, and REFAMETINIB (BAY 86-9766 (RDEA-119));

or of pharmaceutical compositions containing such compounds or a physiologically acceptable salt, solvate, hydrate or stereoisomer thereof, or of pharmaceutical compositions containing such combinations, for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In still another preferred embodiment, the invention encompasses the use of a compound having the formula:

N-[7-methoxy-8-(3-morpholin-4-ylpropoxy)-2,3-dihydroimidazo[1,2-c]quinazolin-5-yl]pyrimidine-5-carboxamide;

N-(8-{3-[(2R,6S)-2,6-dimethylmorpholin-4-yl]propoxy}-7-methoxy-2,3-dihydroimidazo[1,2-c]quinazolin-5-yl)nicotinamide;

N-(8-{3-[(2R,6S)-2,6-dimethylmorpholin-4-yl]propoxy}-7-methoxy-2,3-dihydroimidazo[1,2-c]quinazolin-5-yl)-2,4-dimethyl-1,3-thiazole-5-carboxamide;

2-amino-N-[7-methoxy-8-(3-morpholin-4-ylpropoxy)-2,3-dihydroimidazo[1,2-c]quinazolin-5-yl]-1,3-thiazole-5-carboxamide;

2-amino-N-[7-methoxy-8-(3-morpholin-4-ylpropoxy)-2,3-dihydroimidazo[1,2-c]quinazolin-5-yl]isonicotinamide;

2-amino-N-[7-methoxy-8-(3-morpholin-4-ylpropoxy)-2,3-dihydroimidazo[1,2-c]quinazolin-5-yl]-4-methyl-1,3-thiazole-5-carboxamide;

2-amino-N-[7-methoxy-8-(3-morpholin-4-ylpropoxy)-2,3-dihydroimidazo[1,2-c]quinazolin-5-yl]-4-propylpyrimidine-5-carboxamide;

N-{8-[2-(4-ethylmorpholin-2-yl)ethoxy]-7-methoxy-2,3-dihydroimidazo[1,2-c]quinazolin-5-yl}nicotinamide;

N-{8-[2-(dimethylamino)ethoxy]-7-methoxy-2,3-dihydroimidazo[1,2-c]quinazolin-5-yl}pyrimidine-5-carboxamide;

N-(8-{3-[2-(hydroxymethyl)morpholin-4-yl]propoxy}-7-methoxy-2,3-dihydroimidazo[1,2-c]quinazolin-5-yl)nicotinamide;

N-(8-{3-[2-(hydroxymethyl)morpholin-4-yl]propoxy}-7-methoxy-2,3-dihydroimidazo[1,2-c]quinazolin-5-yl)nicotinamide;

N-{8-[3-(dimethylamino)propoxy]-7-methoxy-2,3-dihydroimidazo[1,2-c]quinazolin-5-yl}nicotinamide 1-oxide;

2-amino-N-[7-methoxy-8-(3-morpholin-4-ylpropoxy)-2,3-dihydroimidazo[1,2-c]quinazolin-5-yl]pyrimidine-5-carboxamide;

N-[7-methoxy-8-(3-morpholin-4-ylpropoxy)-2,3-dihydroimidazo[1,2-c]quinazolin-5-yl]-6-(2-pyrrolidin-1-ylethyl)nicotinamide;

6-(cyclopentylamino)-N-[7-methoxy-8-(3-morpholin-4-ylpropoxy)-2,3-dihydroimidazo[1,2-c]quinazolin-5-yl]nicotinamide;

N-[8-(2-hydroxy-3-morpholin-4-ylpropoxy)-7-methoxy-2,3-dihydroimidazo[1,2-c]quinazolin-5-yl]nicotinamide;

N-{7-methoxy-8-[3-(3-methylmorpholin-4-yl)propoxy]-2,3-dihydroimidazo[1,2-c]quinazolin-5-yl}nicotinamide;

N-(8-{3-[2-(hydroxymethyl)morpholin-4-yl]propoxy}-7-methoxy-2,3' dihydroimidazo[1,2-c]quinazolin-5-yl)nicotinamide;

N-(8-{2-[4-(cyclobutylmethyl)morpholin-2-yl]ethoxy}-7-methoxy-2,3-dihydroimidazo[1,2-c]quinazolin-5-yl)nicotinamide;

N-(7-methoxy-8-{2-[4-(2-methoxyethyl)morpholin-2-yl]ethoxy}-2,3-dihydroimidazo[1,2-c]quinazolin-5-yl)nicotinamide;

N-{8-[(4-ethylmorpholin-2-yl)methoxy]-7-methoxy-2,3-dihydroimidazo[1,2-c]quinazolin-5-yl}nicotinamide;

N-(7-methoxy-8-{[4-(2-methoxyethyl)morpholin-2-yl]methoxy}-2,3-dihydroimidazo[1,2-c]quinazolin-5-yl)nicotinamide;

N-{7-methoxy-8-[(4-methylmorpholin-2-yl)methoxy]-2,3-dihydroimidazo[1,2-c]quinazolin-5-yl}nicotinamide;

N-[7-methoxy-8-(3-morpholin-4-ylpropoxy)-2,3-dihydroimidazo[1,2-c]quinazolin-5-yl]pyrimidine-4-carboxamide;

2-amino-N-[7-methoxy-8-(3-morpholin-4-ylpropoxy)-2,3-dihydroimidazo[1,2-c]quinazolin-5-yl]pyrimidine-4-carboxamide;

N-[7-methoxy-8-(3-morpholin-4-ylpropoxy)-2,3-dihydroimidazo[1,2-c]quinazolin-5-yl]-1-methyl-1H-imidazole-4-carboxamide;

rel-N-(8-{3-[(2R,6S)-2,6-dimethylmorpholin-4-yl]propoxy}-7-methoxy-2,3-dihydroimidazo[1,2-c]quinazolin-5-yl)pyrimidine-5-carboxamide;

rel-N-(8-{3-[(2R,6S)-2,6-dimethylmorpholin-4-yl]propoxy}-7-methoxy-2,3-dihydroimidazo[1,2-c]quinazolin-5-yl)-6-methylnicotinamide;

rel-6-acetamido-N-(8-{3-[(2R,6S)-2,6-dimethylmorpholin-4-yl]propoxy}-7-methoxy-2,3-dihydroimidazo[1,2-c]quinazolin-5-yl)nicotinamide;

N-[7-methoxy-8-(3-morpholin-4-ylpropoxy)-2,3-dihydroimidazo[1,2-c]quinazolin-5-yl]-1-methyl-1H-imidazole-5-carboxamide;

6-amino-N-[7-methoxy-8-(3-morpholin-4-ylpropoxy)-2,3-dihydroimidazo[1,2-c]quinazolin-5-yl]-2-methylnicotinamide;

2-amino-N-[7-methoxy-8-(3-morpholin-4-ylpropoxy)-2,3-dihydroimidazo[1,2-c]quinazolin-5-yl]-4-methylpyrimidine-5-carboxamide;

6-amino-5-bromo-N-[7-methoxy-8-(3-morpholin-4-ylpropoxy)-2,3-dihydroimidazo[1,2-c]quinazolin-5-yl]nicotinamide;

2-amino-N-[7-methoxy-8-(3-morpholin-4-ylpropoxy)-2,3-dihydroimidazo[1,2-c]quinazolin-5-yl]-1,3-oxazole-5-carboxamide;

N-[7-methoxy-8-(morpholin-2-ylmethoxy)-2,3-dihydroimidazo[1,2-c]quinazolin-5-yl]nicotinamide;

2-{[2-(dimethylamino)ethyl]amino}-N-{8-[3-(dimethylamino)propoxy]-7-methoxy-2,3-dihydroimidazo[1,2-c]quinazolin-5-yl}pyrimidine-5-carboxamide;

2-amino-N-{8-[3-(dimethylamino)propoxy]-7-methoxy-2,3-dihydroimidazo[1,2-c]quinazolin-5-yl}-1,3-thiazole-5-carboxamide;

rel-2-amino-N-(8-{3-[(2R,6S)-2,6-dimethylmorpholin-4-yl]propoxy}-7-methoxy-2,3-dihydroimidazo[1,2-c]quinazolin-5-yl)pyrimidine-5-carboxamide;

rel-6-amino-N-(8-{3-[(2R,6S)-2,6-dimethylmorpholin-4-yl]propoxy}-7-methoxy-2,3-dihydroimidazo[1,2-c]quinazolin-5-yl)nicotinamide;

2-[(2-hydroxyethyl)amino]-N-[7-methoxy-8-(3-morpholin-4-ylpropoxy)-2,3-dihydroimidazo[1,2-c]quinazolin-5-yl]pyrimidine-5-carboxamide;

N-[7-methoxy-8-(3-morpholin-4-ylpropoxy)-2,3-dihydroimidazo[1,2-c]quinazolin-5-yl]-2-[(3-methoxypropyl)amino]pyrimidine-5-carboxamide;

2-amino-N-{8-[3-(dimethylamino)propoxy]-7-methoxy-2,3-dihydroimidazo[1,2-c]quinazolin-5-yl}pyrimidine-5-carboxamide;

N-[7-methoxy-8-(3-morpholin-4-ylpropoxy)-2,3-dihydroimidazo[1,2-c]quinazolin-5-yl]-2-[(3-morpholin-4-ylpropyl)amino]pyrimidine-5-carboxamide;

2-[(2-methoxyethyl)amino]-N-[7-methoxy-8-(3-morpholin-4-ylpropoxy)-2,3-dihydroimidazo[1,2-c]quinazolin-5-yl]pyrimidine-5-carboxamide;

2-{[2-(dimethylamino)ethyl]amino}-N-[7-methoxy-8-(3-morpholin-4-ylpropoxy)-2,3-dihydroimidazo[1,2-c]quinazolin-5-yl]pyrimidine-5-carboxamide;

6-amino-N-{8-[3-(dimethylamino)propoxy]-7-methoxy-2,3-dihydroimidazo[1,2-c]quinazolin-5-yl}nicotinamide;

N-[7-methoxy-8-(3-morpholin-4-ylpropoxy)-2,3-dihydroimidazo[1,2-c]quinazolin-5-yl]-2-pyrrolidin-1-ylpyrimidine-5-carboxamide;

N-[7-methoxy-8-(3-morpholin-4-ylpropoxy)-2,3-dihydroimidazo[1,2-c]quinazolin-5-yl]-2-(4-methylpiperazin-1-yl)pyrimidine-5-carboxamide;

N-[7-methoxy-8-(3-morpholin-4-ylpropoxy)-2,3-dihydroimidazo[1,2-c]quinazolin-5-yl]-2-morpholin-4-ylpyrimidine-5-carboxamide;

N-[7-methoxy-8-(3-morpholin-4-ylpropoxy)-2,3-dihydroimidazo[1,2-c]quinazolin-5-yl]-6-piperazin-1-ylnicotinamide hydrochloride;

6-[(3S)-3-aminopyrrolidin-1-yl]-N-[7-methoxy-8-(3-morpholin-4-ylpropoxy)-2,3-dihydroimidazo[1,2-c]quinazolin-5-yl]nicotinamide hydrochloride hydrate;

6-[(3R)-3-aminopyrrolidin-1-yl]-N-[7-methoxy-8-(3-morpholin-4-ylpropoxy)-2,3-dihydroimidazo[1,2-c]quinazolin-5-yl]nicotinamide hydrochloride;

6-[(4-fluorobenzyl)amino]-N-[7-methoxy-8-(3-morpholin-4-ylpropoxy)-2,3-dihydroimidazo[1,2-c]quinazolin-5-yl]nicotinamide;

6-[(2-furylmethyl)amino]-N-[7-methoxy-8-(3-morpholin-4-ylpropoxy)-2,3-dihydroimidazo[1,2-c]quinazolin-5-yl]nicotinamide;

6-[(2-methoxyethyl)amino]-N-[7-methoxy-8-(3-morpholin-4-ylpropoxy)-2,3-dihydroimidazo[1,2-c]quinazolin-5-yl]nicotinamide;

N-[7-methoxy-8-(3-morpholin-4-ylpropoxy)-2,3-dihydroimidazo[1,2-c]quinazolin-5-yl]-6-(1H-pyrrol-1-yl)nicotinamide;

N-[7-methoxy-8-(3-morpholin-4-ylpropoxy)-2,3-dihydroimidazo[1,2-c]quinazolin-5-yl]-6-morpholin-4-ylnicotinamide;

N-{7-methoxy-8-[3-(methylamino)propoxy]-2,3-dihydroimidazo[1,2-c]quinazolin-5-yl}nicotinamide;

6-[(2,2-dimethylpropanoyl)amino]-N-[7-methoxy-8-(3-morpholin-4-ylpropoxy)-2,3-dihydroimidazo[1,2-c]quinazolin-5-yl]nicotinamide;

6-[(cyclopropylcarbonyl)amino]-N-[7-methoxy-8-(3-morpholin-4-ylpropoxy)-2,3-dihydroimidazo[1,2-c]quinazolin-5-yl]nicotinamide N-[7-methoxy-8-(3-morpholin-4-ylpropoxy)-2,3-dihydroimidazo[1,2-c]quinazolin-5-yl]-6-(2,2,2-trifluoroethoxy)nicotinamide;

N-[7-methoxy-8-(3-morpholin-4-ylpropoxy)-2,3-dihydroimidazo[1,2-c]quinazolin-5-yl]-6-(trifluoromethyl)nicotinamide;

6-(isobutyrylamino)-N-[7-methoxy-8-(3-morpholin-4-ylpropoxy)-2,3'dihydroimidazo[1,2-c]quinazolin-5-yl]nicotinamide;

N-{7-methoxy-8-[3-(4-methylpiperazin-1-yl)propoxy]-2,3-dihydroimidazo[1,2-c]quinazolin-5-yl}nicotinamide;

N-[7-methoxy-8-(3-morpholin-4-ylpropoxy)-2,3-dihydroimidazo[1,2-c]quinazolin-5-yl]-2-{[(methylamino)carbonyl]amino}-1,3-thiazole-4-carboxamide;
N-[7-methoxy-8-(3-morpholin-4-ylpropoxy)-2,3-dihydroimidazo[1,2-c]quinazolin-5-yl]-6-{[(methylamino)carbonyl]amino}nicotinamide;
N-[7-methoxy-8-(3-morpholin-4-ylpropoxy)-2,3-dihydroimidazo[1,2-c]quinazolin-5-yl]-2-(methylamino)-1,3-thiazole-4-carboxamide;
N-[7-methoxy-8-(2-morpholin-4-ylethoxy)-2,3-dihydroimidazo[1,2-c]quinazolin-5-yl]nicotinamide;
N-{8-[2-(dimethylamino)ethoxy]-7-methoxy-2,3-dihydroimidazo[1,2-c]quinazolin-5-yl}-2,4-dimethyl-1,3-thiazole-5-carboxamide;
N-{8-[2-(dimethylamino)ethoxy]-7-methoxy-2,3-dihydroimidazo[1,2-c]quinazolin-5-yl}-6-methylnicotinamide;
6-{[(isopropylamino)carbonyl]amino}-N-[7-methoxy-8-(3-morpholin-4-ylpropoxy)-2,3-dihydroimidazo[1,2-c]quinazolin-5-yl]nicotinamide;
N-[7-methoxy-8-(3-morpholin-4-ylpropoxy)-2,3-dihydroimidazo[1,2-c]quinazolin-5-yl]-6-pyrrolidin-1-ylnicotinamide;
6-(dimethylamino)-N-[7-methoxy-8-(3-morpholin-4-ylpropoxy)-2,3-dihydroimidazo[1,2-c]quinazolin-5-yl]nicotinamide;
N-[7-methoxy-8-(3-piperidin-1-ylpropoxy)-2,3-dihydroimidazo[1,2-c]quinazolin-5-yl]nicotinamide;
N-[7-methoxy-8-(2-pyrrolidin-1-ylethoxy)-2,3-dihydroimidazo[1,2-c]quinazolin-5-yl]nicotinamide;
N-[7-methoxy-8-(2-piperidin-1-ylethoxy)-2,3-dihydroimidazo[1,2-c]quinazolin-5-yl]nicotinamide;
6-{[(ethylamino)carbonyl]amino}-N-[7-methoxy-8-(3-morpholin-4-ylpropoxy)-2,3-dihydroimidazo[1,2-c]quinazolin-5-yl]nicotinamide;
6-fluoro-N-[7-methoxy-8-(3-morpholin-4-ylpropoxy)-2,3-dihydroimidazo[1,2-c]quinazolin-5-yl]nicotinamide;
2-amino-N-[7-methoxy-8-(3-morpholin-4-ylpropoxy)-2,3-dihydroimidazo[1,2-c]quinazolin-5-yl]-1,3-oxazole-4-carboxamide;
2-(ethylamino)-N-[7-methoxy-8-(3-morpholin-4-ylpropoxy)-2,3-dihydroimidazo[1,2-c]quinazolin-5-yl]-1,3-thiazole-4-carboxamide;
N-[7-methoxy-8-(3-morpholin-4-ylpropoxy)-2,3-dihydroimidazo[1,2-c]quinazolin-5-yl]pyrazine-2-carboxamide;
N-[8-(2-aminoethoxy)-7-methoxy-2,3-dihydroimidazo[1,2-c]quinazolin-5-yl]nicotinamide;
6-amino-N'[7-methoxy-8-(3-morpholin-4-ylpropoxy)-2,3-dihydroimidazo[1,2-c]quinazolin-5-yl]nicotinamide;
N-[7-methoxy-8-(3-morpholin-4-ylpropoxy)-2,3-dihydroimidazo[1,2-c]quinazolin-5-yl]isonicotinamide;
N-{8-[3-(diethylamino)propoxy]-7-methoxy-2,3-dihydroimidazo[1,2-c]quinazolin-5-yl}nicotinamide;
N-{8-[2-(diisopropylamino)ethoxy]-7-methoxy-2,3-dihydroimidazo[1,2-c]quinazolin-5-yl}nicotinamide;
N-{8-[2-(diethylamino)ethoxy]-7-methoxy-2,3-dihydroimidazo[1,2-c]quinazolin-5-yl}nicotinamide;
N-{8-[3-(dimethylamino)propoxy]-7-methoxy-2,3-dihydroimidazo[1,2-c]quinazolin-5-yl}nicotinamide;
N-{8-[2-(dimethylamino)ethoxy]-7-methoxy-2,3-dihydroimidazo[1,2-c]quinazolin-5-yl}nicotinamide;
N-[7-methoxy-8-(3-morpholin-4-ylpropoxy)-2,3-dihydroimidazo[1,2-c]quinazolin-5-yl]-2-(methylamino)pyrimidine-5-carboxamide;
N-[7-methoxy-8-(3-morpholin-4-ylpropoxy)-2,3-dihydroimidazo[1,2-c]quinazolin-5-yl]-2-(methylthio)pyrimidine-5-carboxamide;
N-[8-(3-aminopropoxy)-7-methoxy-2,3-dihydroimidazo[1,2-c]quinazolin-5-yl]nicotinamide trifluoroacetate;
N-[7-methoxy-8-(3-morpholin-4-ylpropoxy)-2,3-dihydroimidazo[1,2-c]quinazolin-5-yl]thiophene-2-carboxamide;
N-[7-methoxy-8-(3-morpholin-4-ylpropoxy)-2,3-dihydroimidazo[1,2-c]quinazolin-5-yl]-2,4-dimethyl-1,3-thiazole-5-carboxamide;
2-methoxy-N-[7-methoxy-8-(3-morpholin-4-ylpropoxy-2,3-dihydroimidazo[1,2-c]quinazolin-5-yl]pyrimidine-5-carboxamide;
N-[7-methoxy-8-(3-morpholin-4-ylpropoxy)-2,3-dihydroimidazo[1,2-c]quinazolin-5-yl]-3-furamide;
N-[7-methoxy-8-(3-morpholin-4-ylpropoxy)-2,3-dihydroimidazo[1,2-c]quinazolin-5-yl]thiophene-3-carboxamide;
N-[7-methoxy-8-(3-morpholin-4-ylpropoxy)-2,3-dihydroimidazo[1,2-c]quinazolin-5-yl]-2-methyl-1,3-thiazole-4-carboxamide;
6-methoxy-N-[7-methoxy-8-(3-morpholin-4-ylpropoxy-2,3-dihydroimidazo[1,2-c]quinazolin-5-yl]nicotinamide;
5-methoxy-N-[7-methoxy-8-(3-morpholin-4-ylpropoxy-2,3-dihydroimidazo[1,2-c]quinazolin-5-yl]nicotinamide;
N-[7-methoxy-8-(3-morpholin-4-ylpropoxy)-2,3-dihydroimidazo[1,2-c]quinazolin-5-yl]-6-methylnicotinamide;
6-(acetylamino)-N-[7-methoxy-8-(3-morpholin-4-ylpropoxy)-2,3-dihydroimidazo[1,2-c]quinazolin-5-yl]nicotinamide;
N-[7-methoxy-8-(3-morpholin-4-ylpropoxy)-2,3-dihydroimidazo[1,2-c]quinazolin-5-yl]nicotinamide;
or a physiologically acceptable salt, solvate, hydrate or stereoisomer thereof, as a sole active agent,
or of combinations of:
a) such a 2,3-dihydroimidazo[1,2-c]quinazoline compound, or a physiologically acceptable salt, solvate, hydrate or stereoisomer thereof; and
b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:
  PI3Kδ-selective inhibitor GS-1101, BTK inhibitor ibrutinib, IKK inhibitor BAY Compound B, and REFAMETINIB (BAY 86-9766 (RDEA-119));
or of pharmaceutical compositions containing such compounds or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a preferred embodiment, the invention encompasses the use of a compound having the formula:

N-[7-methoxy-8-(3-morpholin-4-ylpropoxy)-2,3-dihydroimidazo[1,2-c]quinazolin-5-yl]nicotinamide;
N-[7-methoxy-8-(3-morpholin-4-ylpropoxy)-2,3-dihydroimidazo[1,2-c]quinazolin-5-yl]-6-methylnicotinamide;
5-methoxy-N-[7-methoxy-8-(3-morpholin-4-ylpropoxy-2,3-dihydroimidazo[1,2-c]quinazolin-5-yl]nicotinamide;
N-[7-methoxy-8-(3-morpholin-4-ylpropoxy)-2,3-dihydroimidazo[1,2-c]quinazolin-5-yl]-2,4-dimethyl-1,3-thiazole-5-carboxamide;
N-{8-[2-(dimethylamino)ethoxy]-7-methoxy-2,3-dihydroimidazo[1,2-c]quinazolin-5-yl}nicotinamide;
N-{8-[3-(dimethylamino)propoxy]-7-methoxy-2,3-dihydroimidazo[1,2-c]quinazolin-5-yl}nicotinamide;
6-{[(isopropylamino)carbonyl]amino}-N-[7-methoxy-8-(3-morpholin-4-ylpropoxy)-2,3-dihydroimidazo[1,2-c]quinazolin-5-yl]nicotinamide;
N-{8-[2-(dimethylamino)ethoxy]-7-methoxy-2,3-dihydroimidazo[1,2-c]quinazolin-5-yl}-2,4-dimethyl-1,3-thiazole-5-carboxamide;
N-[7-methoxy-8-(2-morpholin-4-ylethoxy)-2,3-dihydroimidazo[1,2-c]quinazolin-5-yl]nicotinamide;
rel-6-amino-N-(8-{3-[(2R,6S)-2,6-dimethylmorpholin-4-yl]propoxy}-7-methoxy-2,3-dihydroimidazo[1,2-c]quinazolin-5-yl)nicotinamide;
rel-2-amino-N-(8-{3-[(2R,6S)-2,6-dimethylmorpholin-4-yl]propoxy}-7-methoxy-2,3-dihydroimidazo[1,2-c]quinazolin-5-yl)pyrimidine-5-carboxamide;
2-amino-N-[7-methoxy-8-(3-morpholin-4-ylpropoxy)-2,3-dihydroimidazo[1,2-c]quinazolin-5-yl]pyrimidine-5-carboxamide;
N-{8-[2-(dimethylamino)ethoxy]-7-methoxy-2,3-dihydroimidazo[1,2-c]quinazolin-5-yl}pyrimidine-5-carboxamide;
N-[7-methoxy-8-(3-morpholin-4-ylpropoxy)-2,3-dihydroimidazo[1,2-c]quinazolin-5-yl]pyrimidine-5-carboxamide;
or a physiologically acceptable salt, solvate, hydrate or stereoisomer thereof, as a sole active agent,
or of combinations of:
a) such a 2,3-dihydroimidazo[1,2-c]quinazoline compound, or a physiologically acceptable salt, solvate, hydrate or stereoisomer thereof; and
b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:
PI3Kδ-selective inhibitor GS-1101, BTK inhibitor ibrutinib, IKK inhibitor BAY Compound B, and REFAMETINIB (BAY 86-9766 (RDEA-119));
or of pharmaceutical compositions containing such compounds or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a preferred embodiment, the invention encompasses the use of a compound having the formula:
2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof;
as a sole active agent,
or of pharmaceutical compositions containing such a compound or a physiologically acceptable salt, solvate, hydrate or stereoisomer thereof,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a preferred embodiment, the invention encompasses the use of a compound having the formula:
2-amino-N-[7-methoxy-8-(3-morpholin-4-ylpropoxy)-2,3-dihydroimidazo[1,2-c]quinazolin-5-yl]pyrimidine-5-carboxamide dihydrochloride;
as a sole active agent,
or of pharmaceutical compositions containing such a compound or a physiologically acceptable salt, solvate, hydrate or stereoisomer thereof,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a preferred embodiment, the invention encompasses the use of combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; and
b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:
PI3Kδ-selective inhibitor GS-1101, BTK inhibitor ibrutinib, IKK inhibitor BAY Compound B, and REFAMETINIB (BAY 86-9766 (RDEA-119));
or of pharmaceutical compositions containing such a compound or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a preferred embodiment, the invention encompasses the use of combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; and
b) a further active agent which is PI3Kδ-selective inhibitor GS-1101;
or of pharmaceutical compositions containing such a compound or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a preferred embodiment, the invention encompasses the use of combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; and
b) a further active agent which is BTK inhibitor ibrutinib;
or of pharmaceutical compositions containing such a compound or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a preferred embodiment, the invention encompasses the use of combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; and
b) a further active agent which is IKK inhibitor BAY Compound B;
or of pharmaceutical compositions containing such a compound or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a preferred embodiment, the invention encompasses the use of combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; and
b) a further active agent which is REFAMETINIB (BAY 86-9766 (RDEA-119)); or of pharmaceutical compositions containing such a compound or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a preferred embodiment, the invention encompasses the use of combinations of:
a) 2-amino-N-[7-methoxy-8-(3-morpholin-4-ylpropoxy)-2,3-dihydroimidazo[1,2-c]quinazolin-5-yl]pyrimidine-5-carboxamide dihydrochloride; and
b) a further active agent which is PI3Kδ-selective inhibitor GS-1101;
or of pharmaceutical compositions containing such a compound or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a preferred embodiment, the invention encompasses the use of combinations of:
a) 2-amino-N-[7-methoxy-8-(3-morpholin-4-ylpropoxy)-2,3-dihydroimidazo[1,2-c]quinazolin-5-yl]pyrimidine-5-carboxamide dihydrochloride; and
b) a further active agent which is BTK inhibitor ibrutinib;
or of pharmaceutical compositions containing such a compound or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a preferred embodiment, the invention encompasses the use of combinations of:
a) 2-amino-N-[7-methoxy-8-(3-morpholin-4-ylpropoxy)-2,3-dihydroimidazo[1,2-c]quinazolin-5-yl]pyrimidine-5-carboxamide dihydrochloride; and
b) a further active agent which is IKK inhibitor BAY Compound B;

or of pharmaceutical compositions containing such a compound or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In a preferred embodiment, the invention encompasses the use of combinations of:
a) 2-amino-N-[7-methoxy-8-(3-morpholin-4-ylpropoxy)-2,3-dihydroimidazo[1,2-c]quinazolin-5-yl]pyrimidine-5-carboxamide dihydrochloride; and
b) a further active agent which is REFAMETINIB (BAY 86-9766 (RDEA-119)); or of pharmaceutical compositions containing such a compound or a physiologically acceptable salt, solvate, hydrate or stereoisomer thereof,
or of pharmaceutical compositions containing such combinations,
for the preparation of a medicament for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

Where there is a discrepancy between the chemical name and the chemical structure depicted, the chemical structure depicted takes precedence over the chemical name given.

Without being bound by theory or mechanism, the compounds of the present invention display surprising activity for the inhibition of phosphatidylinositol-3-kinase and chemical and structural stability over those compounds of the prior art. It is believed that this surprising activity is based on the chemical structure of the compounds, in particular the basicity of the compounds as a result of $R^2$ being amino optionally substituted with $R^5$ and $R^{5'}$. Further, the appropriate choice of $R^3$ and $R^2$ provide the necessary activity against the appropriate isoforms to allow for activity in vivo.

In accordance a particular embodiment of any of the above aspects, or embodiments thereof, of the present invention, said cancer is non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

Definitions

The term 'alkyl' refers to a straight or branched hydrocarbon chain radical consisting solely of carbon and hydrogen atoms, containing solely of carbon and hydrogen atoms, containing no unsaturation, having from one to eight carbon atoms, and which is attached to the rest of the molecule by a single bond, such as illustratively, methyl, ethyl, n-propyl 1-methylethyl (isopropyl), n-butyl, n-pentyl, and 1,1-dimethylethyl (t-butyl).

The term "alkenyl" refers to an aliphatic hydrocarbon group containing a carbon-carbon double bond and which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, 2- and butenyl.

The term "alkynyl" refers to a straight or branched chain hydrocarbonyl radicals having at least one carbon-carbon triple bond, and having in the range of about 2 up to 12 carbon atoms (with radicals having in the range of about 2 up to 10 carbon atoms presently being preferred) e.g., ethynyl.

The term "alkoxy" denotes an alkyl group as defined herein attached via oxygen linkage to the rest of the molecule. Representative examples of those groups are methoxy and ethoxy.

The term "alkoxyakyl" denotes an alkoxy group as defined herein attached via oxygen linkage to an alkyl group which is then attached to the main structure at any carbon from alkyl group that results in the creation of a stable structure the rest of the molecule. Representative examples of those groups are —$CH_2OCH_3$, —$CH_2OC_2H_5$.

The term "cycloalkyl" denotes a non-aromatic mono or multicyclic ring system of about 3 to 12 carbon atoms such as cyclopropyl, cyclobutyl, cyclopentyl, cyclohexyl and examples of multicyclic cycloalkyl groups include perhydronapththyl, adamantyl and norbornyl groups bridged cyclic group or sprirobicyclic groups e.g sprio (4,4) non-2-yl.

The term "cycloalkylalkyl" refers to cyclic ring-containing radicals containing in the range of about 3 up to 8 carbon atoms directly attached to alkyl group which is then also attached to the main structure at any carbon from the alkyl group that results in the creation of a stable structure such as cyclopropylmethyl, cyclobuyylethyl, cyclopentylethyl.

The term "aryl" refers to aromatic radicals having in the range of 6 up to 14 carbon atoms such as phenyl, naphthyl, tetrahydronapthyl, indanyl, biphenyl.

The term "arylalkyl" refers to an aryl group as defined herein directly bonded to an alkyl group as defined herein which is then attached to the main structure at any carbon from alkyl group that results in the creation of a stable structure the rest of the molecule. e.g., —$CH_2C_6H_5$, —$C_2H_5C_6H_5$.

The term "heterocyclic ring" refers to a stable 3- to 15 membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl cinnolinyl dioxolanyl, indolizinyl, naphthyridinyl, perhydroazepinyl, phenazinyl, phenothiazinyl, phenoxazinyl, phthalazil, pyridyl, pteridinyl, purinyl, quinazolinyl, quinoxalinyl, quinolinyl, isoquinolinyl, tetrazoyl, imidazolyl tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl pyridazinyl, oxazolyl oxazolinyl oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl.

The term "heteroaryl" refers to heterocyclic ring radical as defined herein which are aromatic. The heteroaryl ring radical may be attached to the main structure at any heteroatom or carbon atom that results in the creation of a stable structure.

The heterocyclic ring radical may be attached to the main structure at any heteroatom or carbon atom that results in the creation of a stable structure.

The term "heteroarylalkyl" refers to heteroaryl ring radical as defined herein directly bonded to alkyl group. The heteroarylalkyl radical may be attached to the main structure at any carbon atom from alkyl group that results in the creation of a stable structure.

The term "heterocyclyl" refers to a heterocylic ring radical as defined herein. The heterocylyl ring radical may be attached to the main structure at any heteroatom or carbon atom that results in the creation of a stable structure.

The term "heterocyclylalkyl" refers to a heterocylic ring radical as defined herein directly bonded to alkyl group. The heterocyclylalkyl radical may be attached to the main structure at carbon atom in the alkyl group that results in the creation of a stable structure.

The term "carbonyl" refers to an oxygen atom bound to a carbon atom of the molecule by a double bond.

The term "halogen" refers to radicals of fluorine, chlorine, bromine and iodine.

Where the plural form of the word compounds, salts, polymorphs, hydrates, solvates and the like, is used herein, this is taken to mean also a single compound, salt, polymorph, isomer, hydrate, solvate or the like.

The compounds of this invention may contain one or more asymmetric centers, depending upon the location and nature of the various substituents desired. Asymmetric carbon atoms may be present in the (R) or (S) configuration, resulting in racemic mixtures in the case of a single asymmetric center, and diastereomeric mixtures in the case of multiple asymmetric centers. In certain instances, asymmetry may also be present due to restricted rotation about a given bond, for example, the central bond adjoining two substituted aromatic rings of the specified compounds. Substituents on a ring may also be present in either cis or trans form. It is intended that all such configurations (including enantiomers and diastereomers), are included within the scope of the present invention. Preferred compounds are those, which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The present invention also relates to useful forms of the compounds as disclosed herein, such as pharmaceutically acceptable salts, co-precipitates, metabolites, hydrates, solvates and prodrugs of all the compounds of examples. The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chorine salts.

Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, chloride, bromide, iodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, sulfate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, or butyl chlorides, bromides and iodides; dialkyl sulfates like dimethyl, diethyl, dibutyl sulfate, or diamyl sulfates, long chain halides such as decyl, lauryl, myristyl and strearyl chlorides, bromides and iodides, aralkyl halides like benzyl and phenethyl bromides and others.

A solvate for the purpose of this invention is a complex of a solvent and a compound of the invention in the solid state. Exemplary solvates would include, but are not limited to, complexes of a compound of the invention with ethanol or methanol. Hydrates are a specific form of solvate wherein the solvent is water.

The synthesis of the compounds listed above is described in International Patent Application No. PCT/EP2003/010377, published as WO 2004/029055 A1, and in International Patent Application No. PCT/US2007/024985, published as WO 2008/070150, both of which are hereby incorporated herein in their entirety by reference.

In accordance with another embodiment, the present invention relates to a 2,3-dihydroimidazo[1,2-c]quinazoline compound as defined herein, in particular 2-amino-N-[7- methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof, as a sole agent, for the treatment of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In accordance a particular embodiment of any of the above aspects, or embodiments thereof, of the present invention, said cancer is non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

Combination Therapies

As mentioned supra, the present invention relates to combinations of:
a) a 2,3-dihydroimidazo[1,2-c]quinazoline compound as defined supra, or a physiologically acceptable salt, solvate, hydrate or stereoisomer thereof; or pharmaceutical compositions containing such a compound or a physiologically acceptable salt, solvate, hydrate or stereoisomer thereof; and
b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:
PI3Kδ-selective inhibitor GS-1101, BTK inhibitor ibrutinib, IKK inhibitor BAY Compound B, and REFAMETINIB (BAY 86-9766 (RDEA-119)).

In a preferred embodiment, the invention encompasses combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; or pharmaceutical compositions containing such a compound or a physiologically acceptable salt, solvate, hydrate or stereoisomer thereof; and
b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:
PI3Kδ-selective inhibitor GS-1101, BTK inhibitor ibrutinib, IKK inhibitor BAY Compound B, and REFAMETINIB (BAY 86-9766 (RDEA-119)).

In a preferred embodiment, the invention encompasses combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; or pharmaceutical compositions containing such a compound or a physiologically acceptable salt, solvate, hydrate or stereoisomer thereof; and
b) one or more further active agents selected from the group consisting of: PI3Kδ-selective inhibitor GS-1101, BTK inhibitor ibrutinib, IKK inhibitor BAY Compound B, and REFAMETINIB (BAY 86-9766 (RDEA-119)).

In a preferred embodiment, the invention encompasses combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; or pharmaceutical compositions containing such a compound or a physiologically acceptable salt, solvate, hydrate or stereoisomer thereof; and
b) a further active agent which is PI3Kδ-selective inhibitor GS-1101.

In a preferred embodiment, the invention encompasses combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; or pharmaceutical compositions containing such a compound or a physiologically acceptable salt, solvate, hydrate or stereoisomer thereof; and
b) a further active agent which is BTK inhibitor ibrutinib.

In a preferred embodiment, the invention encompasses combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; or pharmaceutical compositions containing such a compound or a physiologically acceptable salt, solvate, hydrate or stereoisomer thereof; and
b) a further active agent which is IKK inhibitor BAY Compound B.

In a preferred embodiment, the invention encompasses combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; or pharmaceutical compositions containing such a compound or a physiologically acceptable salt, solvate, hydrate or stereoisomer thereof; and
b) a further active agent which is REFAMETINIB (BAY 86-9766 (RDEA-119)).

In a preferred embodiment, the invention encompasses the use of combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; or pharmaceutical compositions containing such a compound or a physiologically acceptable salt, solvate, hydrate or stereoisomer thereof; and
b) a further active agent which is PI3Kδ-selective inhibitor GS-1101.

In a preferred embodiment, the invention encompasses the use of combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; or pharmaceutical compositions containing such a compound or a physiologically acceptable salt, solvate, hydrate or stereoisomer thereof; and
b) a further active agent which is BTK inhibitor ibrutinib.

In a preferred embodiment, the invention encompasses the use of combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; or pharmaceutical compositions containing such a compound or a physiologically acceptable salt, solvate, hydrate or stereoisomer thereof; and
b) a further active agent which is IKK inhibitor BAY Compound B.

In a preferred embodiment, the invention encompasses the use of combinations of:
a) 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof; or pharmaceutical compositions containing such a compound or a physiologically acceptable salt, solvate, hydrate or stereoisomer thereof; and
b) a further active agent which is REFAMETINIB (BAY 86-9766 (RDEA-119)).

The compounds of this invention can be administered as the sole pharmaceutical agent or in combination with one or more other pharmaceutical agents (or "further active agents") where the combination causes no unacceptable adverse effects. For example, the compounds of this invention can be combined with known anti-angiogenesis, anti-hyper-proliferative, antiinflammatory, analgesic, immuno-regulatory, diuretic, antiarrhytmic, anti-hypercholesterolemia, anti-dyslipidemia, anti-diabetic or antiviral agents, and the like, as well as with admixtures and combinations thereof.

The additional pharmaceutical agent or agents (or "further active agent") can be, but are not limited to 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 1000394, refametinib (BAY 86-9766 (RDEA 119)), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, obinutuzumab, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin, or a combination thereof.

The additional pharmaceutical agent or agents (or "further active agent") can be, but are not limited to aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depo-medrol, deslorelin, dexomethasone, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, herceptin, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lapatinib, lentinan sulphate, letrozole, leucovorin, leuprolide, leuprolide acetate, lenalidomide, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, refametinib (BAY 86-9766 (RDEA 119)), raltitrexed, rebif, rhenium-186 etidronate, rituximab, roferon-A, romurtide, salagen, sandostatin, sargramostim, semustine, sizofiran, sobuzoxane, solu-medrol, sparfosic acid, stem-cell therapy, streptozocin, strontium-89 chloride, sunitinib, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, BAY 43-9006 (sorafenib), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thalidomide, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

In accordance with an embodiment, the additional pharmaceutical agent or agents (or "further active agent") is selected from the group consisting of: 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 1000394, refametinib (BAY 86-9766 (RDEA 119)), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

The additional pharmaceutical agent can also be gemcitabine, paclitaxel, cisplatin, carboplatin, sodium butyrate, 5-FU, doxirubicin, tamoxifen, etoposide, trastumazab, gefitinib, intron A, rapamycin, 17-AAG, U0126, insulin, an insulin derivative, a PPAR ligand, a sulfonylurea drug, an α-glucosidase inhibitor, a biguanide, a PTP-1B inhibitor, a DPP-IV inhibitor, a 11-beta-HSD inhibitor, GLP-1, a GLP-1 derivative, GIP, a GIP derivative, PACAP, a PACAP derivative, secretin or a secretin derivative.

Optional anti-hyper-proliferative agents which can be added to the composition include but are not limited to compounds listed on the cancer chemotherapy drug regimens in the 11$^{th}$ Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is better tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

In accordance with an embodiment, the invention relates to combinations wherein said 2,3-dihydroimidazo[1,2-c]quinazoline compound is 2-amino-N-[7-methoxy-8-(3-morpholin-4-ylpropoxy)-2,3-dihydroimidazo[1,2-c]quinazolin-5-yl]pyrimidine-5-carboxamide.

In accordance with an embodiment, the invention relates to combinations wherein said 2,3-dihydroimidazo[1,2-c]quinazoline compound is 2-amino-N-[7-methoxy-8-(3-morpholin-4-ylpropoxy)-2,3-dihydroimidazo[1,2-c]quinazolin-5-yl]pyrimidine-5-carboxamide dihydrochloride.

In accordance with an embodiment, the invention relates to combinations wherein said 2,3-dihydroimidazo[1,2-c]quinazoline compound is 2-amino-N-[7-methoxy-8-(3-morpholin-4-ylpropoxy)-2,3-dihydroimidazo[1,2-c]quinazolin-5-yl]pyrimidine-5-carboxamide and said further active agent is PI3Kδ-selective inhibitor GS-1101.

In accordance with an embodiment, the invention relates to combinations wherein said 2,3-dihydroimidazo[1,2-c]quinazoline compound is 2-amino-N-[7-methoxy-8-(3-morpholin-4-ylpropoxy)-2,3-dihydroimidazo[1,2-c]quinazolin-5-yl]pyrimidine-5-carboxamide and said further active agent is BTK inhibitor ibrutinib.

In accordance with an embodiment, the invention relates to combinations wherein said 2,3-dihydroimidazo[1,2-c]quinazoline compound is 2-amino-N-[7-methoxy-8-(3-morpholin-4-ylpropoxy)-2,3-dihydroimidazo[1,2-c]quinazolin-5-yl]pyrimidine-5-carboxamide and said further active agent is REFAMETINIB (BAY 86-9766 (RDEA-119)).

In accordance with an embodiment, the invention relates to combinations wherein said 2,3-dihydroimidazo[1,2-c]quinazoline compound is 2-amino-N-[7-methoxy-8-(3-morpholin-4-ylpropoxy)-2,3-dihydroimidazo[1,2-c]quinazolin-5-yl]pyrimidine-5-carboxamide dihydrochloride and said further active agent is PI3Kδ-selective inhibitor GS-1101.

In accordance with an embodiment, the invention relates to combinations wherein said 2,3-dihydroimidazo[1,2-c]quinazoline compound is 2-amino-N-[7-methoxy-8-(3-morpholin-4-ylpropoxy)-2,3-dihydroimidazo[1,2-c]quinazolin-5-yl]pyrimidine-5-carboxamide dihydrochloride and said further active agent is BTK inhibitor ibrutinib.

In accordance with an embodiment, the invention relates to combinations wherein said 2,3-dihydroimidazo[1,2-c]quinazoline compound is 2-amino-N-[7-methoxy-8-(3-morpholin-4-ylpropoxy)-2,3-dihydroimidazo[1,2-c]quinazolin-5-yl]pyrimidine-5-carboxamide dihydrochloride and said further active agent is IKK inhibitor BAY Compound B.

In accordance with an embodiment, the invention relates to combinations wherein said 2,3-dihydroimidazo[1,2-c]quinazoline compound is 2-amino-N-[7-methoxy-8-(3-morpholin-4-ylpropoxy)-2,3-dihydroimidazo[1,2-c]quinazolin-5-yl]pyrimidine-5-carboxamide dihydrochloride and said further active agent is REFAMETINIB (BAY 86-9766 (RDEA-119)).

Pharmaceutical Compositions of the Compounds of the Invention

As mentioned supra, the present invention relates to pharmaceutical compositions:

comprising a 2,3-dihydroimidazo[1,2-c]quinazoline compound, or a physiologically acceptable salt, solvate, hydrate or stereoisomer thereof, as a sole active agent, for the treatment of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL), and comprising a pharmaceutical composition which comprises a combination of:
  a) a 2,3-dihydroimidazo[1,2-c]quinazoline compound, or a physiologically acceptable salt, solvate, hydrate or stereoisomer thereof; and
  b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:
  PI3Kδ-selective inhibitor GS-1101, BTK inhibitor ibrutinib, IKK inhibitor BAY Compound B, and REFAMETINIB (BAY 86-9766 (RDEA-119)).

In accordance with another embodiment, the present invention relates to pharmaceutical compositions which comprise a 2,3-dihydroimidazo[1,2-c]quinazoline compound as defined herein, in particular 2-amino-N-[7-methoxy-8-(3-morpholin-4-ylpropoxy)-2,3-dihydroimidazo[1,2-c]quinazolin-5-yl]pyrimidine-5-carboxamide, or a physiologically acceptable salt, solvate, hydrate or stereoisomer thereof, as a sole agent, for the treatment of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In accordance with another embodiment, the present invention relates to pharmaceutical compositions which comprise 2-amino-N-[7-methoxy-8-(3-morpholin-4-yl-propoxy)-2,3-dihydroimidazo[1,2-c]quinazolin-5-yl]pyrimidine-5-carboxamide dihydrochloride, as a sole agent, for the treatment of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In accordance a particular embodiment of any of the above aspects, or embodiments thereof, of the present invention, said cancer is non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In accordance a particular embodiment of any of the above aspects, or embodiments thereof, of the present invention, said cancer is non-Hodgkin's lymphoma (NHL), particularly 1st line, 2nd line, relapsed, refractory, indolent or aggressive non-Hodgkin's lymphoma (NHL).

In accordance a particular embodiment of any of the above aspects, or embodiments thereof, of the present invention, said cancer is follicular lymphoma (FL).

In accordance a particular embodiment of any of the above aspects, or embodiments thereof, of the present invention, said cancer is chronic lymphocytic leukaemia (CLL).

In accordance a particular embodiment of any of the above aspects, or embodiments thereof, of the present invention, said cancer is marginal zone lymphoma (MZL).

In accordance a particular embodiment of any of the above aspects, or embodiments thereof, of the present invention, said cancer is diffuse large B-cell lymphoma (DLBCL).

In accordance a particular embodiment of any of the above aspects, or embodiments thereof, of the present invention, said cancer is mantle cell lymphoma (MCL).

In accordance a particular embodiment of any of the above aspects, or embodiments thereof, of the present invention, said cancer is transformed lymphoma (TL).

In accordance a particular embodiment of any of the above aspects, or embodiments thereof, of the present invention, said cancer is peripheral T-cell lymphoma (PTCL).

Said pharmaceutical compositions contain one or more compounds. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active agent so that any side effects ascribable to the carrier do not vitiate the beneficial effects of the active agent. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active agent in admixture with a dispersing or wetting agent, a suspending agent and one or more preservatives. Suitable dispersing or wetting agents and suspending agents are exemplified by those already mentioned above.

Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active agent in a vegetable oil such as, for example, *arachis* oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active agent in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon); antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to *arachis* oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac); tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, crosslinked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride); viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to I-2 mg/mL with sterile 5% dextrose and is administered as an IV infusion over about 60 minutes.

Lyophilized powder for IV administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active agent, 150 mg of lactose, 50 mg of cellulose and 6 mg of magnesium stearate.

Soft Gelatin Capsules: A mixture of active agent in a digestible oil such as soybean oil, cottonseed oil or olive oil is prepared and injected by means of a positive displacement pump into molten gelatin to form soft gelatin capsules containing 100 mg of the active agent. The capsules are washed and dried. The active agent can be dissolved in a mixture of polyethylene glycol, glycerin and sorbitol to prepare a water miscible medicine mix.

Tablets: A large number of tablets are prepared by conventional procedures so that the dosage unit is 100 mg of active agent, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active agent is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Non-Hodgkin's Lymphoma (NHL), Particularly 1st Line, 2nd Line, Relapsed, Refractory, Indolent or Aggressive Non-Hodgkin's Lymphoma (NHL), in Particular Follicular Lymphoma (FL), Chronic Lymphocytic Leukaemia (CLL), Marginal Zone Lymphoma (MZL), Diffuse Large B-Cell Lymphoma (DLBCL), Mantle Cell Lymphoma (MCL), Transformed Lymphoma (TL), or Peripheral T-Cell Lymphoma (PTCL)

The present invention also relates to a method of treating or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL), in a mammal, said method comprising administering a 2,3-dihydroimidazo[1,2-c]quinazoline compound as defined herein, or a pharmaceutical composition containing same, as a sole active agent, or administering a combination of a) said compound or a pharmaceutical composition containing said compound and b) one or more further active agents as defined herein.

In accordance a particular embodiment of any of the above aspects, or embodiments thereof, of the present invention, said cancer is non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

The embodiments of the methods of treating or prophylaxis of cancer, e.g. non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (IL), or peripheral T-cell lymphoma (PTCL), as defined supra, are as described in the embodiments of the use of the compounds/combinations, as described supra.

The present invention relates to a method for using the compounds of the present invention and compositions thereof, to treat mammalian non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL). Compounds can be utilized to inhibit, block, reduce, decrease, etc., cell proliferation and/or cell division, and/or produce apoptosis, in the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL). This method comprises administering to a mammal in need thereof, including a human, an amount of a compound or combination of this invention, or a pharmaceutically acceptable salt, isomer, polymorph, metabolite, hydrate, solvate or ester thereof; etc. which is effective for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

This disorder has been well characterized in humans, but also exists with a similar etiology in other mammals, and they can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Dose and Administration

Based upon standard laboratory techniques known to evaluate compounds useful for the treatment or prophylaxis of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL), by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of the indication. The amount of the active agent to be administered in the treatment of the condition can vary widely according to such considerations as the particular compound and dosage unit employed, the mode of administration, the period of treatment, the age and sex of the patient treated, and the nature and extent of the condition treated.

The total amount of the active agent to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1,500 mg of active agent, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Biomarkers:

Biomarkers used for patient stratification are e.g. the expression of PI3K isoforms, BTK and IKK, BCR activation, BCR downstream activation of NFκB pathway, c-Myc, EZH2, for predicting the sensitivity and/or resistance of a cancer patient to said compound, thus providing rationale-based synergistic combination as defined herein to overcome the resistance.

Compounds Used

Throughout the whole of this text, including in the Examples which follow:

1. "compound of formula I" refers to 2-amino-N-[7-methoxy-8-(3-morpholin-4-ylpropoxy)-2,3-dihydroimidazo[1,2-c]quinazolin-5-yl]pyrimidine-5-carboxamide, of structure:

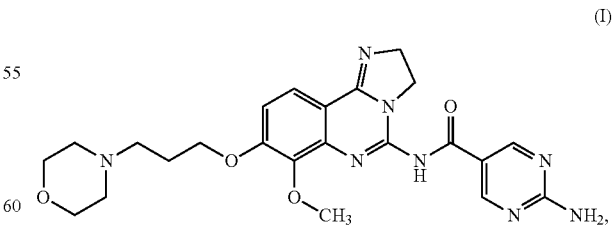

(I)

or a solvate, hydrate or stereoisomer thereof.

2. "compound A" refers to 2-amino-N-[7-methoxy-8-(3-morpholin-4-ylpropoxy)-2,3-dihydroimidazo[1,2-c]quinazolin-5-yl]pyrimidine-5-carboxamide dihydrochloride, of structure:

(A)

or a solvate, hydrate or stereoisomer thereof.

The synthesis of compound A is described in European patent application number EP 11 161 111.7, and in PCT application number PCT/EP2012/055600 published under WO 2012/136553, both of which are hereby incorporated herein in their entirety by reference.

Synthesis of Compound A:

To a suspension of the compound of formula I (400 g) in water (1.1 L) at room temperature was added a 32% aqueous 32% (aqueous) hydrochloric acid solution is with stirring dosed at room temperature to a suspension of 400 g of the compound of formula (I) in 1.1 L water until a pH of 3-4 is was reached. Additional 90 mL water (90 mL) and 32% hydrochloric acid are were added until a pH of 1.8 to 2.0 is was attained. E160 mL ethanol (160 mL) are dosed into was added to the mixture, followed by seed crystals. After stirring for 30 minutes, 1740 g additional ethanol (2.2 L) are dosed within 5 h was added into the mixture over 5 h, which is and the resulting mixture was subsequently stirred for 1 h. The suspension is filtered and the residue is washed first with a mixture of 130 g water and 215 g ethanol, secondly with a mixture of 80 g water and 255 g ethanol and then with 320 g pure ethanol. The filter cake is dried at 40° C. under vacuum to yield 457 g product (99% of theory).

Characterization of Compound A:

The chemical structure of compound A has been confirmed using the described methods of structural analysis.

IR and Raman Spectroscope
Apparatus and Measuring Conditions

| FT-IR/FT-Raman-Spectrometer | Bruker IFS 66 v/Bruker RFS 100 |
| --- | --- |
| Spectral resolution | 2 cm$^{-1}$/2 cm$^{-1}$ |
| Number of interferograms | 32/64 |
| Wave number range | 4000-500 cm$^{-1}$/3500-100 cm$^{-1}$ |
| Laser power | -/350 mW |
| Sample preparation | KBr pellet/solid in test tube |

Assignment of the Characteristic Bands

Table: Assignment of the characteristic active vibrations to the spectrum with v=stretching vibrations; δ=bending vibrations; o.o.p.=out of plane.

| Assigned Structure | IR Band position [cm$^{-1}$] | Raman Band position [cm$^{-1}$] |
| --- | --- | --- |
| v N—H | 3336 | — |
| v =C—H | 3176 | 3090 |
| v C—H | 2942 | 2990-2963 |
| v NH$^+$ | 2687-2474 | — |
| v Amide I | 1669 | 1664 |
| v C=C, v C=N, δ N—H, Amide II | 1618-1477 | 1619-1476 |
| v C—O | 1285 | 1291 |
| δ =C—H o.o.p. | 812 | — | v = stretching vibrations; δ = bending vibrations; o.o.p. = out of plane

Figure 7:
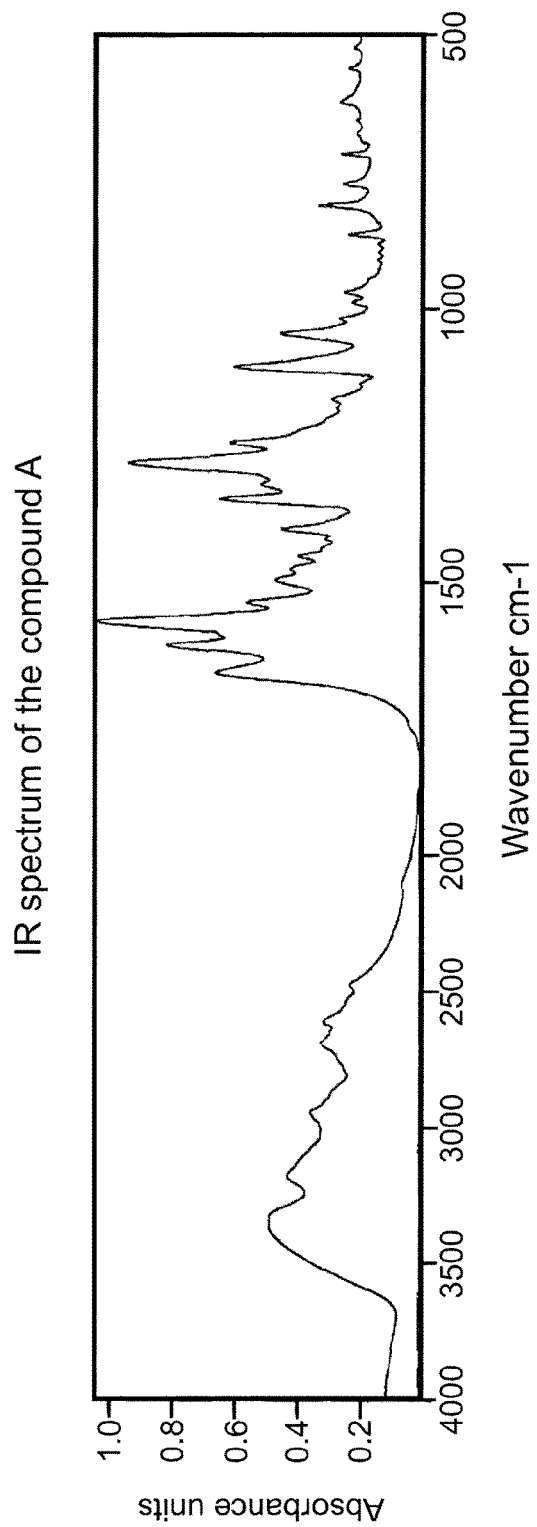
FIG. 7 shows an IR spectrum of COMPOUND A.
Figure 8:
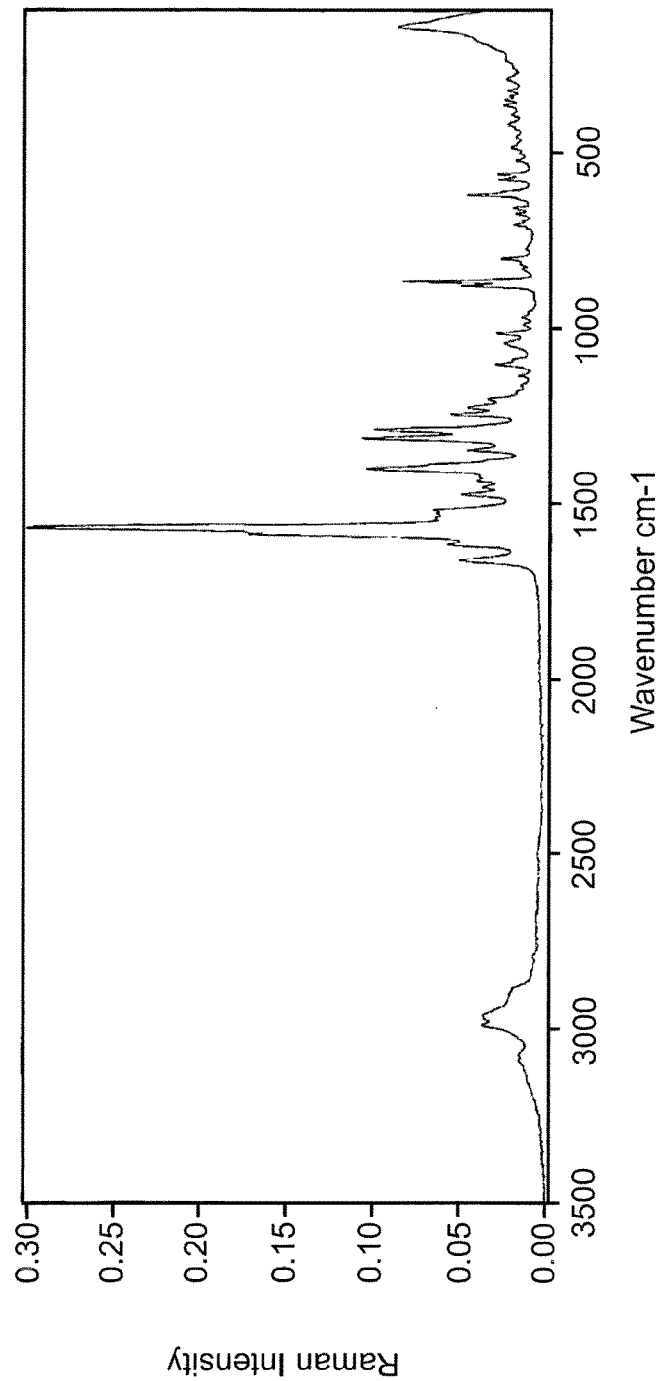
FIG. 8 shows a Raman spectrum COMPOUND A.

The IR spectrum is given in FIG. 7.
The Raman spectrum is given in FIG. 8.

UV/VIS Spectroscopy
Apparatus and Measuring Conditions

| UV/VIS spectrometer | Varian Cary 4 |
| --- | --- |
| Cuvette | Quartz, 1 cm |
| Wave number range | 200-800 nm |
| Sample preparation | 4.67 mg/500 mL water |
| Bands | 309 nm |

Figure 9:
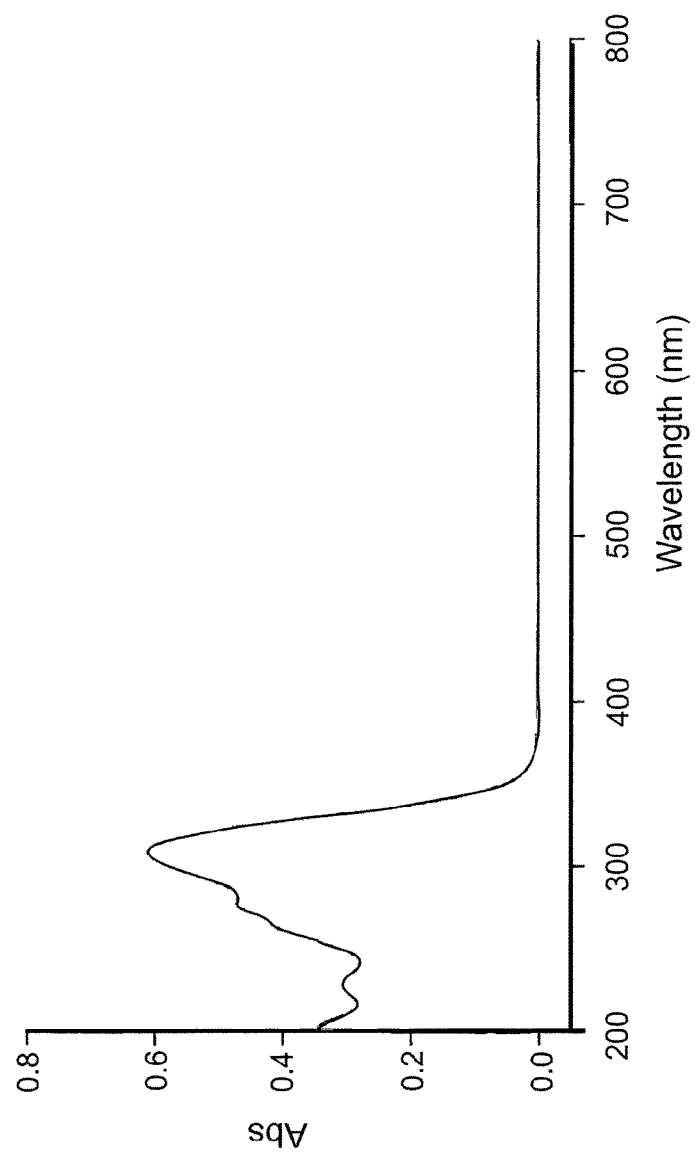
FIG. 9 shows a UV/VIS spectrum of COMPOUND A.

The UV/vis spectrum is given in FIG. 9.

NMR Spectroscopy
$^1$H-NMR-Spectroscopy
Equipment and Experimental Parameters:

| NMR spectrometer | Bruker, model Avance |
| --- | --- |
| Working frequency | 500.13 MHz |
| Solvent | Dimethylsulfoxide (DMSO-d6) |
| Internal reference compound | Tetramethylsilane (TMS) |
| Concentration | 3.08 mg/mL solution |
| Diameter of sample tube | 5 mm |
| Temperature | approx. 25° C. |
| Technique | Fourier transform mode |
| Spectral width | 20.65 ppm |
| Digital resolution | 0.079 Hz/Pt |
| Pulse length | 4.5 μsec, 30° Pulse flip angle |
| Acquisition time | 6.34 sec |
| Relaxation time | 0.5 sec |
| No. of free induction decays | 32 |

Structural Formula for the Assignment of NMR Signals

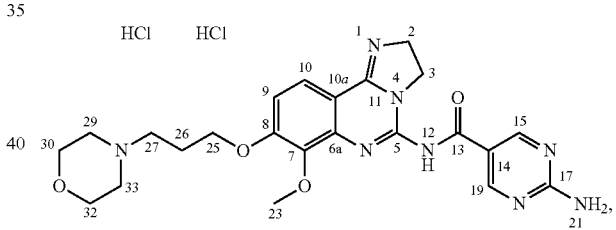

Chemical Shift, Signal Multiplicity, Relative Number of Nuclei:

| H-atoms(a) | Chemical shift δ (ppm) | Multiplicity and coupling constants(b) | no. of nuclei H/molecule |
| --- | --- | --- | --- |
| H-26 | 2.32 | M | 2 |
| H-29; H-33 | 3.11; 3.48 | M; M | 2; 2 |
| H-30; H-32 | 3.83; 3.98 | M; M | 2; 2 |
| H-27 | 3.29 | M | 2 |
| —OCH$_3$ | 4.00 | S | 3 |
| H-25 | 4.37 | T | 2 |
| H-2; H-3 | 4.47; 4.19 | T; T | 2; 2 |
| H-9 | 7.39 | D | 1 |
| NH$_2$ | 7.54 | S | 2 |
| H-10 | 8.21 | D | 1 |
| H-16; H-20 | 8.97 | S | 1; 1 |
| HCl | 11.1; 12.6 | bS; bS | 1; 1 |
| H-12 | 13.4 | bS | 1 |

Figure 10:
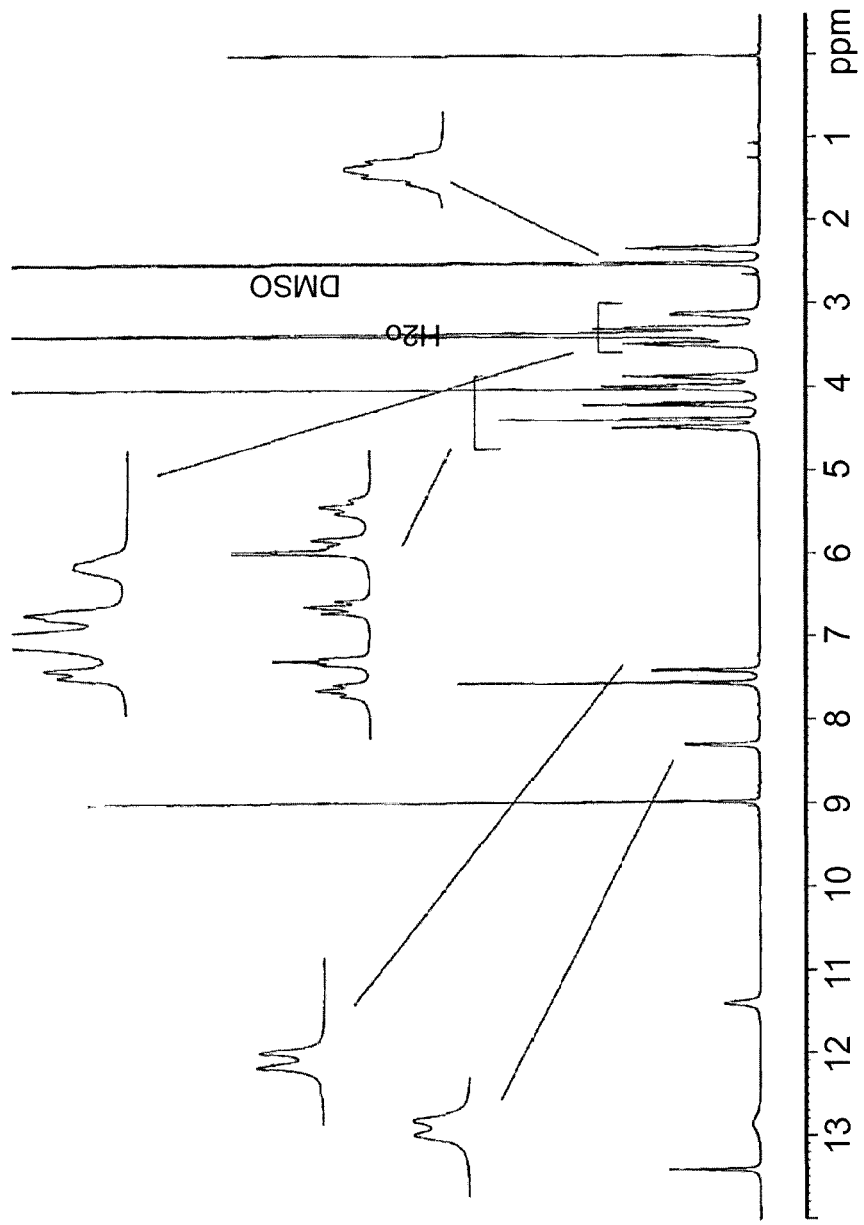
FIG. 10 shows a $^1$H-NMR spectrum of COMPOUND A.

(a)Numbering refers to the structural formula for the assignment of NMR-signals.
(b)S = Singlet bS = broad Singlet D = Doublet T = Triplet M = Multiplet The $^1$H-NMR Spectrum of compound A is given in FIG. 10.

13C-NMR-Spectroscopy

Equipment and Experimental Parameters

| | |
|---|---|
| NMR spectrometer | Bruker, model Avance |
| Working frequency | 125.76 MHz |
| Solvent | Dimethylsulfoxide-$d_6$ (DMSO) |
| Internal reference compound | Tetramethylsilane (TMS) |
| Concentration | 37.2 mg/mL solution |
| Diameter of sample tube | 5 mm |
| Temperature | approx. 27° C. |
| Technique | Fourier transform mode |
| Spectral width | 240.95 ppm |
| Digital resolution | 0.4624 Hz/Pt |
| Pulse length | 11.0 μsec, 90° Pulse flip angle |
| Acquisition time | 1.08 sec |
| Relaxation time | 4 sec |
| No. of free induction decays | 256 |

Chemical Shift, Signal Multiplicity, Rel. No. of Nuclei:

| C-atoms(a) | Chemical shift δ (ppm) | Multiplicity and coupling constants(b) | no. of nuclei C/molecule |
|---|---|---|---|
| C-26 | 22.73 | T | 1 |
| C-2; C-3 | 44.96; 45.65 | T; T | 1; 1 |
| C-29; C-33 | 50.84 | T | 1; 1 |
| C-27 | 53.01 | T | 1 |
| OCH$_3$ | 61.24 | Q | 1 |
| C-30; C-32 | 63.03 | T | 1; 1 |
| C-25 | 66.81 | T | 1 |
| C-10a | 100.79 | S | 1 |
| C-9 | 112.17 | D | 1 |
| C-15 | 118.16 | S | 1 |
| C-10 | 123.86 | D | 1 |
| C-6a | 132.43 | S | 1 |
| C-7 | 133.95 | S | 1 |
| C-5 | 148.58 | S | 1 |
| C-11 | 156.29 | S | 1 |
| C-8 | 156.89 | S | 1 |
| C-16; C-20 | 160.20 | D | 1; 1 |
| C-18 | 164.61 | S | 1 |
| C=O | 175.65 | S | 1 |

(a)Numbering refers to the structural formula for the assignment of NMR-signals.
(b)S = Single (C) D = Doublet (CH) T = Triplet (CH$_2$) Q = Quadruplet (CH$_3$)

Figure 11:
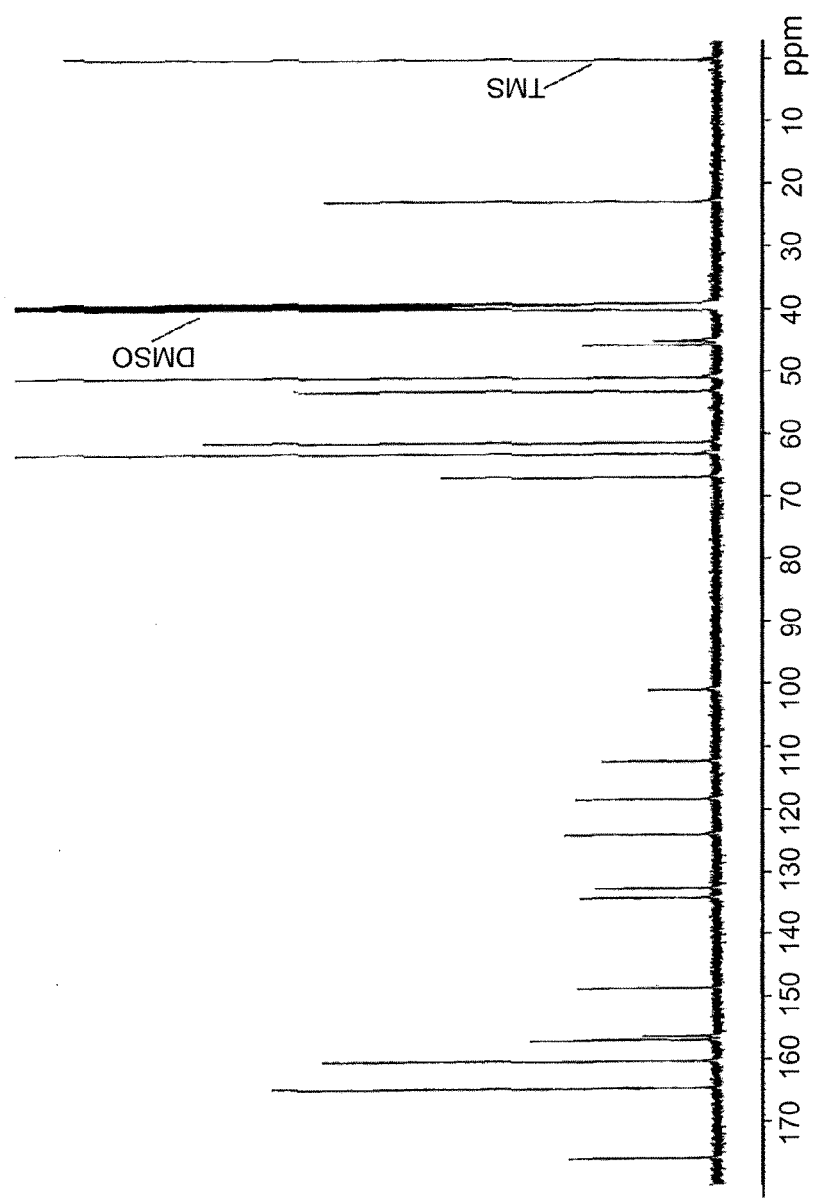
FIG. 11 shows a $^{13}$C-NMR spectrum of COMPOUND A.
Figure 12:
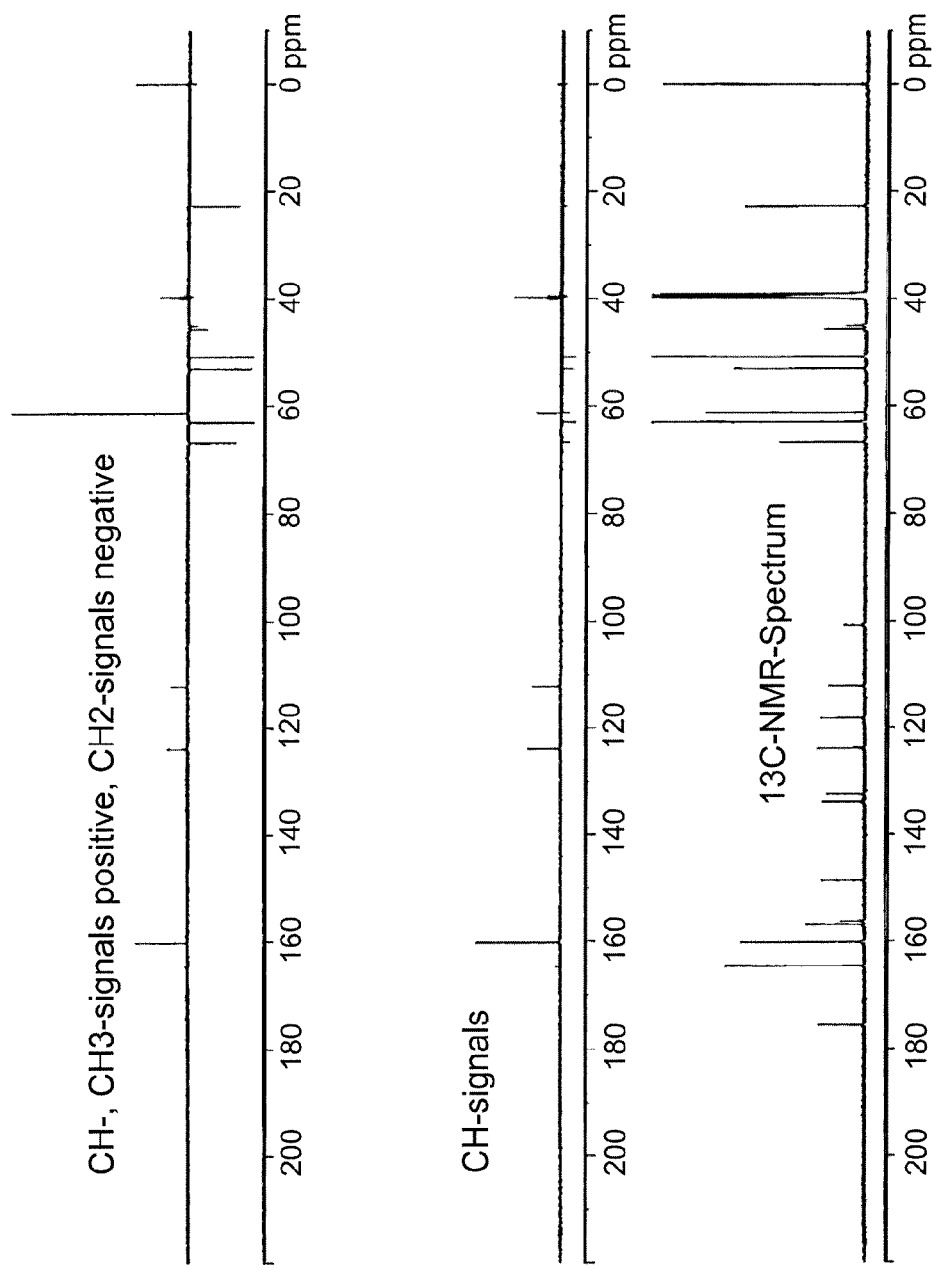
FIG. 12 shows additional $^{13}$C-NMR spectra of COMPOUND A.

The $^{13}$C-NMR Spectra of compound A are given in FIGS. 11 and 12.

Mass Spectrometry

Instrumental Parameters

| | |
|---|---|
| Mass spectrometer | Waters ZQ |
| Ionization mode | ESI (Electrospray-Ionization) |
| Solvent | CH$_3$CN/H$_2$O |

Interpretation of the Spectrum

| Mass value (m/z) | Rel. Intensity (%) | Ion Formation |
|---|---|---|
| 481.2 | 46 | (M + H)$^+$ |
| 354.1 | 5 | (C16 H16 N7 O3)$^+$ |
| 261.7 | 26 | (M + 2H + CH$_3$CN)$^{+2}$ |
| 241.2 | 100 | (M + 2H)$^{+2}$ |

Figure 13:
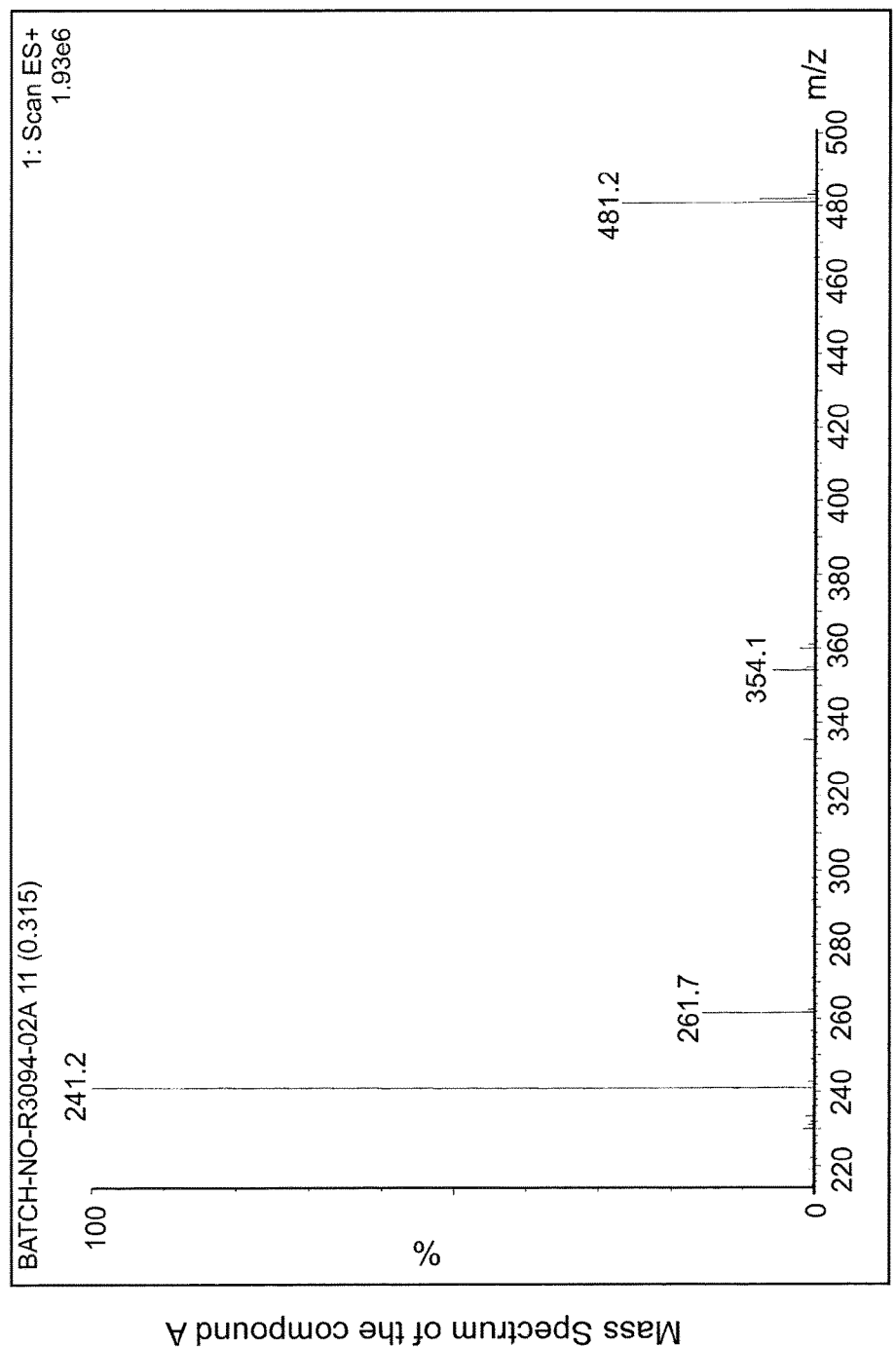
FIG. 13 shows a mass spectrum of COMPOUND A.

The Mass Spectrum of compound A is given in FIG. 13. Refer to the spectrum for relative peak intensities.

Elemental Analysis

Elemental analysis was conducted by Bayer Industry Services, Leverkusen, Germany.

Results

| Element | Measured [%] | Calculated [%] | Calculated including 7.0% water [%] | Difference |
|---|---|---|---|---|
| C | 47.5 | 49.9 | 46.4 | 1.1 |
| H | 5.7 | 5.5 | 5.9 | 0.2 |
| N | 19.1 | 20.3 | 18.8 | 0.3 |
| O | 18.1 | 11.6 | 17.0 | 1.1 |
| Cl | 11.9 | 12.8 | 11.9 | 0.0 |
| Sum | 102.3 | 100.1 | 100.0 | — |

The elemental analysis is consistent with compound A with 7% water.

Further Method of Preparation of Compound "A"

To a suspension of 366 g of compound of formula (I) in 1015 g water, 183 g of an aqueous hydrochloric acid solution (32%) were added while maintaining the temperature at 20° C.). (+−2° until a pH of 3 to 4 was reached. The resulting mixture was stirred at room temperature for more than 10 min. filtered and the filtercake washed with additional 82 g of water. The filtrate was adjusted to pH 1.8 to 2.0 using aqueous hydrochloric acid solution (32%). The mixture was stirred for 10 min. at room temperature, 146 g of ethanol (100%) were added and stirred for another 10 min. 1 g of seed crystals were added, followed by 1592 g ethanol within 5 h. The resulting substance was removed by filtration, washed with a water-ethanol mixture and dried in vacuo to give 410 g (97%) of compound A of a purity>99% according to HPLC.

2. "PI3Kδ-selective inhibitor GS-1101" refers to PI3Kδ-selective inhibitor CAL-101 (GS-1101), was purchased from ChemieTec and is of structure shown below:

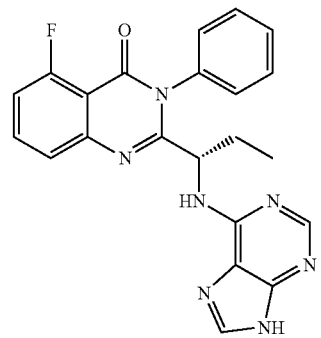

PI3Kδ-selective inhibitor
CAL-101 (GS-1101)

3. "BTK inhibitor ibrutinib" refers to the BTK inhibitor Ibrutinib (PCI32765), which was purchased from enamine and is of structure shown below:

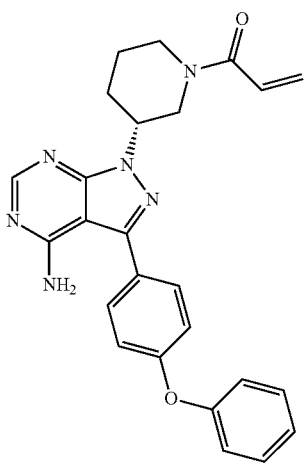 [SMILES: C=CC(=O)N1CCC[C@@H](n2nc(-c3ccc(Oc4ccccc4)cc3)c3c(N)ncnc32)C1]

4. "IKK inhibitor BAY Compound B" is the free base (−)-S-enantiomer under Example 2 of PCT application published under WO 2003/076447 and is of structure:

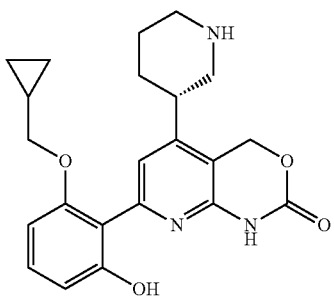 [SMILES: O=C1Nc2nc(-c3c(O)cccc3OCC3CC3)cc([C@@H]3CCCNC3)c2CO1]

EXAMPLES

The invention is demonstrated in the following examples which are not meant to limit the invention in any way:
Mutation and Protein Expression Analysis of DLBCL Cell Lines Example 1: FIG. 1 Shows Signaling Pathways Downstream of Receptors on B-Cells. (See Reference 5A)

COMPOUND A demonstrated 6/6 PR in follicular NHL with partial response observed at the end of cycle 2 at doses 0.8 mg/kg except in one case where the PR was reached at the end of cycle 4 at 0.6 mg/kg.
In contrast to PI3Kdelta-selective inhibitor GS-1101 (9/9 PD in DLBCL patients), 1/3 SD with 39% tumor reduction was observed in DLBCL patients.

Figure 2:
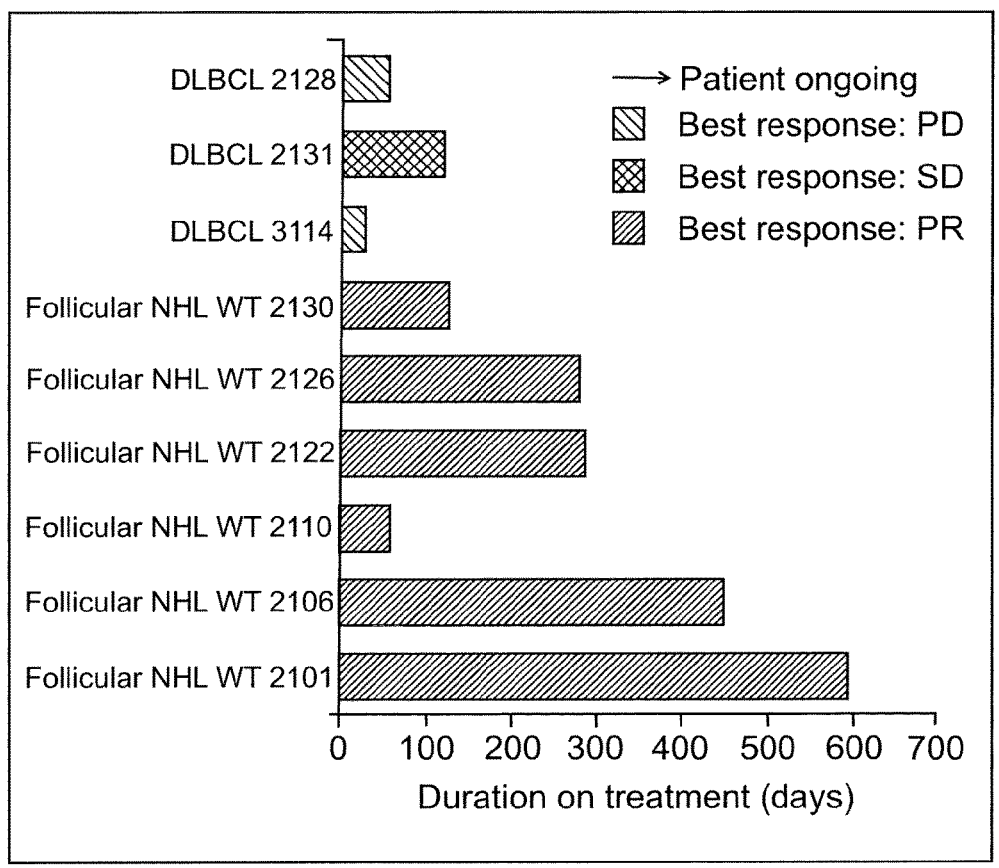
FIG. 2 shows activity of COMPOUND A in NHL patients.

Example 2: FIG. 2 Shows Activity of COMPOUND A in NHL Patients

Initial clinical efficacy of the pan-PI3K inhibitor COMPOUND A in NHL (see reference 6A) PD, progression of disease; PR, partial response; SD, stable disease; WT, wild type for PIK3CA.
COMPOUND A demonstrated 6/6 PR in follicular NHL with partial response observed at the end of cycle 2 at doses 0.8 mg/kg except in one case where the PR was reached at the end of cycle 4 at 0.6 mg/kg.
In contrast to PI3Kdelta-selective inhibitor GS-1101 (9/9 PD in DLBCL patients), 1/3 SD with 39% tumor reduction was observed in DLBCL patients.

Figure 3:
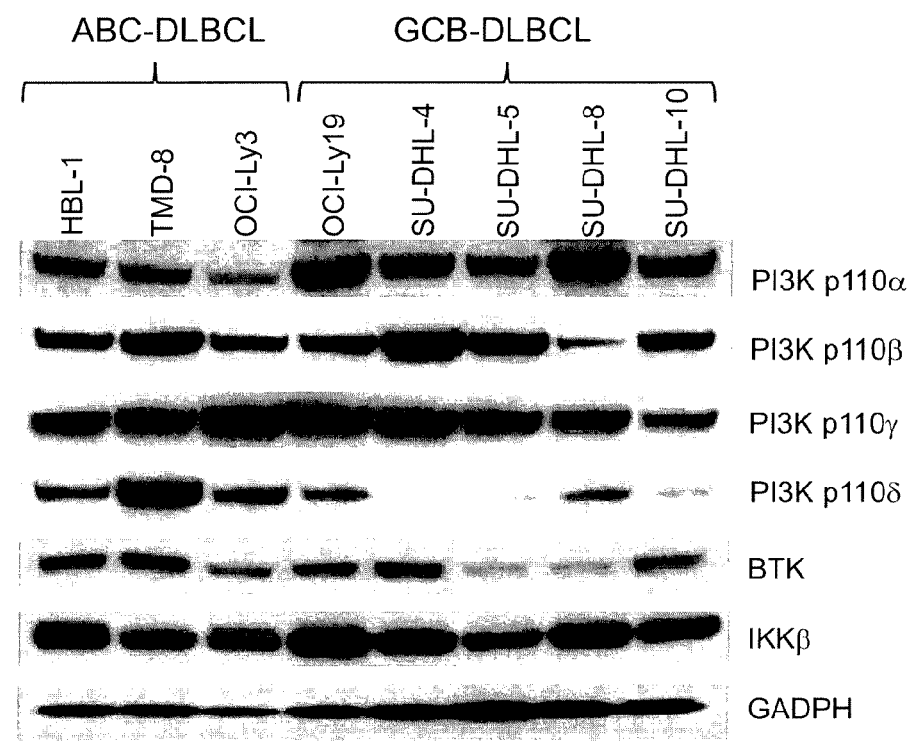
FIG. 3 shows differential expression of PI3K isoforms, BTK, and IKK in DLBCL cell lines.
Figure 4:
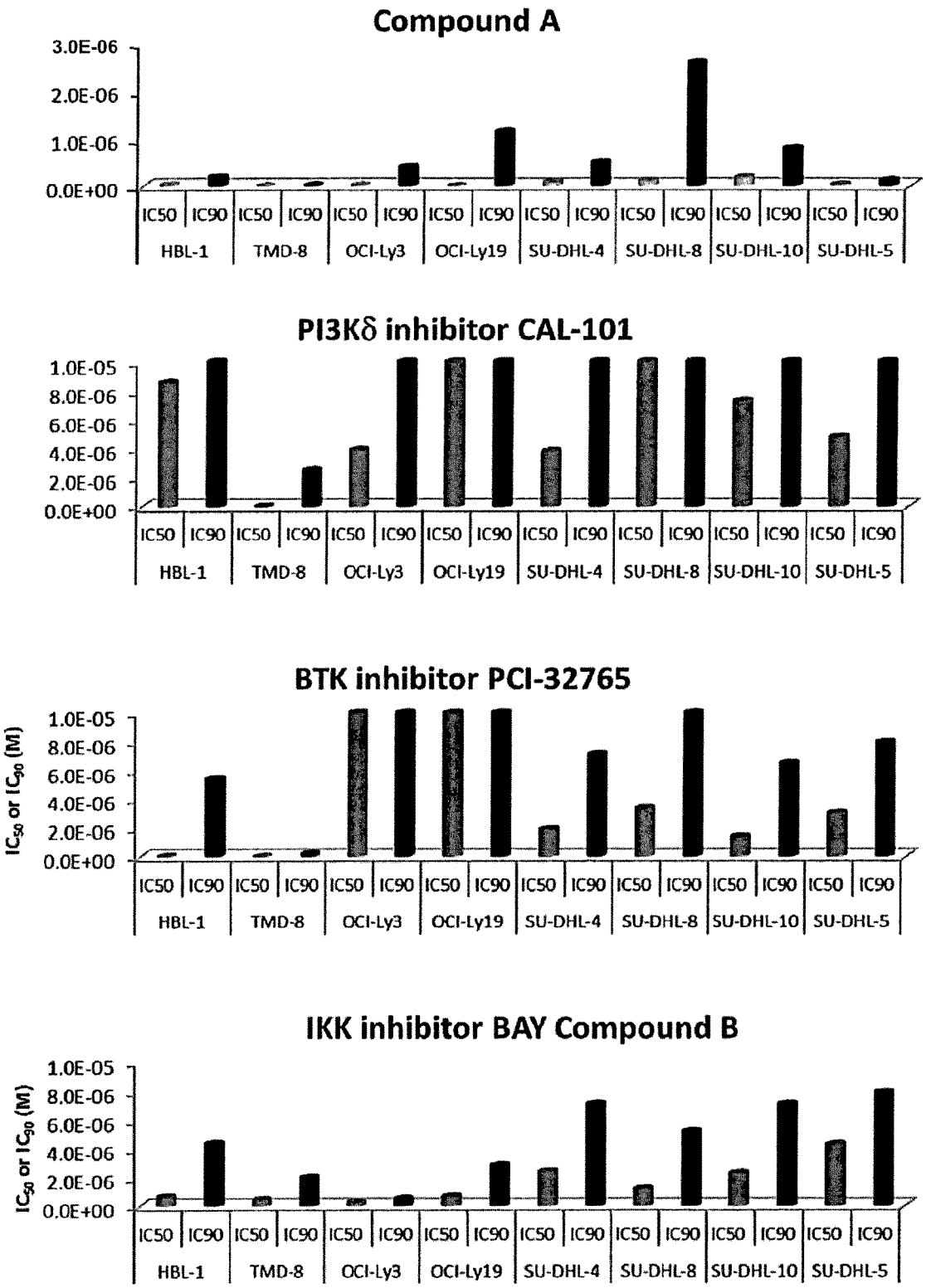
FIG. 4 shows differential anti-proliferative profile of pan-PI3K inhibitor COMPOUND A, PI3Kδ-selective inhibitor GS-1101, BTK inhibitor ibrutinib, and IKK inhibitor BAY compound B in DLBCL cells lines.

Example 3: FIG. 3 Shows Differential Expression of PI3K Isoforms, BTK, and IKK in DLBCL Cell Lines Methods:
The mutation status was obtained from public database. Protein expression was analyzed by western blot with antibodies against PI3K p110α (#4249, Cell Signaling); PI3K p110β (#3011, Cell Signaling) PI3K p110γ (#5405, Cell Signaling), PI3K p110δ (#ab1678, Abcam), BTK (#3533, Cell Signaling), IKKβ (#2370, Cell Signaling).
Conclusions
The expression of PI3Kα, PI3Kβ, and PI3Kγ isoforms was similar in all 8 DLBCL cell lines tested, while the expression of PI3Kδ varied
IKKβ was expressed across all DLBCL cell lines, while BTK was selectively expressed Example 4: Anti-Proliferative Activity of PI3K, BTK, and IKK Inhibitors in DLBCL Cell Lines FIG. 4 shows differential anti-proliferative profile of pan-PI3K inhibitor COMPOUND A, PI3Kδ-selective

TABLE 1

Genetic characteristics of DLBCL cell lines

| | ABC-DLBCL | | | GCB-DLBCL | | | | |
|---|---|---|---|---|---|---|---|---|
| Subtype Mutation | HBL-1 | TMD-8 | OCI-Ly3 | OCI-Ly19 | SU-DHL-4 | SU-DHL-5 | SU-DHL-8 | SU-DHL-10 |
| CD79 | mut | mut | WT | WT | WT | WT | WT | WT |
| MyD88 | mut | WT | mut | WT | WT | WT | WT | WT |
| CARD11 | WT | WT | mut | WT | WT | WT | WT | WT |
| EZH2 | WT | WT | WT | WT | mut | WT | WT | mut |
| Bcl2 | mut | WT | mut | Mut | mut | WT | WT | mut |
| c-Myc | WT | WT | WT | WT | WT | WT | mut | mut |

ABC, activated B-cell-like;
GCB, germinal B-cell-like;
mut, mutant inhibitor GS-1101, BTK inhibitor ibrutinib, and IKK inhibitor BAY compound B in DLBCL cell lines *>1.0E-05 (M)

Method:

Anti-proliferative effects were assessed by a 72-h Cell-Titer-Glo® assay (Promega, Cat.#G7573). Briefly, cells were plated at 250-2000 cells/well of 384-well plates (based on cell lines) in 20 µL of growth medium. For each cell line assayed, cells were plated into a separate plate for determination of luminescence at the t=0 hours and t=72 hour time points. Following overnight incubation at 37° C., luminescence values for the t=0 samples were determined by adding 20 µL of Cell Titer-Glo solution per well, transferring the plates to an orbital shaker for 10 minutes at room temperature, and then reading the plates on a Wallac Victor2 1420 Multilabel HTS Counter using the luminometry window (maximum light detection is measured at 428 nM). Dose plates for t=72 hour time points were treated with compounds diluted into growth medium in a final volume of 30 µL. Cells were then incubated for 72 hours at 37° C. Luminescence values for the t=72 hour samples were determined by adding 30 µL of Promega CellTiter-Glo solution, placing the cells on a shaker for 10 minutes at room temperature, and then reading the luminescence using a Victor luminometer. For data processing, t=0 values are subtracted from those determined for the t=72 hour time points, for both the treated and untreated samples. Percent differences in luminescence between drug treated and controls are used to determine percent inhibition of growth.

Conclusions:

Overall, the potent activity of PI3K, BTK, and IKK inhibitors in a subset of cell lines correlated with the high expression of the targets

- Pan-PI3K inhibitor COMPOUND A was particularly active in the cells with activated BCR signaling (TMD-8 and HBL-1). It was also effective in DLBCL cells with activating NFκB pathway (HBL-1 and OCI-Ly3), but required higher concentrations to reach complete tumor growth inhibition (assessed by $IC_{90}$), indicating that combination treatment might be needed to induce tumor stasis and tumor regression
- PI3Kδ-selective inhibitor GS-1101 was active only in BCR-mutant cell lines without downstream mutations. Any mutations downstream of BCR led to >100-fold decreased activity with respect to $IC_{50}$ values
- BTK inhibitor ibrutinib was active in BCR-mutant cell lines even in the presence of activating NFκB pathway ($IC_{50}$<30 nM). Cell lines without BCR-activating mutations showed a dramatically increased $IC_{50}$ value (>1 µM) or complete inactivity
- IKKβ inhibitor BAY compound B was more active in ABC-DLBCL compared with GCB-DLBCL cell lines Example 5: In Vivo Efficacy of COMPOUND a and Ibrutinib in TMD-8 Xenograft Model in CB17 Scid Mice Methods:

Untreated female 5-6 week old CB17.Scid mice are inoculated with $10\times10^6$ TMD-8 tumor cells (suspended in 50% Matrigel and 50% Medium) subcutaneously into the flank. Animals are randomized to treatment groups when tumors reach a tumor area of 30-35 mm$^2$. Treatment is conducted as described in FIG. 5 legend. Tumor area and animal body are recorded three times per week.

Conclusions:

PI3K inhibitor compound A achieved good tumor growth inhibition in the TMD-8 model upon treatment with 14 mg/kg every 2 days, reaching TGI (tumor growth inhibition) based on relative tumor area ($_{rel\ TA}$) at the end of the study of 75%. BTK inhibitor ibrutinib did also show good tumor growth inhibition in TMD-8 tumors upon treatment with 20 mg/kg once daily, reaching TGI (rel TA) of 70%. All treatments were well tolerated.

Overall, PI3K inhibitor COMPOUND A shows potent anti-tumor activity in the human ABC-DLBCL model TMD-8, comparable to BTK inhibitor ibrutinib.

Figure 5:
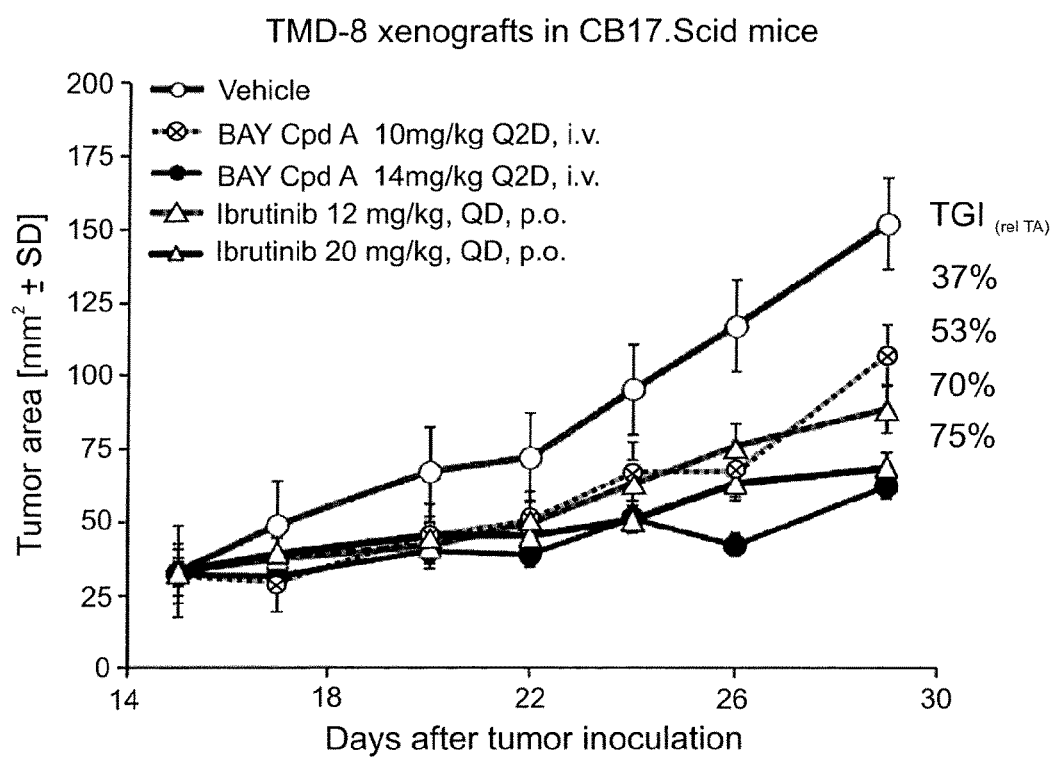
FIG. 5 shows in vivo efficacy of COMPOUND A and ibrutinib in TMD-8 xenograft model in CB17 scid mice.

See FIG. 5. Effect of COMPOUND A and ibrutinib on tumor growth in vivo. COMPOUND A was administered iv once every 2 days (Q2D) at 10 and 14 mg/kg and ibrutinib was dosed po at 12 and 20 mg/kg. Tumor growth was monitored by determination of the tumor area using caliper measurement 3 times weekly. QD, once daily; SD, standard deviation of the mean; TGI, relative tumor growth inhibition vs control (%, tumor area at the end of the study on day 29)

Example 6: Combination Effects of PI3K Inhibitor with BTK, IKK, and MEK Inhibitors in DLBCL Cells Methods:

Combination Study:

The combination effects were evaluated using combination index isobologram analysis. The efficacy parameters were the median effect in a 72-hour cell proliferation assay. Briefly, cells were plated in 384-well plate with 25 µl medium. After 24 hours, 5 µL of experimental media containing either compound A (D1), or combination partner D2 (Ibrutinib, BAY Compound B, or REFAMETINIB (BAY 86-9766 (RDEA-119))), or the combination of compound A plus D2 at different ratios (0.8×D1+0.2×D2, 0.6×D1+0.4×D2, 0.4×D1+0.6×D2, 0.2×D1+0.8×D2, 0.1×D1+0.9×D2) were used to make serial three-fold dilutions to generate 7-dose curves. Experiments were conducted in triplicates. The mapping $EC_{90}/IC_{90}$ and $EC_{90}/IC_{90}$ were calculated using Analyze5 computer program. The corresponding component doses of D1 and D2 at the $E(I)C_{50}/E(I)C_{90}$ were calculated and used for plotting isobolograms. Multiple drug effect was analyzed as described by Chou (see reference 7A) and the combination index was calculated using the formula:

Combination Index=[D1x]/D1'+[D2x]/D2'

[D1x] and [D2x] refer to the Drug 1 and Drug 2 concentration at $EC_{50}/IC_{50}$ or $EC_{90}/IC_{90}$, respectively, in combination D1' and D2' refer to the $EC_{50}/IC_{50}$ or $EC_{90}/IC_{90}$ values of D1 and D2, respectively, as a single agent. In this analysis, values less than 1.0 indicate synergistic interactions, values greater than 1.0 indicate antagonistic interactions, and values around 1.0 indicate additive interactions.

Western Blot:

Modulation of intracellular pathways were assessed by Western blots at 24 h post treatment with indicated compounds either as single agent or in combination. Antibodies used in this study are AKT (#4685, Cell Signaling), p-AKT (04060, Cell Signaling), ERK (#4695, Cell Signaling), p-ERK (#4376, Cell Signaling), BTK (#3533, Cell Signaling), p-BTK (05082, Cell Signaling), IκBα (#4812, Cell Signaling), p-IκBα (#AF4809, R&D), p-IKKα/β (02078, Cell Signaling), IKKβ (02370, Cell Signaling).

Figure 6B:
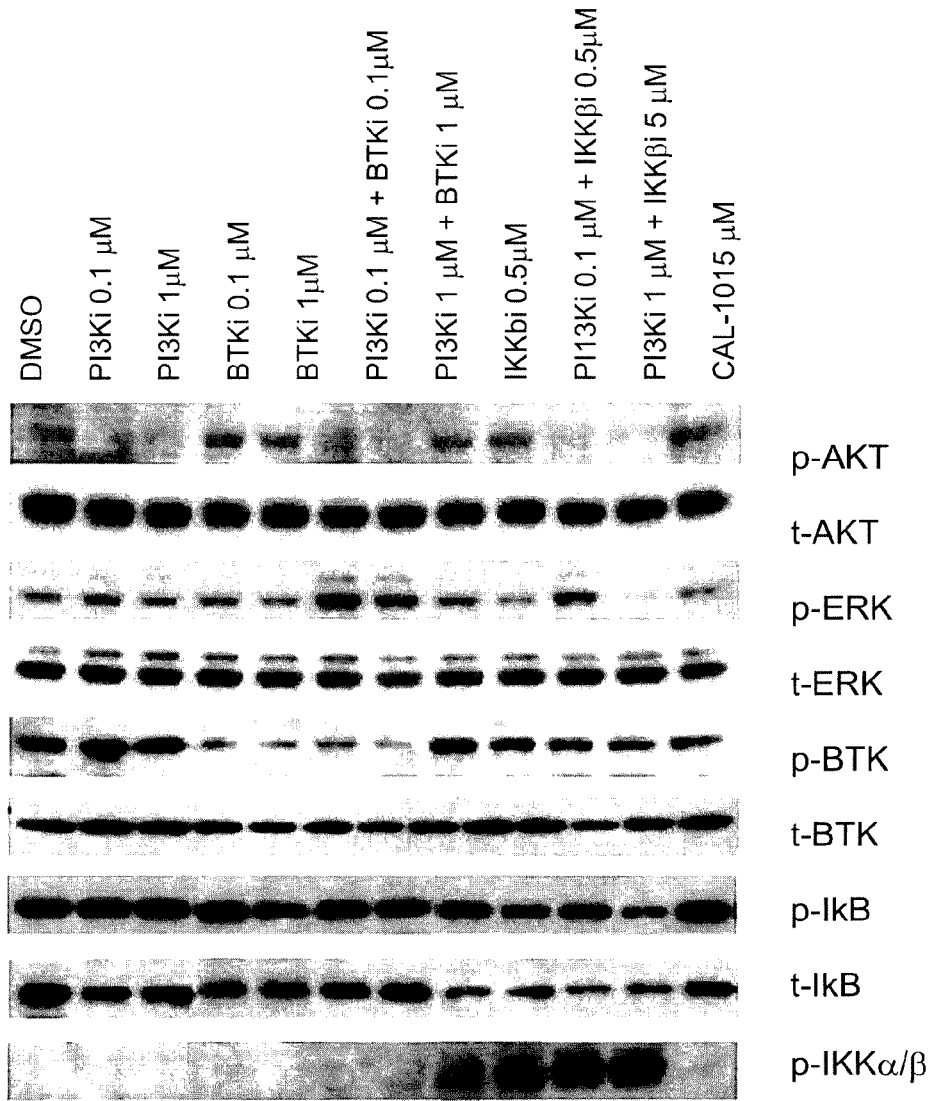
FIG. 6B shows the differential combination effects of BTK vs. IKK inhibitor investigated by analyzing the modulation of signaling pathways using Western blots with anti-phospho and anti-total target proteins in OCI-Ly3.
Figure 6C:
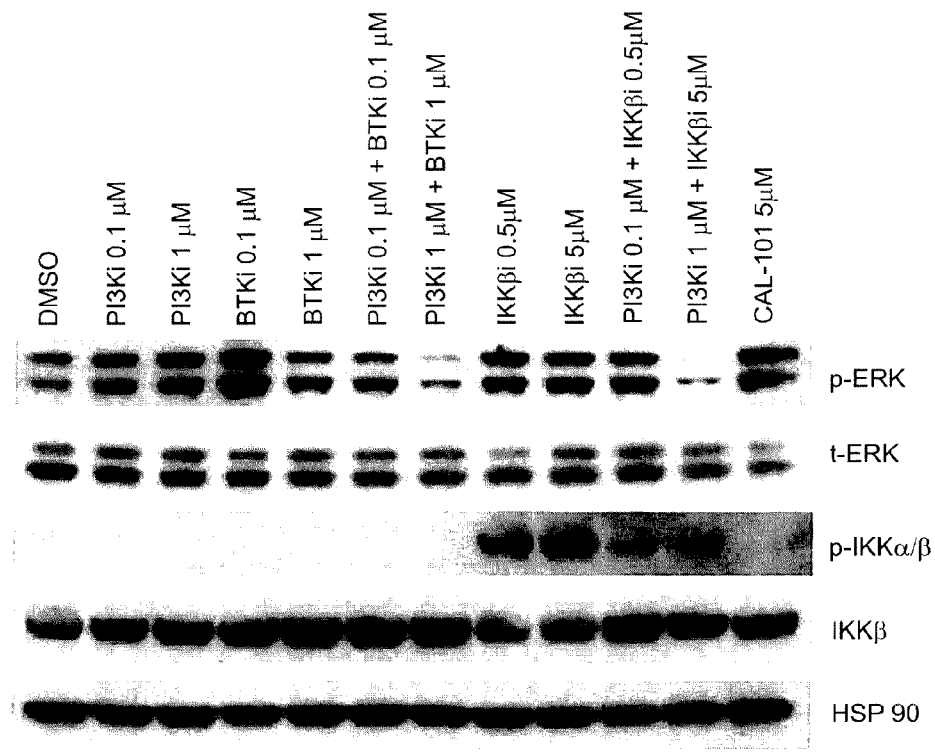
FIG. 6C shows the differential combination effects of BTK vs. IKK inhibitor investigated by analyzing the modulation of signaling pathways using Western blots with indicated anti-phospho and anti-total target proteins in HBL-1 cells.
Figure 6D:
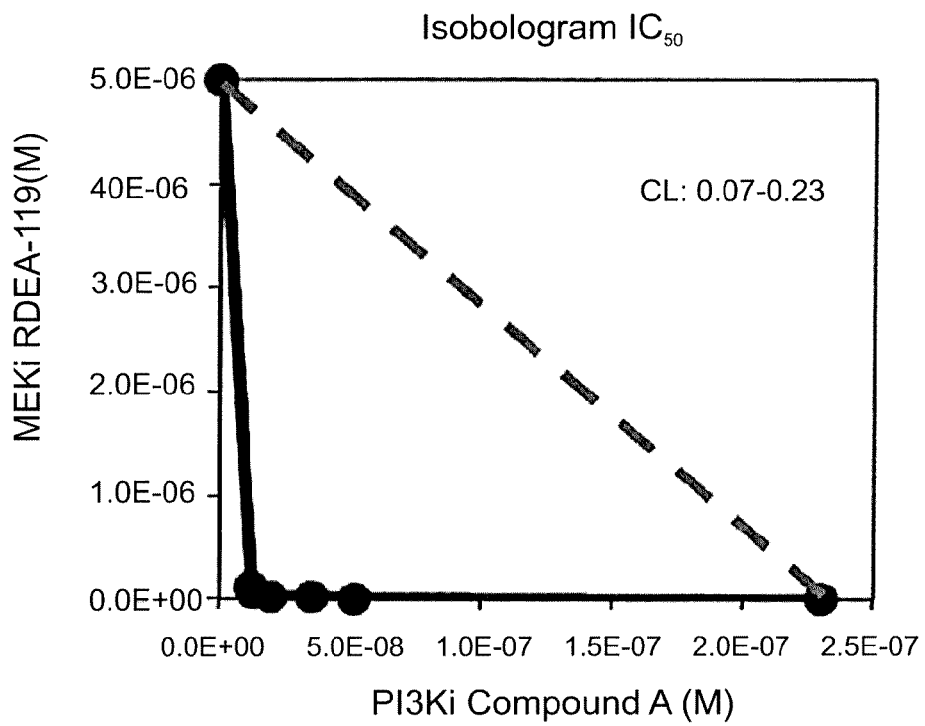
FIG. 6D shows the strong synergistic combination with MEK inhibitor REFAMETINIB (BAY 86-9766 (RDEA-119)) in MyD88- and CARD11-mutant OCI-Ly3 DLBCL cells.
Figure 6D:
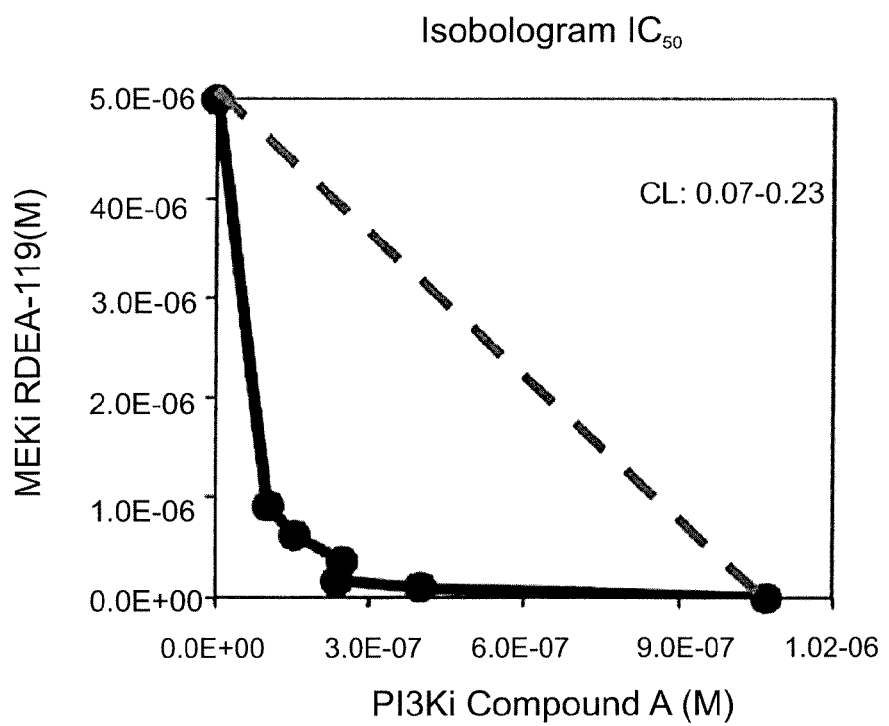

Conclusions:

Combination of pan-PI3K inhibitor compound A with BTK inhibitor ibrutinib:
- Synergistic antitumor effect observed in the tumor cell lines responding to BTK inhibition
- Antagonistic effect observed in BTK inhibitor-resistant tumor cell lines
- No synergistic effects on complete tumor growth inhibition in the cell lines with activated NFκβ pathway (MyD88 or CARD11 mutation), even in the presence of BCR activation Combination of pan-PI3K inhibitor COMPOUND A with IKK inhibitor BAY Compound B:
  Synergistic antitumor effect observed in ABC-DLBCL cells
    In GCB-DLBCL cells, the combination had both moderate synergistic and antagonistic effects
Feedback activations by inhibition of PI3Kδ, BTK, and IKK:
  Activation of p-ERK by BTK inhibitor ibrutinib in both HBL-1 and OCI-Ly3 cells
  Activation of p-IKKα/β by IKK inhibitor BAY Compound B in both HBL-1 and OCI-Ly3 cells
  Activation of p-ERK by PI3Kδ inhibitor GS-1101 in HBL-1 cells
Very strong synergistic combination with the MEK inhibitor REFAMETINIB (BAY 86-9766 (RDEA-119)) was demonstrated in MyD88- and CARD11-mutant OCI-Ly3 DLBCL cell lines FIG. 6 shows the combination effect of PI3K inhibitor compound A with BTK inhibitor ibrutinib or IKK inhibitor BAY Compound B in DLBCL cell lines FIG. 6A shows the anti-proliferative effect was investigated using a 72-h CellTiter-Glo® assay. The results were analyzed as previously described (see reference 7A). Each combination study was conducted with 5 different concentration ratios of 2 compounds and $IC_{50}$ values were determined using a series of 7-dose dilution. The differential combination effects of BTK vs IKK inhibitor were further investigated by analyzing the modulation of signaling pathways using Western blots with indicated anti-phospho and anti-total target proteins in OCI-Ly3 (FIG. 6B) and HBL-1 (FIG. 6C) cells. FIG. 6D shows the strong synergistic combination with MEK inhibitor REFAMETINIB (BAY 86-9766 (RDEA-119)) in MyD88- and CARD11-mutant OCI-Ly3 DLBCL cells CI, combination index; NA, not achievable at a concentration of 10 μM of the 2 compounds.

Example 7: Phase II Study of Single Agent COMPOUND OF FORMULA I in Patients with 1st Line, 2nd Line, Relapsed, Refractory, Indolent or Aggressive Lymphoma A phase I dose-escalation study (Patnaik et al, ASH 2012) established the maximum tolerated dose of COMPOUND OF FORMULA I (0.8 mg/kg) and reported promising activity (6/6 PR) in follicular lymphoma. In the present study we further investigated the activity and safety of COMPOUND OF FORMULA I in patients with indolent or aggressive lymphoma subtypes that have progressed after standard therapy.

In this Phase II study, patients with histologically confirmed indolent or aggressive lymphoma relapsed or refractory to ≥2 prior lines of treatment were eligible. Patients received COMPOUND OF FORMULA I at a dose of 0.8 mg/kg as a 1 hour infusion on days 1, 8 and 15 of a 28-day cycle. Patients continued on therapy until disease progression or unacceptable toxicity. Responses were assessed every two cycles according to the response criteria for lymphoma (Cheson et al, *JCO* 17:1244, 1999) or the guidelines for diagnosis and treatment of chronic lymphocytic leukemia (CLL; Hallek et al., *Blood* 111:5446-56, 2008).

Results:
As of May 31, 2013, a total of 61 lymphoma patients (27 indolent and 34 aggressive) were enrolled and 56 started study treatment. Patients were similarly distributed among indolent and aggressive cohorts with respect to gender (52% female), median age (68 yr, range 22-90) and ethnicity (76% Caucasian) and were heavily pretreated (median number of prior therapies: 3; prior Rituximab: 84%; prior ASCT: 20%). Other characteristics included advanced stage III-IV in 85% and B symptoms in 17%. The following entities were represented: follicular (FL; n=13); CLL (n=11); marginal zone (MZL; n=3; none re-staged); diffuse large B-cell (DLBCL; n=17); mantle cell (MCL; n=7); transformed (n=5); and peripheral T-cell (PTCL; n=4). At the time of analysis patients had received between 1 and 5 cycles of treatment. Objective responses were seen across histologic subtypes (Table 1). At the time of this interim analysis, the overall response rate (RR) and complete RR were 44% and 22% in FL, 83% and 17% in MCL, and 50% and 0% in PTCL, respectively.

TABLE 1

Best response by lymphoma subtype in staged patients

| | FL (n = 9) | CLL (n = 9) | DLBCL (n = 17) | MCL (n = 6) | Transformed (n = 5) | PTCL (n = 4) |
|---|---|---|---|---|---|---|
| CR/CRu | 2 | 0 | 0 | 1 | 0 | 0 |
| PR | 2 | 4 | 2 | 4 | 1 | 2 |
| SD | 5 | 4 | 7 | 0 | 2 | 0 |
| PD | 0 | 1 | 8 | 1 | 2 | 2 |

CR—complete response;
CRu—CR unconfirmed;
PR—partial response;
SD—stable disease;
PD—progressive disease Grade 3 adverse events (AE) were reported in 49% of patients, and grade 4 AE (all neutropenia) occurred in 15% of patients. Grade 3/4 AEs occurring in 5% of patients included hypertension (31%), neutropenia (16%), hyperglycemia (13%), diarrhea (5%) and fatigue (5%). Hyperglycemia of any grade occurred in 47%. Four patients required insulin therapy, but no grade 4 hyperglycemia was observed. Hypertension of any grade occurred in 46% of patients. Eight patients required antihypertensive treatment, but no grade 4 hypertension was reported. Diarrhea of any grade occurred in 25% of cases. No case of colitis was reported. There were two cases of interstitial pneumonitis, with both cases resolved following corticosteroid administration. Withdrawal of study drug due to AEs occurred in 10 patients (16%), and 4 patients required a dose reduction. Four deaths occurred; 1 due to progressive disease, 1 due to acute respiratory insufficiency, 1 due to Cryptococcal meningitis and 1 due to sepsis after start of a salvage chemotherapy regimen.

Conclusions:
The novel PI3K inhibitor COMPOUND OF FORMULA I is clinically active as a single agent and appears to have an acceptable toxicity profile in 1st line, 2nd line, relapsed, refractory lymphoma. Preliminary efficacy results are encouraging, as promising activity has been observed in FL, MCL, and PTCL. The safety profile was consistent with prior studies.

SUMMARY

All 4 PI3K isoforms are expressed in a panel of 8 DLBCL cell lines
The pan-PI3K inhibitor COMPOUND A, PI3Kδ-selective inhibitor GS-1101, BTK inhibitor Ibrutinib and IKK inhibitor BAY compound B demonstrate differential profiles of anti-proliferative activity Broader and greater antitumor activity is observed with pan-PI3K inhibitor COMPOUND A compared with PI3Kδ-selective inhibitor GS-1101, BTK inhibitor ibrutinib, and IKK inhibitor BAY compound B COMPOUND A administered iv Q2D ($T_{1/2}$~1 h in mice) at 14 mg/kg demonstrated marked antitumor activity comparable to Ibrutinib in CD79 mutant TMD-8 DLBCL xenograft model A cell-specific synergistic effect was observed for COMPOUND A in combination with an IKK inhibitor, BTK inhibitor, and MEK inhibitor BAY 86-9766

Potential biomarkers to be considered for both monotherapy and combination therapy:
Target expression
BCR activation
BCR downstream activation of NFκB pathway
c-Myc, EZH2

Further studies may reveal more effective combination partners for COMPOUND A

These findings provide a retionale to develop personalized therapies for the treatment of non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

Hence, as mentioned supra, the present invention relates to the use of biomarkers involved in the modification of the expression of PI3K isoforms, BTK and IKK, BCR activation, BCR downstream activation of NFκB pathway, c-Myc, EZH2, for predicting the sensitivity and/or resistance of a patient with non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL), to a 2,3-dihydroimidazo[1,2-c]quinazoline compound as defined herein, thus providing retionale-based synergistic combination as defined herein to overcome the resistance.

In accordance with an embodiment, the present invention relates to the use of biomarkers involved in the modification of the expression of PI3K isoforms, BTK and IKK, BCR activation, BCR downstream activation of NFκB pathway, c-Myc, EZH2, for predicting the sensitivity and/or resistance of a patient with non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (IL), or peripheral T-cell lymphoma (PTCL), to a 2,3-dihydroimidazo[1,2-c]quinazoline compound as defined herein, thus providing a rationale-based synergistic combination as defined herein to overcome the resistance (patient stratification).

In accordance with an embodiment, the present invention relates to a method of determining the level of a component of one or more of the expression of PI3K isoforms, BIK and IKK, BCR activation, BCR downstream activation of NFκB pathway, c-Myc, EZH2.

Further, as mentioned supra, the present invention thus relates to combinations of:

a) a 2,3-dihydroimidazo[1,2-c]quinazoline compound as defined supra, or a physiologically acceptable salt, solvate, hydrate or stereoisomer thereof; or pharmaceutical compositions containing such a compound or a physiologically acceptable salt, solvate, hydrate or stereoisomer thereof;
and
b) one or more further active agents, in particular an active agent selected from an anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agent, more particularly one or more further active agents selected from the group consisting of:

PI3Kδ-selective inhibitor GS-1101, BTK inhibitor ibrutinib, IKK inhibitor BAY Compound B, and REFAMETINIB (BAY 86-9766 (RDEA-119)), as defined supra.

In accordance a particular embodiment of any of the above aspects, or embodiments thereof, of the present invention, said cancer is non-Hodgkin's lymphoma (NHL), particularly 1st line, 2nd line, relapsed, refractory, indolent or aggressive non-Hodgkin's lymphoma (NHL), in particular follicular lymphoma (FL), chronic lymphocytic leukaemia (CLL), marginal zone lymphoma (MZL), diffuse large B-cell lymphoma (DLBCL), mantle cell lymphoma (MCL), transformed lymphoma (TL), or peripheral T-cell lymphoma (PTCL).

In accordance a particular embodiment of any of the above aspects, or embodiments thereof, of the present invention, said cancer is non-Hodgkin's lymphoma (NHL), particularly 1st line, 2nd line, relapsed, refractory, indolent or aggressive non-Hodgkin's lymphoma (NHL).

In accordance a particular embodiment of any of the above aspects, or embodiments thereof, of the present invention, said cancer is follicular lymphoma (FL).

In accordance a particular embodiment of any of the above aspects, or embodiments thereof, of the present invention, said cancer is chronic lymphocytic leukaemia (CLL).

In accordance a particular embodiment of any of the above aspects, or embodiments thereof, of the present invention, said cancer is marginal zone lymphoma (MZL).

In accordance a particular embodiment of any of the above aspects, or embodiments thereof, of the present invention, said cancer is diffuse large B-cell lymphoma (DLBCL).

In accordance a particular embodiment of any of the above aspects, or embodiments thereof, of the present invention, said cancer is mantle cell lymphoma (MCL).

In accordance a particular embodiment of any of the above aspects, or embodiments thereof, of the present invention, said cancer is transformed lymphoma (TL).

In accordance a particular embodiment of any of the above aspects, or embodiments thereof, of the present invention, said cancer is peripheral T-cell lymphoma (PTCL).

REFERENCES

1. Abbosh, P. H.; Nephew, K. P. Multiple signaling pathways converge on b-catenin in thyroid cancer. Thyroid 2005, 15, 551-561.
2. Ali, I. U.; Schriml, L. M.; Dean, M. Mutational spectra of PTEN/MMAC1 gene: a tumor suppressor with lipid phosphatase activity. J. Natl. Cancer Inst. 1999, 91, 1922-1932.
3. Bachman, K. E.; Argani, P.; Samuels, Y.; Silliman, N.; Ptak, J.; Szabo, S.; Konishi, H.; Karakas, B.; Blair, B. G.; Lin, C.; Peters, B. A.; Velculescu, V. E.; Park, B. H. The PIK3CA gene is mutated with high frequency in human breast cancers. Cancer Biol. Therap. 2004, 3, 772-775.
4. Bader, A. G.; Kang, S.; Vogt, P. K. Cancer-specific mutations in PIK3CA are oncogenic in vivo. Proc. Natl. Acad. Sci. U.S.A 2006, 103, 1475-1479.
5. Barthwal, M. K.; Sathyanarayana, P.; Kundu, C. N.; Rana, B.; Pradeep, A.; Sharma, C.; Woodgett, J. R.; Rana, A. Negative Regulation of Mixed Lineage Kinase 3 by Protein Kinase B/AKT Leads to Cell Survival. J. Biol. Chem. 2003, 278, 3897-3902.
6. Bénistant, C.; Chapuis, H.; Roche, S. A specific function for phosphatidylinositol 3-kinase a (p85a-p110a) in cell survival and for phosphatidylinositol 3-kinase b (p85a-p110b) in de novo DNA synthesis of human colon carcinoma cells. Oncogene 2000, 19, 5083-5090.
7. Broderick, D. K.; Di, C.; Parrett, T. J.; Samuels, Y. R.; Cummins, J. M.; McLendon, R. E.; Fults, D. W.; Velculescu, V. E.; Bigner, D. D.; Yan, H. Mutations of PIK3CA in anaplastic oligodendrogliomas, high-grade astrocytomas, and medulloblastomas. Cancer Res. 2004, 64, 5048-5050.
8. Brown, R. A.; Shepherd, P. R. Growth factor regulation of the novel class II phosphoinositide 3-kinases. Biochem. Soc. Trans. 2001, 29, 535-537.
9. Brunet, A.; Bonni, A.; Zigmond, M. J.; Lin, M. Z.; Juo, P.; Hu, L. S.; Anderson, M. J.; Arden, K. C.; Blenis, J.; Greenberg, M. E. Akt promotes cell survival by phosphorylating and inhibiting a Forkhead transcription factor. Cell 1999, 96, 857-868.
10. Byun, D.-S.; Cho, K.; Ryu, B.-K.; Lee, M.-G.; Park, J.-I.; Chae, K.-S.; Kim, H.-J.; Chi, S.-G. Frequent monoallelic deletion of PTEN and its reciprocal association with PIK3CA amplification in gastric carcinoma. Int. J. Cancer 2003, 104, 318-327.
11. Campbell, I. G.; Russell, S. E.; Choong, D. Y. H.; Montgomery, K. G.; Ciavarella, M. L.; Hooi, C. S. F.; Cristiano, B. E.; Pearson, R. B.; Phillips, W. A. Mutation of the PIK3CA gene in ovarian and breast cancer. Cancer Res. 2004, 64, 7678-7681.
12. Cardone, M. H.; Roy, N.; Stennicke, H. R.; Salvesen, G. S.; Franke, T. F.; Stanbridge, E.; Frisch, S.; Reed, J. C. Regulation of cell death protease caspase-9 by phosphorylation. Science 1998, 282, 1318-1321.
13. Chen, Y. L.; Law, P.-Y.; Loh, H. H. Inhibition of PI3K/Akt signaling: An emerging paradigm for targeted cancer therapy. Curr. Med. Chem. Anticancer Agents 2005, 5, 575-589.
14. Ciechomska, I.; Pyrzynska, B.; Kazmierczak, P.; Kaminska, B. Inhibition of Akt kinase signaling and activation of Forkhead are indispensable for up-regulation of FasL expression in apoptosis of glioma cells. Oncogene 2003, 22, 7617-7627.
15. Cross, D. A. E.; Alessi, D. R.; Cohen, P.; Andjelkovich, M.; Hemmings, B. A. Inhibition of glycogen synthase kinase-3 by insulin mediated by protein kinase B. Nature 1995, 378, 785-9.
16. Cully, M.; You, H.; Levine, A. J.; Mak, T. W. Beyond PTEN mutations: the PI3K pathway as an integrator of multiple inputs during tumorigenesis. Nat. Rev. Cancer 2006, 6, 184-192.
17. Czauderna, F.; Fechtner, M.; Aygun, H.; Arnold, W.; Klippel, A.; Giese, K.; Kaufmann, J. Functional studies of the PI(3)-kinase signaling pathway employing synthetic and expressed siRNA. Nucleic Acids Res. 2003, 31, 670-682.
18. del Peso, L.; González-Garcia, M.; Page, C.; Herrera, R.; Nunez, G. Interleukin-3-induced phosphorylation of BAD through the protein kinase Akt. Science 1997, 278, 687-689.
19. Diehl, J. A.; Cheng, M.; Roussel, M. F.; Sherr, C. J. Glycogen synthase kinase-3b regulates cyclin D1 proteolysis and subcellular localization. Genes Dev. 1998, 12, 3499-3511.
20. Dijkers, P. F.; Medema, R. H.; Lammers, J.-W. J.; Koenderman, L.; Coffer, P. J. Expression of the pro-apoptotic Bcl-2 family member Bim is regulated by the Forkhead transcription factor FKHR-L1. Curr. Biol. 2000, 10, 1201-1204.
21. Domin, J.; Waterfield, M. D. Using structure to define the function of phosphoinositide 3-kinase family members. FEBS Lett. 1997, 410, 91-95.
22. Downes, C. P.; Gray, A.; Lucocq, J. M. Probing phosphoinositide functions in signaling and membrane trafficking. Trends Cell Biol. 2005, 15, 259-268.
23. Figueroa, C.; Tarras, S.; Taylor, J.; Vojtek, A. B. Akt2 negatively regulates assembly of the POSH-MLK-JNK signaling complex. J. Biol. Chem. 2003, 278, 47922-47927.
24. Fleming, I. N.; Gray, A.; Downes, C. P. Regulation of the Rac1-specific exchange factor tiam1 involves both phosphoinositide 3-kinase-dependent and -independent components. Biochem. J. 2000, 351, 173-182.
25. Funaki, M.; Katagiri, H.; Inukai, K.; Kikuchi, M.; Asano, T. Structure and function of phosphatidylinositol-3,4 kinase. Cell. Signal. 2000, 12, 135-142.
26. Gallia, G. L.; Rand, V.; Siu, I. M.; Eberhart, C. G.; James, C. D.; Marie, S. K. N.; Oba-Shinjo, S. M.; Carlotti, C. G.; Caballero, O. L.; Simpson, A. J. G.; Brock, M. V.; Massion, P. P.; Carson, B. S., Sr.; Riggins, G. J. PIK3CA gene mutations in pediatric and adult glioblastoma multiforme. Mol. Cancer Res. 2006, 4, 709-714.
27. Gershtein, E. S.; Shatskaya, V. A.; Ermilova, V. D.; Kushlinsky, N. E.; Krasil'nikov, M. A. Phosphatidylinositol 3-kinase expression in human breast cancer. Clin. Chim. Acta 1999, 287, 59-67.
28. Gottschalk, A. R.; Doan, A.; Nakamura, J. L.; Stokoe, D.; Haas-Kogan, D. A-Inhibition of phosphatidylinositol 3-kinase causes increased sensitivity to radiation through a PKB-dependent mechanism. Int. J. Radiat. Oncol. Biol. Phys. 2005, 63, 1221-1227.
29. Gupta, A. K.; Cerniglia, G. J.; Mick, R.; Ahmed, M. S.; Bakanauskas, V. J.; Muschel, R. J.; McKenna, W. G. Radiation sensitization of human cancer cells in vivo by inhibiting the activity of PI3K using LY294002. Int. J. Radiat. Oncol. Biol. Phys. 2003, 56, 846-853.
30. Haas-Kogan, D.; Shalev, N.; Wong, M.; Mills, G.; Yount, G.; Stokoe, D. Protein kinase B (PKB/Akt) activity is elevated in glioblastoma cells due to mutation of the tumor suppressor PTEN/MMAC. Curr. Biol. 1998, 8, 1195-1198.
31. Hartmann, C.; Bartels, G.; Gehlhaar, C.; Holtkamp, N.; von Deimling, A. PIK3CA mutations in glioblastoma multiforme. Acta Neuropathol. 2005, 109, 639-642.
32. Hennessy, B. T.; Smith, D. L.; Ram, P. T.; Lu, Y.; Mills, G. B. Exploiting the PI3K/AKT Pathway for Cancer Drug Discovery. Nat. Rev. Drug Disc. 2005, 4, 988-1004.
33. Hodgkinson, C. P.; Sale, E. M.; Sale, G. J. Characterization of PDK2 activity against Protein Kinase B gamma. Biochemistry 2002, 41, 10351-10359.
34. Hresko, R. C.; Murata, H.; Mueckler, M. Phosphoinositide-dependent Kinase-2 is a distinct protein kinase 35. Huang, C.; Ma, W.-Y.; Dong, Z. Requirement for phosphatidylinositol 3-kinase in epidermal growth factor-induced AP-1 transactivation and transformation in JB6 P+ cells. Mol. Cell. Biol. 1996, 16, 6427-6435.

36. Hupp, T. R.; Lane, D. P.; Ball, K. L. Strategies for manipulating the p53 pathway in the treatment of human cancer. Biochem. J. 2000, 352, 1-17.

37. Ihle, N. T.; Williams, R.; Chow, S.; Chew, W.; Berggren, M. I.; Paine-Murrieta, G.; Minion, D. J.; Halter, R. J.; Wipf, P.; Abraham, R.; Kirkpatrick, L.; Powis, G. Molecular pharmacology and antitumor activity of PX-866, a novel inhibitor of phosphoinositide-3-kinase signaling. Mol. Cancer Therap. 2004, 3, 763-772.

38. Ikenoue, T.; Kanai, F.; Hikiba, Y.; Obata, T.; Tanaka, Y.; Imamura, J.; Ohta, M.; Jazag, A.; Guleng, B.; Tateishi, K.; Asaoka, Y.; Matsumura, M.; Kawabe, T.; Omata, M. Functional analysis of PIK3CA gene mutations in human colorectal cancer. Cancer Res. 2005, 65, 4562-4567.

39. Ishii, N.; Maier, D.; Merlo, A.; Tada, M.; Sawamura, Y.; Diserens, A.-C.; Van Meir, E. G. Frequent co-alterations of TP53, p16/CDKN2A, p14ARF, PTEN tumor suppressor genes in human glioma cell lines. Brain Pathol. 1999, 9, 469-479.

40. Itoh, T.; Takenawa, T. Phosphoinositide-binding domains. Functional units for temporal and spatial regulation of intracellular signaling. Cell. Signal. 2002, 14, 733-743.

41. Janssen, J. W. G.; Schleithoff, L.; Bartram, C. R.; Schulz, A. S. An oncogenic fusion product of the phosphatidylinositol 3-kinase p85b subunit and HUMORF8, a putative deubiquitinating enzyme. Oncogene 1998, 16, 1767-1772.

42. Jimenez, C.; Jones, D. R.; Rodriguez-Viciana, P.; Gonzalez-Garcia, A.; Leonardo, E.; Wennstrom, S.; Von Kobbe, C.; Toran, J. L.; R.-Borlado, L.; Calvo, V.; Copin, S. G.; Albar, J. P.; Gaspar, M. L.; Diez, E.; Marcos, M. A. R.; Downward, J.; Martinez-A, C.; Merida, I.; Carrera, A. C. Identification and characterization of a new oncogene derived from the regulatory subunit of phosphoinositide 3-kinase. EMBO J. 1998, 17, 743-753.

43. Jucker, M.; Sudel, K.; Horn, S.; Sickel, M.; Wegner, W.; Fiedler, W.; Feldman, R. A. Expression of a mutated form of the p85a regulatory subunit of phosphatidylinositol 3-kinase in a Hodgkin's lymphoma-derived cell line (CO). Leukemia 2002, 16, 894-901.

44. Kang, S.; Bader, A. G.; Vogt, P. K. Phosphatidylinositol 3-kinase mutations identified in human cancer are oncogenic. Proc. Natl. Acad. Sci. U.S.A 2005, 102, 802-807.

45. Kang, S.; Denley, A.; Vanhaesebroeck, B.; Vogt, P. K. Oncogenic transformation induced by the p110b, -g, and -d isoforms of class I phosphoinositide 3-kinase. Proc. Natl. Acad. Sci. U.S.A 2006, 103, 1289-1294.

46. Katso, R.; Okkenhaug, K.; Ahmadi, K.; White, S.; Timms, J.; Waterfield, M. D. Cellular function of phosphoinositide 3-kinases: implications for development, immunity, homeostasis, and cancer. Annu. Rev. Cell Dev. Biol. 2001, 17, 615-675.

47. Kim, A. H.; Khursigara, G.; Sun, X.; Franke, T. F.; Chao, M. V. Akt phosphorylates and negatively regulates apoptosis signal-regulating kinase 1. Mol. Cell. Biol. 2001, 21, 893-901.

48. Kim, D.; Dan, H. C.; Park, S.; Yang, L.; Liu, Q.; Kaneko, S.; Ning, J.; He, L.; Yang, H.; Sun, M.; Nicosia, S. V.; Cheng, J. Q. AKT/PKB signaling mechanisms in cancer and chemoresistance. Front. Biosci. 2005, 10, 975-987.

49. Klippel, A.; Kavanaugh, W. M.; Pot, D.; Williams, L. T. A specific product of phosphatidylinositol 3-kinase directly activates the protein kinase Akt through its pleckstrin homology domain. Mol. Cell. Biol. 1997, 17, 338-44.

50. Kodaki, T.; Woscholski, R.; Hallberg, B.; Rodriguez-Viciana, P.; Downward, J.; Parker, P. J. The activation of phosphatidylinositol 3-kinase by Ras. Curr. Biol. 1994, 4, 798-806.

51. Kops, G. J. P. L.; De Ruiter, N. D.; De Vries-Smits, A. M. M.; Powell, D. R.; Bos, J. L.; Burgering, B. M. T. Direct control of the Forkhead transcription factor AFX by protein kinase B. Nature 1999, 398, 630-634.

52. Lee, J. T., Jr.; Steelman, L. S.; McCubrey, J. A. Phosphatidylinositol 3'-Kinase Activation Leads to Multidrug Resistance Protein-1 Expression and Subsequent Chemoresistance in Advanced Prostate Cancer Cells. Cancer Res. 2004, 64, 8397-8404.

53. Lee, J. W.; Soung, Y. H.; Kim, S. Y.; Lee, H. W.; Park, W. S.; Nam, S. W.; Kim, S. H.; Lee, J. Y.; Yoo, N. J.; Lee, S. H. PIK3CA gene is frequently mutated in breast carcinomas and hepatocellular carcinomas. Oncogene 2005, 24, 1477-1480.

54. Lemmon, M. A. Phosphoinositide recognition domains. Traffic 2003, 4, 201-213.

55. Levine, D. A.; Bogomolniy, F.; Yee, C. J.; Lash, A.; Barakat, R. R.; Borgen, P. I.; Boyd, J. Frequent Mutation of the PIK3CA Gene in Ovarian and Breast Cancers. Clin. Cancer Res. 2005, 11, 2875-2878.

56. Li, J.; Yen, C.; Liaw, D.; Podsypanina, K.; Bose, S.; Wang, S. I.; Puc, J.; Miliaresis, C.; Rodgers, L.; McCombie, R.; Bigner, S. H.; Giovanella, B. C.; Ittmann, M.; Tycko, B.; Hibshoosh, H.; Wigler, M. H.; Parsons, R. PTEN, a putative protein tyrosine phosphatase gene mutated in human brain, breast, and prostate cancer. Science 1997, 275, 1943-1947.

57. Li, V. S. W.; Wong, C. W.; Chan, T. L.; Chan, A. S. W.; Zhao, W.; Chu, K.-M.; So, S.; Chen, X.; Yuen, S. T.; Leung, S. Y. Mutations of PIK3CA in gastric adenocarcinoma. BMC Cancer 2005, 5, 29.

58. Liao, Y.; Hung, M.-C. Regulation of the activity of p38 mitogen-activated protein kinase by Akt in cancer and adenoviral protein E1A-mediated sensitization to apoptosis. Mol. Cell. Biol. 2003, 23, 6836-6848.

59. Lopez-llasaca, M.; Li, W.; Uren, A.; Yu, J.-c.; Kazlauskas, A.; Gutkind, J. S.; Heidaran, M. A. Requirement of phosphatidylinositol-3 kinase for activation of JNK/SAPKs by PDGF. Biochem. Biophys. Res. Commun. 1997, 232, 273-277.

60. Ma, Y.-Y.; Wei, S.-J.; Lin, Y.-C.; Lung, J.-C.; Chang, T.-C.; Whang-Peng, J.; Liu, J. M.; Yang, D.-M.; Yang, W. K.; Shen, C.-Y. PIK3CA as an oncogene in cervical cancer. Oncogene 2000, 19, 2739-2744.

61. Mayo, L. D.; Dixon, J. E.; Durden, D. L.; Tonks, N. K.; Donner, D. B. PTEN protects p53 from Mdm2 and sensitizes cancer cells to chemotherapy. J. Biol. Chem. 2002, 277, 5484-5489.

62. Momand, J.; Wu, H.-H.; Dasgupta, G. MDM2-master regulator of the p53 tumor suppressor protein. Gene 2000, 242, 15-29.

63. Motti, M. L.; De Marco, C.; Califano, D.; Fusco, A.; Viglietto, G. Akt-dependent T198 phosphorylation of cyclin-dependent kinase inhibitor p27kip1 in breast cancer. Cell Cycle 2004, 3, 1074-1080.

64. Myers, M. P.; Pass, I.; Batty, I. H.; Van Der Kaay, J.; Stolarov, J. P.; Hemmings, B. A.; Wigler, M. H.; Downes, C. P.; Tonks, N. K. The lipid phosphatase activity of PTEN is critical for its tumor suppressor function. Proc. Natl. Acad. Sci. U.S.A 1998, 95, 13513-13518.

65. Nagata, Y.; Lan, K.-H.; Zhou, X.; Tan, M.; Esteva, F. J.; Sahin, A. A.; Nos, K. S.; Li, P.; Monia, B. P.; Nguyen, N. T.; Hortobagyi, G. N.; Hung, M.-C.; Yu, D. PTEN activation contributes to tumor inhibition by trastuzumab, and loss of PTEN predicts trastuzumab resistance in patients. Cancer Cell 2004, 6, 117-127.

66. Naito, A. T.; Akazawa, H.; Takano, H.; Minamino, T.; Nagai, T.; Aburatani, H.; Komuro, I. Phosphatidylinositol 3-Kinase-Akt Pathway Plays a Critical Role in Early Cardiomyogenesis by Regulating Canonical Wnt Signaling. Circ. Res. 2005, 97, 144-151.

67. Oda, K.; Stokoe, D.; Taketani, Y.; McCormick, F. High Frequency of Coexistent Mutations of PIK3CA and PTEN Genes in Endometrial Carcinoma. Cancer Res. 2005, 65, 10669-10673.

68. Ogawara, Y.; Kishishita, S.; Obata, T.; Isazawa, Y.; Suzuki, T.; Tanaka, K.; Masuyama, N.; Gotoh, Y. Akt enhances Mdm2-mediated ubiquitination and degradation of p53. J. Biol. Chem. 2002, 277, 21843-21850.

69. Olson, J. M.; Hallahan, A. R. p38 MAP kinase: a convergence point in cancer therapy. Trends Mol. Med. 2004, 10, 125-129.

70. Osaki, M.; Oshimura, M.; Ito, H. PI3K-Akt pathway: Its functions and alterations in human cancer. Apoptosis 2004, 9, 667-676.

71. Pastorino, J. G.; Tafani, M.; Farber, J. L. Tumor necrosis factor induces phosphorylation and translocation of BAD through a phosphatidylinositide-3-0H kinase-dependent pathway. J. Biol. Chem. 1999, 274, 19411-19416.

72. Pendaries, C.; Tronchere, H.; Plantavid, M.; Payrastre, B. Phosphoinositide signaling disorders in human diseases. FEBS Lett. 2003, 546, 25-31.

73. Phillips, W. A.; St. Clair, F.; Munday, A. D.; Thomas, R. J. S.; Mitchell, C. A. Increased levels of phosphatidylinositol 3-kinase activity in colorectal tumors. Cancer 1998, 83, 41-47.

74. Philp, A. J.; Campbell, I. G.; Leet, C.; Vincan, E.; Rockman, S. P.; Whitehead, R. H.; Thomas, R. J. S.; Phillips, W. A. The phosphatidylinositol 3'-kinase p85a gene is an oncogene in human ovarian and colon tumors. Cancer Res. 2001, 61, 7426-7429.

75. Powis, G.; Bonjouklian, R.; Berggren, M. M.; Gallegos, A.; Abraham, R.; Ashendel, C.; Zalkow, L.; Matter, W. F.; Dodge, J. Wortmannin, a potent and selective inhibitor of phosphatidylinositol-3-kinase. Cancer Res. 1994, 54, 2419-23.

76. Pu, P.; Kang, C.; Zhang, Z.; Liu, X.; Jiang, H. Downregulation of PIK3CB by siRNA suppresses malignant glioma cell growth in vitro and in vivo. Technol. Cancer Res. Treat. 2006, 5, 271-280.

77. Rahimi, N.; Tremblay, E.; Elliott, B. Phosphatidylinositol 3-kinase activity is required for hepatocyte growth factor-induced mitogenic signals in epithelial cells. J. Biol. Chem. 1996, 271, 24850-24855.

78. Roche, S.; Downward, J.; Raynal, P.; Courtneidge, S. A. A function for phosphatidylinositol 3-kinase b (p85a-p110b) in fibroblasts during mitogenesis: requirement for insulin- and lysophosphatidic acid-mediated signal transduction. Mol. Cell. Biol. 1998, 18, 7119-7129.

79. Roche, S.; Koegl, M.; Courtneidge, S. A. The phosphatidylinositol 3-kinase a is required for DNA synthesis induced by some, but not all, growth factors. Proc. Natl. Acad. Sci. U.S.A 1994, 91, 9185-9.

80. Romashkova, J. A.; Makarov, S. S. Nf-kB is a target of Akt in anti-apoptotic PDGF signaling. Nature 1999, 401, 86-90.

81. Saal, L. H.; Holm, K.; Maurer, M.; Memeo, L.; Su, T.; Wang, X.; Yu, J. S.; Malmstroem, P.-O.; Mansukhani, M.; Enoksson, J.; Hibshoosh, H.; Borg, A.; Parsons, R. PIK3CA mutations correlate with hormone receptors, node metastasis, and ERBB2, and are mutually exclusive with PTEN loss in human breast carcinoma. Cancer Res. 2005, 65, 2554-2559.

82. Samuels, Y.; Diaz, L. A., Jr.; Schmidt-Kittler, O.; Cummins, J. M.; DeLong, L.; Cheong, I.; Rago, C.; Huso, D. L.; Lengauer, C.; Kinzler, K. W.; Vogelstein, B.; Velculescu, V. E. Mutant PIK3CA promotes cell growth and invasion of human cancer cells. Cancer Cell 2005, 7, 561-573.

83. Samuels, Y.; Ericson, K. Oncogenic PI3K and its role in cancer. Curr. Opin. Oncol. 2006, 18, 77-82.

84. Samuels, Y.; Wang, Z.; Bardelli, A.; Silliman, N.; Ptak, J.; Szabo, S.; Yan, H.; Gazdar, A.; Powell, S. M.; Riggins, G. J.; Willson, J. K. V.; Markowitz, S.; Kinder, K. W.; Vogelstein, B.; Velculescu, V. E. Brevia: High frequency of mutations of the PIK3Ca gene in human cancers. Science 2004, 304, 554.

85. Scheid, M. P.; Marignani, P. A.; Woodgett, J. R. Multiple phosphoinositide 3-kinase-dependent steps in activation of protein kinase B. Mol. Cell. Biol. 2002, 22, 6247-6260.

86. Schultz, R. M.; Merriman, R. L.; Andis, S. L.; Bonjouklian, R.; Grindey, G. B.; Rutherford, P. G.; Gallegos, A.; Massey, K.; Powis, G. In vitro and in vivo antitumor activity of the phosphatidylinositol-3-kinase inhibitor, wortmannin. Anticancer Res. 1995, 15, 1135-9.

87. Segrelles, C.; Moral, M.; Lara, M. F.; Ruiz, S.; Santos, M.; Leis, H.; Garcia-Escudero, R.; Martinez-Cruz, A. B.; Martinez-Palacio, J.; Hernandez, P.; Ballestin, C.; Paramio, J. M. Molecular determinants of Akt-induced keratinocyte transformation. Oncogene 2006, 25, 1174-1185.

88. Sekimoto, T.; Fukumoto, M.; Yoneda, Y. 14-3-3 suppresses the nuclear localization of threonine 157-phosphorylated p27Kip1. EMBO J. 2004, 23, 1934-1942.

89. Semba, S.; Itoh, N.; Ito, M.; Youssef, E. M.; Harada, M.; Moriya, T.; Kimura, W.; Yamakawa, M. Down-regulation of PIK3CG catalytic subunit of phosphatidylinositol 3-OH kinase by CpG hypermethylation in human colorectal carcinoma. Clin. Cancer Res. 2002, 8, 3824-3831.

90. Shayesteh, L.; Lu, Y.; Kuo, W.-L.; Baldocchi, R.; Godfrey, T.; Collins, C.; Pinkel, D.; Powell, B.; Mills, G. B.; Gray, J. W. PIK3CA is implicated as an oncogene in ovarian cancer. Nat. Genet. 1999, 21, 99-102.

91. Shekar, S. C.; Wu, H.; Fu, Z.; Yip, S.-C.; Nagajyothi; Cahill, S. M.; Girvin, M. E.; Backer, J. M. Mechanism of Constitutive Phosphoinositide 3-Kinase Activation by Oncogenic Mutants of the p85 Regulatory Subunit. J. Biol. Chem. 2005, 280, 27850-27855.

92. Stahl, J. M.; Cheung, M.; Sharma, A.; Trivedi, N. R.; Shanmugam, S.; Robertson, G. P. Loss of PTEN Promotes Tumor Development in Malignant Melanoma. Cancer Res. 2003, 63, 2881-2890.

93. Stambolic, V.; Suzuki, A.; De La Pompa, J. L.; Brothers, G. M.; Mirtsos, C.; Sasaki, T.; Ruland, J.; Penninger, J. M.; Siderovski, D. P.; Mak, T. W. Negative regulation of PKIVAkt-Dependent cell survival by the tumor suppressor PTEN. Cell 1998, 95, 29-39.

94. Stauffer, F.; Holzer, P.; Garcia-Echeverria, C. Blocking the PI3K/PKB pathway in tumor cells. Curr. Med. Chem. Anticancer Agents 2005, 5, 449-462.
95. Steck, P. A.; Pershouse, M. A.; Jasser, S. A.; Yung, W. K. A.; Lin, H.; Ligon, A. H.; Langford, L. A.; Baumgard, M. L.; Hattier, T.; Davis, T.; Frye, C.; Hu, R.; Swedlund, B.; Teng, D. H. F.; Tavtigian, S. V. Identification of a candidate tumor suppressor gene, MMAC1, at chromosome 10q23.3 that is mutated in multiple advanced cancers. Nat. Genet. 1997, 15, 356-362.
96. Stein, R. C.; Waterfield, M. D. Pl3-kinase inhibition: a target for drug development? Mol. Med. Today 2000, 6, 347-358.
97. Stephens, L.; Williams, R.; Hawkins, P. Phosphoinositide 3-kinases as drug targets in cancer. Curr. Opin. Pharmacol. 2005, 5, 357-365.
98. Su, J. D.; Mayo, L. D.; Donner, D. B.; Durden, D. L. PTEN and Phosphatidylinositol 3'-Kinase Inhibitors Up-Regulate p53 and Block Tumor-induced Angiogenesis: Evidence for an Effect on the Tumor and Endothelial Compartment. Cancer Res. 2003, 63, 3585-3592.
99. Tanaka, M.; Grossman, H. B. In vivo gene therapy of human bladder cancer with PTEN suppresses tumor growth, downregulates phosphorylated Akt, and increases sensitivity to doxorubicin. Gene Ther. 2003, 10, 1636-1642.
100. Tang, E. D.; Nunez, G.; Barr, F. G.; Guan, K.-L. Negative regulation of the forkhead transcription factor FKHR by Akt. J. Biol. Chem. 1999, 274, 16741-16746.
101. Taylor, V.; Wong, M.; Brandts, C.; Reilly, L.; Dean, N. M.; Cowsert, L. M.; Moodie, S.; Stokoe, D. 5' Phospholipid phosphatase SHIP-2 causes protein kinase B inactivation and cell cycle arrest in glioblastoma cells. Mol. Cell. Biol. 2000, 20, 6860-6871.
102. Toker, A. Phosphoinositides and signal transduction. Cell. Mol. Life Sci. 2002, 59, 761-779.
103. Traer, C. J.; Foster, F. M.; Abraham, S. M.; Fry, M. J. Are class II phosphoinositide 3-kinases potential targets for anticancer therapies? Bull. Cancer (Paris). 2006, 93, E53-8.
104. Vanhaesebroeck, B.; Leevers, S. J.; Ahmadi, K.; Timms, J.; Katso, R.; Driscoll, P. C.; Woscholski, R.; Parker, P. J.; Waterfield, M. D. Synthesis and function of 3-phosphorylated inositol lipids. Annu. Rev. Biochem. 2001, 70, 535-602.
105. Vanhaesebroeck, B.; Waterfield, M. D. Signaling by Distinct Classes of Phosphoinositide 3-Kinases. Exp. Cell Res. 1999, 253, 239-254.
106. Vivanco, I.; Sawyers, C. L. The phosphatidylinositol 3-Kinase-AKT pathway in human cancer. Nat. Rev. Cancer 2002, 2, 489-501.
107. Wang, Y.; Helland, A.; Holm, R.; Kristensen Gunnar, B.; Borresen-Dale, A.-L. PIK3CA mutations in advanced ovarian carcinomas. Hum. Mutat. 2005, 25, 322.
108. West, K. A.; Castillo, S. S.; Dennis, P. A. Activation of the PI3K/Akt pathway and chemotherapeutic resistance. Drug Resist. Update. 2002, 5, 234-48.
109. Whyte, D. B.; Holbeck, S. L. Correlation of PIK3Ca mutations with gene expression and drug sensitivity in NCI-60 cell lines. Biochem. Biophys. Res. Commun. 2006, 340, 469-475.
110. Wilker, E.; Lu, J.; Rho, O.; Carbajal, S.; Beltran, L.; DiGiovanni, J. Role of PI3K/Akt signaling in insulin-like growth factor-1 (IGF-1) skin tumor promotion. Mol. Carcinog. 2005, 44, 137-145.
111. Workman, P. Inhibiting the phosphoinositide 3-kinase pathway for cancer treatment. Biochem. Soc. Trans. 2004, 32, 393-396.
112. Wu, G.; Xing, M.; Mambo, E.; Huang, X.; Liu, J.; Guo, Z.; Chatterjee, A.; Goldenberg, D.; Gollin, S. M.; Sukumar, S.; Trink, B.; Sidransky, D. Somatic mutation and gain of copy number of PIK3CA in human breast cancer. Breast Cancer Res. 2005, 7, R609-R616.
113. Wymann, M. P.; Sozzani, S.; Altruda, F.; Mantovani, A.; Hirsch, E. Lipids on the move: phosphoinositide 3-kinases in leukocyte function. Immunol. Today 2000, 21, 260-264.
114. Yap, D. B.; Hsieh, J. K.; Lu, X. Mdm2 inhibits the apoptotic function of p53 mainly by targeting it for degradation. J. Biol. Chem. 2000, 275, 37296-302.
115. Yuan, Z.-q.; Feldman, R. I.; Sussman, G. E.; Coppola, D.; Nicosia, S. V.; Cheng, J. Q. AKT2 Inhibition of Cisplatin-induced JNK/p38 and Bax Activation by Phosphorylation of ASK1: Implication of AKT2 in Chemoresistance. J. Biol. Chem. 2003, 278, 23432-23440.
116. Zhao, H.; Dupont, J.; Yakar, S.; Karas, M.; LeRoith, D. PTEN inhibits cell proliferation and induces apoptosis by downregulating cell surface IGF-IR expression in prostate cancer cells. Oncogene 2004, 23, 786-794.
117. Zhao, J. J.; Cheng, H.; Jia, S.; Wang, L.; Gjoerup, O. V.; Mikami, A.; Roberts, T. M. The p110α isoform of PI3K is essential for proper growth factor signaling and oncogenic transformation. Proc. Natl. Acad. Sci. U.S.A 2006, 103, 16296-300.
118. Zhou, B. P.; Liao, Y.; Xia, W.; Spohn, B.; Lee, M.-H.; Hung, M.-C. Cytoplasmic localization of p21Cip1/WAF1 by Akt-induced phosphorylation in HER-2/neu-oyerexpressing cells. Nat. Cell Biol. 2001, 3, 245-252.

REFERENCES

1A. Kenkre V P, Kahl B S. *Curr Hematol Malig Rep* 2012; 7: 216-220
2A. Iyengar S et al. *Blood* 2013; [Epub ahead of print]
3A. Liu N et al. Poster 4476 presented at the 101st Annual Meeting of the American Association for Cancer Research, Washington D.C., USA, Apr. 17-21, 2010
4A. Ziegelbauer K et al. *Br J. Pharmacol* 2005; 145: 178-192
5A. Puri K D, Gold M R. *Front Immunol* 2012; 3: 256
6A. Patnaik A et al. Poster 3704 presented at the 54th ASH Annual meeting and exposition, Atlanta, Ga., USA, Dec. 8-11, 2012
7A. Chou T C. *Pharmacol Rev* 2006; 58: 621-681

The invention claimed is:
1. A method for treatment of non-Hodgkin's lymphoma (NHL), wherein the non-Hodgkin's lymphoma (NHL) is selected from the group consisting of 1st line, 2nd line, relapsed, refractory, indolent or aggressive non-Hodgkin's lymphoma (NHL); follicular lymphoma (FL); chronic lymphocytic leukemia (CLL); marginal zone lymphoma (MZL); diffuse large B-cell lymphoma (DLBCL); mantle cell lymphoma (MCL); transformed lymphoma (TL); and peripheral T-cell lymphoma (PTCL), comprising administering to a patient in need thereof a therapeutically effective amount of 2 amino-N-[7-methoxy-8-(3-morpholin-4-ylpropoxy)-2,3-dihydroimidazo[1,2-c]quinazolin-5-yl]pyrimidine-5-carboxamide dihydrochloride.
2. The method according to claim 1, wherein the non-Hodgkin's lymphoma (NHL) is follicular lymphoma (FL).

3. The method according to claim 1, wherein the non-Hodgkin's lymphoma (NHL) is marginal zone lymphoma (MZL).

\* \* \* \* \*